United States Patent
Kalia et al.

(10) Patent No.: US 6,967,104 B2
(45) Date of Patent: Nov. 22, 2005

(54) RAPID METHOD FOR ESTIMATION OF CHEMICAL OXYGEN DEMAND

(75) Inventors: Vipin Chandra Kalia, Delhi (IN); Vikas Sonakya, Delhi (IN); Neena Raizada, Delhi (IN); Arvind Purshottam Joshi, Delhi (IN)

(73) Assignee: Council of Scientific and Industrial Research, New Delhi (IN)

( * ) Notice: Subject to any disclaimer, the term of this patent is extended or adjusted under 35 U.S.C. 154(b) by 564 days.

(21) Appl. No.: 09/820,538

(22) Filed: Mar. 29, 2001

(65) Prior Publication Data

US 2003/0082817 A1 May 1, 2003

(51) Int. Cl.⁷ .............................................. G01N 33/48
(52) U.S. Cl. ...................... 436/127; 436/164; 436/166; 436/95
(58) Field of Search .......................... 436/95, 127, 164, 436/166

(56) References Cited

U.S. PATENT DOCUMENTS 3,989,600 A * 11/1976 Takahashi et al. ............ 560/77
5,549,789 A * 8/1996 Atalla et al. .................. 162/65

FOREIGN PATENT DOCUMENTS

DE     10029146 A1 * 12/2000

* cited by examiner

*Primary Examiner*—Lyle A. Alexander
(74) *Attorney, Agent, or Firm*—Abelman, Frayne & Schwab

(57) ABSTRACT

The present invention relates to a rapid method for estimation of Chemical Oxygen Demand (COD) of water, COD is an important parameter for determining the extent of pollution in water bodies, the basic principle of COD estimation is not much different from prior art but the time taken is reduced considerably and the results are equally sensitive and reproducible as other methods and the method used to generate data on the performance of effluent treatment plants in remote areas or rural areas, it also provide regular and sequential information on the quality of effluent generated by food processing industries.

21 Claims, 1 Drawing Sheet

(1 of 1 Drawing Sheet(s) Filed in Color)

| COLOUR | COD (mg/L) | COLOUR CODE |
|---|---|---|
|  | 100 | C100 |
|  | 150 | C150 |
|  | 200 | C200 |
|  | 250 | C250 |
|  | 300 | C300 |
|  | 350 | C350 |
|  | 400 | C400 |
|  | 450 | C450 |
|  | 500 | C500 |
|  | 550 | C550 |
|  | 600 | C600 |
|  | 650 | C650 |
|  | 700 | C700 |
|  | 750 | C750 |
|  | 800 | C800 |
|  | 850 | C850 |
|  | 900 | C900 |
|  | 950 | C950 |
|  | 1000 | C1000 |
|  | 1500 | C1500 |
|  | 2000 | C2000 |
|  | 2500 | C2500 |

| COLOUR | COD (mg/L) | COLOUR CODE |
|---|---|---|
|  | 3000 | C3000 |
|  | 3500 | C3500 |
|  | 4000 | C4000 |
|  | 4500 | C4500 |
|  | 5000 | C5000 |
|  | 5500 | C5500 |
|  | 6000 | C6000 |
|  | 6500 | C6500 |
|  | 7000 | C7000 |
|  | 7500 | C7500 |
|  | 8000 | C8000 |
|  | 8500 | C8500 |
|  | 9000 | C9000 |
|  | 9500 | C9500 |
|  | 10000 | C10000 |
|  | 20000 | C20000 |
|  | 30000 | C30000 |
|  | 40000 | C40000 |
|  | 50000 | C50000 |
|  | 100000 | C100000 |

Fig.1 COD Colour Code Chart

RAPID METHOD FOR ESTIMATION OF CHEMICAL OXYGEN DEMAND

FIELD OF THE INVENTION

The present invention relates to a rapid method for estimation of Chemical Oxygen Demand (COD) of water and wastewater. It particularly relates to determination of COD. of industrial waste or domestic waste water or for determining the degree of pollution or develop designs for effluent treatment plants or efficiency of treatment plants or quick, rapid and onsite estimation of COD of water and wastewater or in untreated municipal wastewater or activation and pre-clarification tank inlets or cooling water and storm water reservoirs.

BACKGROUND AND PRIOR ART REFERENCES

Oxygen demand is a significant parameter for determining the effect of organic pollutants in water. As microorganisms in the environment ingest the organic material, oxygen is depleted. This in turn can be harmful to fish and plant life. (http://www.spectronic.com/spectron/spctech2.htm). Wastewater from food processing is non-toxic but organic. High concentration of nutrients can be harmful for the environment. Extra quantities of nitrogen, fat and phosphorus require more oxygen for bacteria to decompose. If Chemical Oxygen Demand (COD/Biochemical oxygen demand (B.O.D) content of the water is excessive, the oxygen supply in the water may be depleted below the level required to sustain aquatic life. (Ref: http://info.rfisk.is/verkefni/1077/hfe 4f2.htm).

The Chemical Oxygen Demand (COD) determination is a measure of the oxygen equivalent of that portion of the organic matter in a sample that is susceptible to oxidation by a strong chemical oxidant under controlled conditions (American Public Health Association (APHA). (1998). In Standard methods for examination of water and wastewater. $20^{th}$ Edn. American Public Health Association (APHA), American Water Works Association (AWWA), Water Pollution Control Federation (WPCF), Washington, DC).

The limitation of the test lies in its inability to differentiate between the biologically oxidizable and biologically inert material. COD determination has an advantage over BOD test in that the results can be obtained in less than five hours where as BOD requires 3 to 5 days. Further the test is relatively easy and with not much interference. (American Public Health Association (APHA), 1976). In: Standard methods for examination of water and wastewater. 14th edn American Public Health Association (APHA), American Water Works Association (AWWA), Water Pollution Control Federation (WPCF), Washington, DC).

The main chemical compounds in wastewater are Chemical Oxygen Demand (COD), nitrogen, phosphorus, fats, oils and grease. COD and BOD_5 are important parameters for measurement of organic matter content and oxygen needed to decompose the organic compounds. During the decomposition of organic matter there is less oxygen available in the sea and no oxygen in some places. It is possible to calculate COD or BOD into standard personal units, 60 g of oxygen to decompose the organic compounds from one person per day or equaling of 135 g of oxygen to decompose Chemical Oxygen Demand (COD) in waste water (COD= 2.25×BOD). (Ref: http://info.rfisk.is/verkefni/1077/hfe_4f2.htm).

The calorimetric dichromate reflux method is commonly used method for determining the Chemical Oxygen Demand (COD) content in a sample, and has been preferred over procedures using other oxidants because of superior oxidizing ability, applicability to a wide variety of samples and ease of manipulation (American Public Health Association (APHA). (1989). In: Standard methods for examination of water and wastewater. 17th edn. American Public Health Association (APHA), American Water Works Association (AWWA), Water Pollution Control Federation (WPCF), Washington, DC). The basic principle involved is oxidizing the most types of organic matters by a boiling mixture of chromic and sulfuric acids. A sample is refluxed in strongly acid solution with a known excess of potassium dichromate ($K_2Cr_2O_7$). After digestion, the remaining unreduced $K_2Cr_2O_7$ is titrated with ferrous ammonium sulfate to determine the amount of $K_2Cr_2O_7$ consumed and the oxidizable organic matter is calculated in terms of oxygen equivalent.

The determination of Chemical Oxygen Demand (COD) is widely used in municipal and industrial laboratories to measure the general level of organic contamination in waste water (Ref: http://www.chemetrics.com/InstProd/COD.I.htm).

Wide ranges of instruments are available for Chemical Oxygen Demand (COD) estimation. CHEMetrics'— employs EPA (Environmental Protection Agency, USA) approved Dichromate reactor digestion method. (http://www.chemetrics.com/InstProd/COD.I.htm). Spectronic Instruments provide SPECTRONIC$^R$ Spectrophotometer and the Bioscience ACCU-Test$^R$ system based on APHA method. (American Public Health Association (APHA). (1989). In: Standard methods for examination of water and wastewater. 17th edn American Public Health Association (APHA), American Water Works Association (AWWA), Water Pollution Control Federation (WPCF), Washington, DC). It uses a semi-micro conversion of the Standard Methods procedure for the determination of Chemical Oxygen Demand (COD). (Ref: http://www.spectronic.com/spectron/ spctech2.htm).

In the North Dakota Department of Health (NDDH), Chemistry Division Chemical Oxygen Demand (COD) SOP (Ref: http://www.health.state.nd.us/lab/ METHODS/ I-I-4.HTM) COD determination is through comparison of absorbance for the standards and the samples in HACH COD reactor and Sequonic Turner model 390 Spectrophotometer.

ISCO-STP COD analyzers and the Phoenix analyzer uses ozone for rapid oxidation and provides continuous Chemical Oxygen Demand (COD) measurement corresponding directly to result of the laboratory standard dichromate method. (http://www.isco/html/ prdprCOD.html).

Among the reference methods of Chemical Oxygen Demand (COD) determination, EPA method 410.1/410.2 and the Standard Method SM5220-D employ closed refluxing (Ref: http:// splash.metrokc.gov/wir/envlab/ LABGUIDE/ com_ref.htm). The biodegradability test—5-day and 28 day includes COD 5 and 15 day determinations in the reference OCED method 3101D—SOQ Appendix B Methods used by Burlington Research, Inc. (Ref: http:// 199.72.5.39/soqapb.htm).

PASTEL UV$^{(R)}$ system works exclusively in UV range of light spectrum with UV analyzer (Spectrophotometer). It requires 16 photodiodes and specially developed pulsed deuterium lamp. This analyzer requires calibration for accuracy within a very specific sample category such as industrial wastewater. For each additional application a new base line spectra has to be customized for specific samples. In this method the co-relation is only for BOD and TSS (Total Suspended Solids) which is 90% when compared to the traditional test methods. For COD the co-relation is valid only upto 6000 mg/L COD only. It is a indirect estimation based on reference data stored in internal UV based software (Ref.: http://www.azurenv.com/ispec.htm). The major limitations in different cases are the economics of the methods used, instruments employed and the time consumed. CHEMetrics' uses a standard digester block for heating the sample for 2 h at 150° C. In addition, the method needs to employ a Chemical Oxygen Demand (COD) Photometer (A-1051C) or Spectrophotometer which accepts a 16 mm diameter cell. The major limitation is that the results are not reportable to USEPA. On the other hand, 13 mm cells can be read in CHEMetrics VVR and A1051 photometer. However, the results are good for monitoring purposes only.

BioScience's EPA Accepted ACCU-TEST$^R$ method needs specific type of Chemical Oxygen Demand (COD) reagent vials, a heating block, data management software package, etc. are required. It makes each test quite costly. BioScience's EPA Accepted ACCU-TEST$^R$ is available only in a medium sensitivity ranges for Spectrophotometry 5 to 4500 mg/L Chemical Oxygen Demand (COD). In order to use the BioScience COD vials in the SPECTRONIC$^R$ 401, both the test tube holder and the Light shield are required where as the GENESYS™ 2 or GENESYS™ 5 require the cell holder Platform and its Test tube holder (Ref:http://www.spectronic.com/spectron/spctech2.htm).

In the North Dakota Department of Health (NDDH) Chemistry Division Chemical Oxygen Demand (COD.) SOP (Ref: http://www.health.state.nd.us/ lab/METHODS/I-I-4.HTM) Chemical Oxygen Demand (COD) determination is in a narrow range of 0 to 150 and 150 to 1500 mg/L. The calorimetrically determined Chemical Oxygen Demand (COD) value is based on measuring the consumed oxidant in the chrome ($Cr^{6+}$) and chromous ($Cr^{3+}$) valence state. The method employs HACH COD reactor and Sequonic Turner model 390 Spectrophotometer. The spiking solutions in the 0 to 150 mg/L range are 10, 25, 50 and 150 where as for 150 to 1500 mg/L ranges, 5 concentration ranges 100, 250, 500, 1000 and 1500) are employed. It needs a sample volume of 10 ml, in addition to heating for 2 hours at 150° C.

In the Manganese III method for Chemical Oxygen Demand (COD) analysis (U.S. Pat. No. 5,556,787 September, 1996) determination is done by using an analysis reagent comprised of a mixture of stabilized Manganese III ion and an inorganic non-oxidizing acid such as sulfuric or phosphoric acid. The method involves titration and calorimetric determination. The method involves digestion of the test sample by heating between 100 to 200° C. for up to 2 hours.

A method based on redox cell involved treatment of organic carbon with an excess of an oxidizing agent. The remaining oxidizing agent is determined in a redox cell to ascertain how much of the oxidizing agent was consumed by the organic carbon. This was the COD. This is multi-step process involving a large number of reagents (U.S. Pat. No. 3,930,798 January, 1976). Another redox based method involves ozone as an oxidizing agent (U.S. Pat. No. 5,324,666 June, 1994). The accuracy of the process is limited only by the control range of the ozone generating pumps. It can work within a range of less than 0.5 ozone load i.e. the ratio of chemical oxygen demand to added ozone. By increasing the ozone input the measuring range may be extended upwards but with reduced accuracy.

All the methods employed so far have long refluxing or digestion periods and are followed by titration or spectro-photometric reading of the standards and the samples at different wavelengths.

In the present invention the major limitations involved in estimation of chemical oxygen demand of water and wastewater have been over come. The novelty of the present invention is in use of a rapid, simple and effective method for estimation of COD of a wide range of samples. Another novelty of the present invention is the reduction in time period taken for estimation of COD, from 2h to less than 5 minutes. In the present invention, parameters have been studied for preparation of a reaction mixture, which is easy to handle. Another novelty of the present invention is in the use of very small quantities of reagents and the test sample. In the present invention the various reaction mixtures can be read instantly for a very wide range of COD loads by using minor equipment e.g. photometer. Another novelty of the present invention is the ability to conduct the estimation on site, avoiding any possible changes in the test sample quality. Yet another novelty of the present invention is the COD color chart is used for determination of COD. over a wide range. Another novelty of the present invention is the flexibility to use reagents for determination of COD. over a wide range. Another novelty of the present invention is the simplicity for preparing reference standards easily and rapidly. Another novelty of the present invention is the stability of color based reference standards for long period without preserving them at low temperatures. These can thus be used repeatedly.

OBJECTS OF THE INVENTION

The main object of present invention is to provide a rapid method for estimation of Chemical Oxygen Demand (COD) of water and wastewater, which obviates the drawbacks listed above.

Another object of the present invention is to provide a cheap and simple method for quick estimation of COD of water and wastewater.

Yet, another object of present invention is to provide a rapid and sensitive method which, capable of determining COD in small quantities of test sample.

Yet another object of the present invention is to provide a color chart over a wide range of COD values.

Yet, another object of the present invention is to provide a kit for COD. estimation.

Yet, another object of the present invention is to provide a method which does not require much technical skill and sophisticated equipment.

Another object of the present invention is to provide an effective process for COD estimation with very little loss of sample.

SUMMARY OF THE INVENTION

The present invention has solved the problem of longer duration and consumption of large quantities of chemicals in COD estimation. The method of the invention has removed the need for heating the reaction mixture for nearly 2 h at 148° C., which is conventionally employed by standard methods and other commercially available kits.

One mL of sample solution is mixed with three reagents, consisting of 0.02 g mercuric sulphate, 0.5 mL of 0.25 N potassium dichromate solution and 1.5 mL of sulphuric acid—silver sulphate in a sequential manner. Its COD is checked with the help of color chart. Sample(s) showing a COD value of more than 10000 mg/L are diluted. After establishing its approximate COD value, the sample is diluted further, if necessary, to achieve a COD value in the range of 300 to 500 mg/L. Reagents listed above are added to these diluted sample and read its OD at 585 and 635 nm. These OD values are used for calculating precise COD values by comparing it with standard glucose solution.

The main utility of the present invention is for determining the degree of pollution, to develop designs for effluent treatment plants and to determine efficiency of treatment plants. Monitoring of COD is important for design and operation of wastewater treatment equipment. Another utility of the present invention is to provide an efficient method for quick, rapid and onsite estimation of COD of water and wastewater. Other utilities include applications in untreated municipal wastewater, activation and pre-clarification tank inlets, and even cooling water and storm water reservoirs. It is also used as a standard parameter for characterization of wastewater loads or for proof of a required purification level.

DETAILED DESCRIPTION OF THE INVENTION

The chemical oxygen demand (COD) determines the amount of oxygen required for chemical oxidation of organic matter using a strong chemical oxidant such as potassium dichromate under reflux conditions. The test is widely used to determine: 1) The degree of pollution in water bodies and their self purification capacity, 2) Efficiency of treatment plants, 3) Pollution loads, 4) Provides rough idea of B.O.D, which can be used for B.O.D estimation. The conventional estimation is based on the principle that most of the organic matter is destroyed when boiled with a mixture of potassium dichromate and $H_2SO_4$ producing $CO_2$ and $H_2O$. A sample is refluxed with a known amount of potassium dichromate. It is then titrated against ferrous ammonium sulphate. The amount is proportional to $O_2$ required to oxidize the organic matter. The method takes 2 to 3 hours. Using standard COD kits available in the market can also do COD estimations. The standard COD kit method involves the use of thermoreactor and a photometer can also take 2 to 3 hours to complete. Since the initial COD of the sample cannot be guessed, kits for different COD ranges have to be tried and even sample may still has to be diluted. Dilution of sample leads to further use of more kits, it thus makes the estimation more expensive. However, a technique has been devised here, which gives good estimate of COD within 5 to 10 min and consumes very small quantities of reagents compared to conventional standard methods. It can be carried out easily on site. The reaction mixture develops a color, which can be easily read and distinguished. In the first stage, a sample is added without any dilution. The color developed with the undiluted sample gives a direct estimate of COD or gives a clear indication of the extent to which a sample needs to be diluted before adding to the reaction mixture. For samples with COD value of more than 10000, the color of the sample and the different reagents will be C10000 (brown). Make 4 different dilutions of the sample i.e. 10, 100, 200 and 500. The various diluted samples can be tested in increasing order of their dilution. Once a diluted sample and the reagent mixture show a color between C100 (yellow) and C500 (sea green). This dilution can be 10 to 300 times, depending upon the initial COD of the sample.

Accordingly, the present invention provides a rapid method for semi-quantitative estimation of Chemical Oxygen Demand (COD), which comprises:

i) preparing standard solutions by dissolving glucose in water, ii) mixing the standard solutions with different reagents, mercuric sulphate ($HgSO_4$), potassium dichromate ($K_2Cr_2O_7$) and sulphuric acid ($H_2SO_4$) silver sulphate reagent in a sequential manner.

iii) mixing the sample with different reagents, mercuric sulphate ($HgSO_4$), potassium dichromate ($K_2Cr_2O_7$) and sulphuric acid ($H_2SO_4$) silver sulphate reagent in a sequential manner.

iv) diluting the sample to a desired level and adding the reagents in a sequential manner.

v) noting down the color of the reaction mixture visually and record the color code using a color chart within 1 minute of incubation and reading optical density (O.D.) of the sample.

Accordingly the present invention provides a method for the preparation of COD chart useful for the estimation of COD in a sample, said method comprising the steps of:

a) preparing standard glucose solution by dissolving glucose in distilled water at a concentration ranging between 200 mg/L to 100,000 mg/L with a COD concentration ranging between 213 mg/L to 106,700 mg/L, b) mixing 1 mL of standard glucose solutions from step (a), individually, with three reagents, consisting of 0.02 g mercuric sulfate, 0.5 mL of 0.25 N potassium dichromate solution and 1.5 mL of sulfuric acid—silver sulfate in a sequential manner, and c) preparing a COD color chart of different glucose concentration as shown in FIG. 1 of accompanying drawings based on the COD concentration ranging between 213 mg/L to 106,700 mg/L, and which chart is useful for rough estimation of COD values by comparing the colors of the chart with the color of the samples.

The present invention also provides a rapid method for the estimation of COD of an effluent from domestic, industrial, municipal and other sources, said method comprising the steps of a) preparing a set of standard glucose solutions by dissolving glucose in distilled water at a concentration ranging between 300 mg/L to 500 mg/L, with a COD concentration of 320 mg/L to 535 mg/L, b) mixing 1 mL of standard glucose solutions from step (a), individually, with three reagents, consisting of 0.02 g mercuric sulfate, 0.5 mL of 0.25 N potassium dichromate solution and 1.5 mL of sulfuric acid—silver sulfate in a sequential manner, c) mixing 1 mL of a sample to be tested with 0.01 to 0.03 g mercuric sulfate per ml of a standard glucose solution, 0.5 mL of 0.25 N to 0.30 N potassium dichromate and 1.5 mL of sulfuric acid—silver sulfate reagents in a sequential manner and noting down the color and if the color of the reaction mixture turns (color code C10000) brown, d) diluting the sample according to table 1(a) with distilled water till a particular color range of C100 to C10000 is achieved as shown in FIG. 1 of accompanying drawing, e) further diluting the sample with distilled water to obtain a COD range in between 320 to 535 mg/L wherein the dilution is determined according to tables 1(a) & (b), f) mixing 1 mL of diluted sample from step (e), individually, with three reagents, consisting of 0.02 g mercuric sulfate, 0.5 mL of 0.25 N to 0.30 N potassium dichromate solution and 1.5 mL of sulfuric acid—silver sulfate in the above sequential manner, g) matching the color of the reaction mixture of the above sample (step f) with the COD color chart provided in FIG. 1 of the accompanying drawing, h) noting the optical density (OD) of the reaction mixture of standard glucose solutions (step b) and sample (step f) at 585 nm or 635 nm, against air, i) drawing a correlation between the OD values of above sample with OD values of standard glucose solutions, j) multiplying the OD value of sample (step h) with a correction factor of 1.2, comparing this value (A) with the OD value of standard glucose solution of COD value 320 to 535 mg/l, k) multiplying value (A) with the compared COD value of standard Glucose solution and divided by the respective OD value of the glucose standard (B), and l) then multiply value (B) with a dilution factor (in case of diluted sample) to obtain the COD value of the sample in terms of mg/l.

In yet another embodiment, the tables 1(a) and 1(b) are as follows:

TABLE 1(a)

| Color of the reaction mixture | Required dilution of sample | Color code | Expected COD of unknown sample (mg/L) |
|---|---|---|---|
| C 10000 | 10  | C1000     | 10000 |
| C 10000 | 100 | C100–C500 | 10000–50000 |
| C 10000 | 200 | C250–C500 | 50000–100000 |
| C 10000 | 500 | C200–C2000 | 100000–1000000 |

TABLE 1(b)

| Color of the reaction mixture | Expected COD (mg/L) | Dilution required to bring COD value (300–500 mg/L) |
|---|---|---|
| C9000 | 9000–9500 | 18–31 |
| C6000 | 6000–8500 | 12–28 |
| C2000 | 2000–5500 | 4–18 |
| C1500 | 1500–1900 | 3–6 |
| C1200 | 1200–1400 | 2–5 |
| C600  | 600–1100  | 2–4 |
| C500  | 500–550   | NIL |
| C400  | 400–450   | NIL |
| C300  | 300–350   | NIL |
| C200  | 200–250   | NIL |
| C150  | 100–150   | NIL |
| C100  | 00–100    | NIL |

In yet another embodiment, in step (d) the dilution of samples, provide dark brown reaction mixture, falling in the range of 10 to 500 for approximate cod values of 10000 mg/l and above as given in Table 1(c) and further dilution of nil to 31 is done to bring the COD in the range of 300 to 500 mg/l as given in Table 1(d).

In yet another embodiment, in step (e), the samples provide yellowish to blackish brown colored reaction mixture falling in the range of 100 to 9500 mg/l COD and the samples are further diluted to 31 times to obtain a diluted sample in the COD range of 300 to 500 mg/l, according to the Table 1(d).

In yet another embodiment, in step (d) the dilution of samples and color groups range from (A) to (G) for approximate COD values lying in the range of 100 to 9500 mg/l as given in table 1(d)

In yet another embodiment, tables 1(c) and 1(d) are shown below.

TABLE 1(c)

| Color of the reaction mixture | Color code of the reaction mixture as per the provided chart | Dilution required to bring the COD values in the range of 100–1000 mg/l | Color obtained on dilution as per the provided color chart | Expected COD of the reaction mixture (mg/l) | Expected COD of unknown sample (mg/l) |
|---|---|---|---|---|---|
| Dark brown | C 10000 to C 100000 | i) 10    | C 1000        | 1000       | 10000 |
|            |                     | ii) 100  | C 100–C500    | 100 to 500 | 10000 to 50000 |
|            |                     | iii) 200 | C 250–C 500   | 250 to 500 | 50000 to 100000 |
|            |                     | iv) 500  | C 200 to C 2000 | 200 to 2000 | 100000 to 1000000 |

TABLE 1(d)

| Color group | Color of the reaction mixture | Color code of the reaction mixture as per the chart provided | Expected COD of the reaction mixture | Dilution required to bring the COD values in the range of 300 to 500 mg/l |
|---|---|---|---|---|
| A | Yellowish           | C 100 to C 250  | 1 to 250    | Nil |
| B | Yellowish           | C 300 to C 550  | 300 to 550  | Nil |
| C | Greenish blue       | C 600 to C 1000 | 600 to 1000 | 2 to 4 |
| D | Blue to grayish blue| C 1500 to C 2500| 1500 to 2500| 3 to 6 |
| E | Dirty brown         | C 3000 to C 5500| 3000 to 5500| 6 to 18 |
| F | Cola brown          | C 6000 to C 8500| 6000 to 8500| 12 to 28 |
| G | Blackish brown      | C 9000 to 9500  | 9000 to 9500| 18–31 |

One more embodiment of the invention provides a kit for estimation of Chemical Oxygen Demand (COD) which comprises:
   a) reagents A) $HgSO_4$ (solid), B) Glucose standard solutions ranging from 300 to 500 mg/L, C). $K_2Cr_2O_7$ solution (0.25 to 0.3 N), and D) $H_2SO_4$—silver sulfate reagent,
   b) a glass vial,
   c) a photometric cell,
   d) a COD color chart as shown in FIG. 1 of the accompanying drawing and a photometer suitable for wave lengths in the range of 585 to 635 nm.

One more embodiment the present invention a method for the preparation of reference tables 1(e) and 1(f) of COD values, useful for the estimation of COD in a sample, said method comprising the steps of:
   a) preparing standard glucose solution by dissolving glucose in distilled water at a concentration ranging between 200 mg/L to 1,00,000 mg/L with a COD concentration ranging between 213 mg/L to 1,06,700 mg/L,
   b) mixing 1 mL of standard glucose solutions from step (a), individually, with three reagents, consisting of 0.02 g mercuric sulfate, 0.5 mL of 0.25 N potassium dichromate solution and 1.5 mL of sulfuric acid—silver sulfate in a sequential manner, and
   c) preparing reference tables 1(e) and 1(f) for COD values of different glucose concentration based on the COD concentration ranging between 213 mg/L to 1,06,700 mg/L, and which tables are useful for rough estimation of COD values by comparing the colors indicated in the tables with the color of the samples.

In another embodiment the present invention provides the reference tables 1(e) and 1(f) are as shown below.

TABLE 1(e)

| Color of the reaction mixture | Dilution required to bring the COD values in the range of 100–1000 mg/l | Expected COD of the reaction mixture (mg/l) | Expected COD of unknown sample (mg/l) |
|---|---|---|---|
| Dark brown | v) 10 | 1000 | 10000 |
|  | vi) 100 | 100 to 500 | 10000 to 50000 |
|  | vii) 200 | 250 to 500 | 50000 to 100000 |
|  | viii) 500 | 200 to 2000 | 100000 to 1000000 |

TABLE 1(f)

| Color group | Color of the reaction mixture | Expected COD of the reaction mixture | Dilution required to bring the COD values in the range of 300 to 500 mg/l |
|---|---|---|---|
| A | Yellowish | 1 to 250 | Nil |
| B | Yellowish | 300 to 550 | Nil |
| C | Greenish blue | 600 to 1000 | 2 to 4 |
| D | Blue to grayish blue | 1500 to 2500 | 3 to 6 |
| E | Dirty brown | 3000 to 5500 | 6 to 18 |
| F | Cola brown | 6000 to 8500 | 12 to 28 |
| G | Blackish brown | 9000 to 9500 | 18–31 |

In another embodiment, the present invention provides a rapid method for the estimation of COD of an effluent from domestic, industrial, municipal and other sources using reference tables as given above, said method comprising the steps of a) preparing a set of standard glucose solutions by dissolving glucose in distilled water at a concentration ranging between 300 mg/L to 500 mg/L, with a COD concentration of 320 mg/L to 535 mg/L,
   b) mixing 1 mL of standard glucose solutions from step (a), individually, with three reagents, consisting of 0.02 g mercuric sulfate, 0.5 mL of 0.25 N potassium dichromate solution and 1.5 mL of sulfuric acid—silver sulfate in a sequential manner,
   c) mixing 1 mL of a sample to be tested with 0.02 g mercuric sulfate, 0.5 mL of 0.25 N potassium dichromate and 1.5 mL of sulfuric acid—silver sulfate reagents in a sequential manner and noting down the color till the color of the reaction mixture turns brown,
   d) diluting the sample as per tables 1(e) and 1(f) with distilled water till a particular color range shown in the tables is achieved,
   e) further diluting the sample with distilled water to obtain a COD range in between 320 to 535 mg/L wherein the dilution is determined according to tables 1(e) and 1(f),
   f) mixing 1 mL of diluted sample from step (e), individually, with three reagents, consisting of 0.02 g mercuric sulfate, 0.5 mL of 0.25 N to 0.30 N potassium dichromate solution and 1.5 mL of sulfuric acid—silver sulfate in the above sequential manner,
   g) matching the color of the reaction mixture of the above sample (step f) with the COD color provided in tables 1(e) and 1(f),
   h) noting the optical density (OD) of the reaction mixture of standard glucose solutions (step b) and sample (step f) at 585 nm or 635 nm, against air,
   i) drawing a correlation between the OD values of above sample with OD values of standard glucose solutions,
   j) multiplying the OD value of sample (step h) with a correction factor of 1.2, comparing this value (A) with the OD value of standard glucose solution of COD value 320 to 535 mg/l,
   k) multiplying value (A) with the compared COD value of standard Glucose solution and divided by the respective OD value of the glucose standard (B) and
   l) then multiply value (B) with a dilution factor (in case of diluted sample) to obtain the COD value of the sample in terms of mg/l.

In yet another embodiment, in step d, the dilution of samples provide dark brown reaction mixture falling in the range of 10 to 500 for approximate cod values of 10000 mg/l and above as given in Table 1(e) and further dilution of nil to 31 is done to bring the COD in the range of 300 to 500 mg/l as given in Table 1(f).

In yet another embodiment, in step (e), the samples provide yellowish to blackish brown coloured reaction mixture falling in the range of 100 to 9500 mg/l COD and the samples are further diluted to 31 times to obtain a diluted sample in the COD range of 300 to 500 mg/l, according to the Tables 1(e) and 1(f).

In yet another embodiment, in step (d) the dilution of samples and color groups range from (A) to (G) for approximate COD values lying in the range of 100 to 9500 mg/l as given in table 1(d).

In one embodiment of the present invention, the Dilution Factor is the total volume used divided by volume of the sample.

In another embodiment, the effluent used is selected from domestic, industrial, municipal, agricultural and other waste material sources.

In still another embodiment of the invention, the waste material is in the form of solid, liquid, semi-solid or viscous forms.

In yet another embodiment, the reagents used are $HgSO_4$, glucose standard solutions, $K_2Cr_2O_7$ solution and $H_2SO_4$—silver sulfate reagent.

In yet another embodiment, the volume of the test sample or standard solution used ranges from 20 to 100 ml.

In yet another embodiment, the incubation is carried out for a period in the range between 15 seconds to 1 minute.

In yet another embodiment, the estimated COD is in the range between 80 to 106700 mg/L.

In yet another embodiment, the glucose concentration tested is ranging between 50 to 100000 mg/L.

In yet another embodiment, the amount of $HgSO_4$ used in the test samples is from 10 mg to 30 mg.

In yet another embodiment, the concentration of $K_2Cr_2O_7$ used in the test samples is from 0.25 Normal to 0.30 Normal.

In yet another embodiment, the quantity of $H_2SO_4$—silver sulfate reagent used in the test samples is 1.5 mL.

In yet another embodiment, the COD color chart is applicable for the COD values ranging between 100 to 10,000 mg/L.

In yet another embodiment, the test samples having COD value more than 10000 mg/L is diluted appropriately.

In yet another embodiment, the OD (optical density) of the sample is read at the wavelengths 585 and 635 nm.

In yet another embodiment, the optical density readings are measured for the COD values ranging from 320 to 535 mg/L.

In yet another embodiment, the sample is in the form of slurry.

In yet another embodiment, the sample used for COD estimation comprises of agricultural waste, municipal market waste, fruit and food industry waste, beverages, chemicals, microbes and animal waste etc.

In yet another embodiment of the present invention, the kit for estimation of Chemical Oxygen Demand (COD) which may comprise of:

1. Reagents such as: A. $HgSO_4$ (solid), B. Glucose standard solutions ranging from 300 to 500 mg/L, C. $K_2Cr_2O_7$ solution (0.25 to 0.3 N), D. $H_2SO_4$—silver sulfate reagent,
2. a glass vial,
3. a photometric cell,
4. reference tables 1(e) and 1(f),
5. a photometer suitable for wave lengths in the range of 585 to 635 nm.

BRIEF DESCRIPTION OF THE DRAWINGS

The file of this patent contains at least one drawing executed in color. Copies of this patent with color drawing(s) will be provided by the Patent & Trademark Office upon request and payment of the necessary fee.

FIG. 1 is a color code chart of COD values.

Having now generally described this invention, a further understanding can be obtained by reference to certain specific examples, which are provided herein for purposes of illustration only and are not intended to be limiting unless otherwise specified.

EXAMPLE 1

Dissolved 0.5 and 5 g glucose in 50 mL distilled water, separately. Aliquots from the stock solutions were taken and diluted with water to achieve different concentrations in the range of 200 to 5000 (COD: 213 to 5335 mg/L) and 10000 to 100000 mg/L (COD: 10670 to 106700 mg/L), respectively. Weighed 0.02 g $HgSO_4$ in separate 15 mL and 50 mL test tubes. 1.0 mL of glucose sample was added to each test tube and shake well. 0.5 ml of $K_2Cr_2O_7$ was added to each sample. 1.5 mL $H_2SO_4$ silver sulphate reagent was added slowly with continuous shaking. The color of the reaction mixture was noted down visually within 1 min of incubation. The color varied with concentration. In 200 to 5000 mg/L glucose solutions, the color varied from C200 to C5000. At 5000 mg/L glucose and higher concentrations, the final color was always turbid. However, at concentration above 10000 mg/L glucose concentrations, the final color was always brown (C10000) and turbid. Hence for a preliminary estimate of COD value, color of the standard reaction mixture based on a range of glucose concentrations can be used as a reference. For samples, with initial COD concentration of 10000 or more, the sample needs to be diluted and its COD, re-estimated by taking the dilution factor and color of the reaction mixture into consideration.

TABLE 1

Correlation between COD concentration and color of the reaction mixture.

| Glucose Concentration (mg/L) | COD of Glucose the solution (mg/L) | Color of the reaction mixture |
|---|---|---|
| 00 (Blank) | 0.0 | C00 |
| 200 | 213.4 | C200 |
| 250 | 266.7 | C250 |
| 300 | 320.1 | C300 |
| 350 | 373.4 | C350 |
| 400 | 426.8 | C400 |
| 450 | 480.1 | C450 |
| 500 | 533.5 | C500 |
| 600 | 640.2 | C600 |
| 700 | 746.9 | C700 |
| 800 | 853.6 | C800 |
| 900 | 960.3 | C900 |
| 1000 | 1067.0 | C100 |
| 1500 | 1600.5 | C1500 |
| 2000 | 2134.0 | C2000 |
| 2500 | 2667.5 | C2500 |
| 3000 | 3201.0 | C3000 |
| 3500 | 3734.5 | C3500 |
| 4000 | 4268.0 | C4000 |
| 4500 | 4801.5 | C4500 |
| 5000 | 5335.0 | C5000 |
| 10000 | 10670.0 | C10000 |
| 50000 | 53350.0 | C50000 |
| 100000 | 106700.0 | C100000 |

EXAMPLE 2

Dissolved 0.5 and 5 g glucose in 50 mL and 100 mL distilled water, respectively. Aliquots from the stock solutions were taken and diluted with water to achieve different concentrations in the range of 50 to 5000 (COD: 80 to 5335 mg/L) and 5500 to 100000 mg/L (COD: 5868 to 106700 mg/L), respectively. Weighed 0.02 g $HgSO_4$ in separate 15 mL and 50 mL test tubes. 1.0 mL of glucose sample was added to each test tube and shake well. 0.5 mL of $K_2Cr_2O_7$ was added to each sample. 1.5 mL $H_2SO_4$ silver sulphate reagent was added slowly with continuous shaking. The color of the reaction mixture was noted down visually within 1 min of incubation. The color varied with concentration. In 50 to 9500 mg/L glucose solutions, the color varied from C50 to C9500. At 5500 mg/L glucose and higher concentrations, the final color was always turbid. However, at concentration above 10000 mg/L glucose concentrations, the final color was always C10000. Hence, for a preliminary estimate of COD value, color of the standard reaction mixture based on a range of glucose concentrations can be used as a reference. For samples, with initial COD concentration of 10000 or more, the sample needs to be diluted and its COD, re-estimated by taking the dilution factor and color of the reaction mixture into consideration.

TABLE 2

Correlation between COD concentration and color of the reaction mixture.

| Glucose Concentration (mg/L) | COD of Glucose solution (mg/L) | Color of the reaction mixture |
|---|---|---|
| 00 (Blank) | 0.0 | C00 |
| 50 | 80.3 | C50 |
| 100 | 106.7 | C100 |
| 150 | 241.0 | C150 |
| 200 | 213.4 | C200 |
| 250 | 266.7 | C250 |
| 300 | 320.1 | C300 |
| 350 | 373.4 | C350 |
| 400 | 426.8 | C400 |
| 450 | 480.1 | C450 |
| 500 | 533.5 | C500 |
| 550 | 583.8 | C550 |
| 600 | 640.2 | C600 |
| 650 | 693.5 | C650 |
| 700 | 746.9 | C700 |
| 750 | 800.2 | C750 |
| 800 | 853.6 | C800 |
| 850 | 906.9 | C850 |
| 900 | 960.3 | C900 |
| 950 | 1013.6 | C950 |
| 1000 | 1067.0 | C1000 |
| 1100 | 1173.7 | C1100 |
| 1200 | 1280.4 | C1200 |
| 1300 | 1387.1 | C1300 |
| 1400 | 1493.8 | C1400 |
| 1500 | 1600.5 | C1500 |
| 1600 | 1707.2 | C1600 |
| 1700 | 1813.9 | C1700 |
| 1800 | 1920.6 | C1800 |
| 1900 | 2027.3 | C1900 |
| 2000 | 2134.0 | C2000 |
| 2500 | 2667.5 | C2500 |
| 3000 | 3201.0 | C3000 |
| 3500 | 3734.5 | C3500 |
| 4000 | 4268.0 | C4000 |
| 4500 | 4801.5 | C4500 |
| 5000 | 5335.0 | C5000 |
| 5500 | 5868.5 | C5500 |
| 6000 | 6402.0 | C6000 |
| 6500 | 6935.5 | C6500 |
| 7000 | 7469.0 | C7000 |
| 7500 | 8002.5 | C7500 |
| 8000 | 8536.0 | C8000 |
| 8500 | 9069.5 | C8500 |
| 9000 | 9603.0 | C9000 |
| 9500 | 10136.5 | C9500 |
| 10000 | 10670.0 | C10000 |
| 15000 | 16005.0 | C15000 |
| 20000 | 21340.0 | C20000 |
| 30000 | 32010.0 | C30000 |
| 40000 | 42680.0 | C40000 |
| 50000 | 53350.0 | C50000 |
| 100000 | 106700.0 | C100000 |

EXAMPLE 3

Dissolved g glucose in 50 ml distilled water. Aliquots from the stock solution were taken and diluted with water to achieve different concentrations in the range of 100 to 2000 mg/L (COD: 106.7 to 2134 mg/L). Weighed 0.02 g $HgSO_4$ in separate 15 mL and 25 mL test tubes. 1.0 ml of glucose sample was added to each test tube and shake well. 0.5 ml of $K_2Cr_2O_7$ was added to each sample. 1.5 ml $H_2SO_4$ silver Sulphate reagent was added slowly with continuous shaking. The color of the reaction mixture was noted down visually within 1 min of incubation and also recorded spectrophotometrically at 585 and 635 nm against air. The color varied with concentration. In 100 to 2000 mg/L glucose solutions, the color varied from C100 to C2000. At 100 to 800 mg/L glucose concentrations, OD 585 varied from 0.104 to 0.307 and OD 585 and OD 635 varied from 0.092 to 0.276. In the COD range of 106.7 to 640.2 mg/L the OD 585 and OD 635 there was an incremental difference of 0.030 and 0.027 each 106.7 mg/L COD increase, respectively. At different wavelengths, OD became stable at 1000 mg/L glucose and higher concentrations. Hence for a preliminary estimate of COD value, color of the standard reaction mixture based on a range of glucose concentrations can be used as a reference. For samples, with initial OD concentration of 100 to 640 mg/L, OD 585 or OD 635 can be recorded for obtaining more values that are precise.

TABLE 3

Correlation between COD concentration, color of the reaction mixture and their OD at different wave lengths.

| Glucose Concentration (mg/L) | COD of Glucose solution (mg/L) | Color of the reaction mixture | OD 585 nm of the reaction mixture | OD 635 nm of the reaction mixture |
|---|---|---|---|---|
| 100 | 106.7 | C100 | 0.104 | 0.092 |
| 200 | 213.4 | C200 | 0.133 | 0.117 |
| 300 | 320.1 | C300 | 0.164 | 0.143 |
| 400 | 426.8 | C400 | 0.196 | 0.165 |
| 500 | 533.5 | C500 | 0.222 | 0.193 |
| 600 | 640.2 | C600 | 0.252 | 0.226 |
| 800 | 853.6 | C800 | 0.307 | 0.276 |
| 1000 | 1067.0 | C1000 | 0.362 | 0.332 |
| 1200 | 1280.4 | C1200 | 0.347 | 0.316 |
| 1400 | 1493.8 | C1400 | 0.351 | 0.323 |
| 1600 | 1707.2 | C1600 | 0.354 | 0.354 |
| 1800 | 1920.6 | C1800 | 0.344 | 0.328 |
| 2000 | 2134.0 | C2000 | 0.358 | 0.343 |

EXAMPLE 4

Dissolved 1 g glucose in 100 mL distilled water. Aliquots from the stock solution were taken and diluted with water to achieve different concentrations in the range of 100 to 2000 mg/L (COD: 106.7 to 2134 mg/L). Weighed 0.02 g $HgSO_4$ in separate 15 mL and 25 mL test tubes. 1.0 mL of glucose sample was added to each test tube and shake well. 0.5 ml of $K_2Cr_2O_7$ was added to each sample. 1.5 ml $H_2SO_4$ silver sulphate reagent was added slowly with continuous shaking. The color of the reaction mixture was noted down visually within 30 sec of incubation and also recorded spectrophotometrically at 585 and 635 nm against air. The color varied with concentration. In 100 to 2000 mg/L glucose solutions, the color varied from C100 to C2000. At 100 to 1000 mg/L glucose concentrations, OD 585 varied from 0.109 to 0.347 and OD 635 varied from 0.096 to 0.317. In the COD range of 106.7 to 640.2 mg/L the OD 585 and OD 635 there was an incremental difference of 0.027 and 0.026 for each 106.7 mg/L COD increase, respectively. At different wavelengths, OD became stable at 1000 mg/L glucose and higher concentrations. Hence, for a preliminary estimate of COD value, color of the standard reaction mixture based on a range of glucose concentrations can be used as a reference. For samples, with initial COD concentration of 100 to 640 mg/L, OD 585 or OD 635 can be recorded for obtaining more precise values.

TABLE 4

Correlation between COD concentration, color of the reaction mixture and their OD at different wave lengths.

| Glucose Concentration (mg/L) | COD of Glucose solution (mg/L) | Color of the reaction mixture | OD 585 nm of the reaction mixture | OD 635 nm of the reaction mixture |
|---|---|---|---|---|
| 100 | 106.7 | C100 | 0.109 | 0.096 |
| 200 | 213.4 | C200 | 0.132 | 0.116 |
| 300 | 320.1 | C300 | 0.161 | 0.142 |
| 400 | 426.8 | C400 | 0.193 | 0.164 |
| 500 | 533.5 | C500 | 0.222 | 0.195 |
| 600 | 640.2 | C600 | 0.246 | 0.226 |
| 800 | 853.6 | C800 | 0.300 | 0.274 |
| 1000 | 1067.0 | C1000 | 0.347 | 0.317 |
| 1200 | 1280.4 | C1200 | 0.350 | 0.321 |
| 1400 | 1493.8 | C1400 | 0.341 | 0.326 |
| 1600 | 1707.2 | C1600 | 0.352 | 0.332 |
| 1800 | 1920.6 | C1800 | 0.354 | 0.331 |
| 2000 | 2134.0 | C2000 | 0.354 | 0.349 |

EXAMPLE 5

Dissolved 0.25 g glucose in 25 mL distilled water. Aliquots from the stock solution were taken and diluted with water to achieve different concentrations in the range of 100 to 500 mg/L (COD: 106.7 to 533.5 mg/L). Weighed 0.02 g $HgSO_4$ in separate 15 mL test tubes. 1.0 mL of glucose sample was added to each test tube and shake well. 0.5 mL of $K_2Cr_2O_7$ was added to each sample. 1.5 mL $H_2SO_4$ silver sulphate reagent was added slowly with continuous shaking. The color of the reaction mixture was noted down visually within 30 sec of incubation and also recorded spectrophotometrically at 585 and 635 nm against air. The color varied with concentration. In 100 to 500 mg/L glucose solutions, the color varied from C100 to C500. At 100 to 500 mg/L glucose concentrations, OD 585 varied from 0.106 to 0.223 and OD 635 varied from 0.089 to 0.199. In the COD range of 106.7 to 533.5 mg/L the OD 585 and OD 635 there was an incremental difference of 0.029 and 0.027 for each 106.7 mg/L COD increase, respectively. Hence, for a preliminary estimate of COD value, color of the standard reaction mixture based on a range of glucose concentrations can be used as a reference. For samples, with initial COD concentration of 106.7 to 533.5 mg/L, OD 585 or OD 635 can be recorded for obtaining more precise values.

TABLE 5

Correlation between COD concentration, color of the reaction mixture and their OD at different wave lengths.

| Glucose Concentration (mg/L) | COD of Glucose solution (mg/L) | Color of the reaction mixture | OD 585 nm of the reaction mixture | OD 635 nm of the reaction mixture |
|---|---|---|---|---|
| 100 | 106.7 | C100 | 0.106 | 0.089 |
| 200 | 213.4 | C200 | 0.133 | 0.116 |
| 300 | 320.1 | C300 | 0.162 | 0.144 |
| 400 | 426.8 | C400 | 0.192 | 0.166 |
| 500 | 533.5 | C500 | 0.223 | 0.199 |

EXAMPLE 6

Dissolved 0.2 g glucose in 50 mL distilled water. Aliquots from the stock solution were taken and diluted with water to achieve different concentrations in the range of 100 to 500 mg/L (COD: 106.7 to 533.5 mg/L). Weighed 0.02 g $HgSO_4$ in separate 15 mL test tubes. 1.0 ml of glucose sample was added to each test tube and shake well. 0.5 ml of $K_2Cr_2O_7$ was added to each sample. 1.5 mL $H_2SO_4$ silver sulphate reagent was added slowly with continuous shaking. The color of the reaction mixture was noted down visually within 15 sec of incubation and also recorded spectrophotometrically at 585 and 635 nm against air. The color varied with concentration. In 100 to 500 mg/L glucose solutions, the color varied from C100 to C500. At 100 to 500 mg/L glucose concentrations, OD 585 varied from 0.104 to 0.225 and OD 635 varied from 0.089 to 0.196. In the COD range of 106.7 to 533.5 mg/L the OD 585 and OD 635 there was an incremental difference of 0.030 and 0.028 for each 106.7 mg/L COD increase, respectively. Hence, for a preliminary estimate of COD value, color of the standard reaction mixture based on a range of glucose concentrations can be used as a reference. For samples, with initial COD concentration of 106.7 to 533.5 mg/L, OD 585 or OD 635 can be recorded for obtaining more accurate values.

TABLE 6

Correlation between COD concentration, color of the reaction mixture and their OD at different wave lengths.

| Glucose Concentration (mg/L) | COD of Glucose solution (mg/L) | Color of the reaction mixture | OD 585 nm of the reaction mixture | OD 635 nm of the reaction mixture |
|---|---|---|---|---|
| 100 | 106.7 | C100 | 0.104 | 0.089 |
| 200 | 213.4 | C200 | 0.132 | 0.115 |
| 300 | 320.1 | C300 | 0.164 | 0.145 |
| 400 | 426.8 | C400 | 0.196 | 0.165 |
| 500 | 533.5 | C500 | 0.225 | 0.196 |

EXAMPLE 7

Dissolved 0.3 g glucose in 50 ml distilled water. Aliquots from the stock solution were taken and diluted with water to achieve different concentrations in the range of 300 to 500 mg/L (COD: 320.1 to 533.5 mg/L). Weighed 0.02 g $HgSO_4$ in separate 15 mL test tubes. 1.0 ml of glucose sample was added to each test tube and shake well. 0.5 mL of $K_2Cr_2O_7$ was added to each sample. 1.5 mL $H_2SO_4$ silver sulphate reagent was added slowly with continuous shaking. The color of the reaction mixture was noted down visually within 15 sec of incubation and also recorded spectrophotometrically at 585 against air. The color varied with concentration. In 300 to 500 mg/L glucose solutions, the color varied from C300 to C500. At 300 to 500 mg/L glucose concentrations, OD 585 varied on an average from 0.158 to 0.210. In the COD range of 320.1 to 533.5 mg/L the OD 585 there was an incremental difference of 0.026 for each 106.7 mg/L COD increase. Hence, for a preliminary estimate of COD value, color of the standard reaction mixture based on a range of glucose concentrations can be used as a reference. For samples, with initial COD concentration of 320.1 to 533.5 mg/L, OD 585 can be recorded for obtaining values that are more precise.

TABLE 7

Correlation between COD concentration, color of the reaction mixture and their OD at 585 nm.

| S. No. | Glucose Concentration (mg/L) | COD of Glucose solution (mg/L) | Color of the reaction mixture | OD 585 nm of the reaction mixture |
|---|---|---|---|---|
| 1. | 300 | 320.1 | C300 | 0.154 |
| 2. | 300 | 320.1 | C300 | 0.168 |
| 3. | 300 | 320.1 | C300 | 0.162 |
| 4. | 300 | 320.1 | C300 | 0.155 |
| 5. | 300 | 320.1 | C300 | 0.153 |
| 6. | 300 | 320.1 | C300 | 0.158 |
| 7. | 300 | 320.1 | C300 | 0.157 |
| 1. | 400 | 426.8 | C400 | 0.178 |
| 2. | 400 | 426.8 | C400 | 0.207 |
| 3. | 400 | 426.8 | C400 | 0.189 |
| 4. | 400 | 426.8 | C400 | 0.183 |
| 5. | 400 | 426.8 | C400 | 0.181 |
| 6. | 400 | 426.8 | C400 | 0.185 |
| 7. | 400 | 426.8 | C400 | 0.186 |
| 1. | 500 | 533.5 | C500 | 0.193 |
| 2. | 500 | 533.5 | C500 | 0.234 |
| 3. | 500 | 533.5 | C500 | 0.207 |
| 4. | 500 | 533.5 | C500 | 0.215 |
| 5. | 500 | 533.5 | C500 | 0.207 |
| 6. | 500 | 533.5 | C500 | 0.208 |
| 7. | 500 | 533.5 | C500 | 0.210 |

EXAMPLE 8

Dissolved 0.5 g glucose in 100 mL distilled water. Aliquots from the stock solution were taken and diluted with water to achieve different COD concentrations in the range of 320 to 533 mg/L. A 20 mL sample of anaerobically digested damaged wheat grain slurry initially inoculated with *Aspergillus niger* for 10 days was taken. COD of the sample was estimated to be 52300 mg/L. (By Merck method and read on photometer.) Based on the estimated COD value, diluted samples were prepared in water to achieve a final COD in the range of 415 to 520 mg/L. Weighed 0.02 g $HgSO_4$ in separate 15 mL test tubes. 1.0 mL of glucose solution and sample were added to each test tube separately and mixed well. 0.5 mL of $K_2Cr_2O_7$ was added to each sample. 1.5 mL $H_2SO_4$ silver sulphate reagent was added slowly with continuous shaking. The color of the reaction mixture was noted down visually within 15 sec of incubation and also recorded spectrophotometrically at 585 and 635 nm against air. The color varied with concentration. In 320 to 533 mg/L glucose solutions, the color varied from C300 to C550. At 320 to 533 mg/L glucose concentrations, average OD 585 varied from 0.152 to 0.192 and OD 635 varied from 0.141 to 0.183. In the COD range of 320.1 to 533.5 mg/L the OD 585 and OD 635 there was an incremental difference of 0.026 and 0.024 for each 106.7 mg/L COD increase, respectively. On the other hand, color of the final sample reaction mixture varied from C400 to C500.

At 415.5 to 519.3 mg/L COD concentrations of the sample, average OD 585 varied from 0.145 to 0.169 and OD 635 varied from 0.129 to 0.148. In this COD range, there was an incremental difference of 0.024 and 0.020 for each 103.8 mg/L COD increase at OD 585 and OD 635, respectively.

Hence, for a preliminary estimate of COD value, color of the standard reaction mixture based on a range of glucose concentrations can be used as a reference. For samples, with COD concentration of 415.5 to 519.3 mg/L, OD 585 or OD 635 can be recorded for obtaining values that is more precise.

TABLE 8

Correlation between COD. concentration, color of the reaction mixture and their OD at different wave lengths.

| COD (mg/L) | Color of the reaction mixture | OD of the reaction mixture | |
|---|---|---|---|
| | | 585 nm | 635 nm |
| Glucose: | | | |
| 320 | C300 | 0.154 | 0.142 |
| | C300 | 0.150 | 0.139 |
| | C300 | 0.153 | 0.142 |
| 426 | C400 | 0.178 | 0.166 |
| | C400 | 0.175 | 0.162 |
| | C400 | 0.181 | 0.169 |
| 533 | C550 | 0.192 | 0.183 |
| | C550 | 0.190 | 0.180 |
| | C550 | 0.194 | 0.185 |
| Sample: Damaged wheat grain slurry | | | |
| 415.5 | C400 | 0.142 | 0.128 |
| | C400 | 0.152 | 0.132 |
| | C400 | 0.141 | 0.128 |
| 467.9 | C450 | 0.146 | 0.128 |
| | C450 | 0.149 | 0.135 |
| | C450 | 0.147 | 0.128 |
| 519.3 | C500 | 0.180 | 0.161 |
| | C500 | 0.166 | 0.140 |
| | C500 | 0.162 | 0.142 |

EXAMPLE 9

Dissolved 0.15 g glucose in 25 mL distilled water. Aliquots from the stock solution were taken and diluted with water to achieve different COD concentrations in the range of 320 to 533 mg/L. A 30 mL sample of anaerobically digested damaged wheat grain slurry initially inoculated with *Bacillus licheniformis* was taken. COD of the sample was estimated to be 54700 mg/L. (By Merck method and read on photometer.) Based on the estimated COD value, diluted samples were prepared in water to achieve a final COD in the range of 300 to 500 mg/L. Weighed 0.02 g $HgSO_4$ in separate 15 mL test tubes. 1.0 mL of glucose solution and sample were added to each test tube separately and mixed well. 0.5 mL of $K_2Cr_2O_7$ was added to each sample. 1.5 mL $H_2SO_4$ silver sulphate reagent was added slowly with continuous shaking. The color of the reaction mixture was noted down visually within 15 sec of incubation and also recorded spectrophotometrically at 585 and 635 nm against air. The color varied with concentration. In 320 to 533 mg/L glucose solutions, the color varied from C300 to C550. At 320 to 533 mg/L glucose concentrations, average OD 585 varied from 0.168 to 0.234 and OD 635 varied from 0.151 to 0.213. In the COD range of 320.1 to 533.5 mg/L the OD 585 and OD 635 there was an incremental difference of 0.033 for each 106.7 mg/L COD increase. On the other hand, color of the final sample reaction mixture varied from C300 to C550. At 300 to 500 mg/L COD concentrations of the sample, average OD 585 varied from 0.136 to 0.175 and OD 635 varied from 0.123 to 0.156. In this COD range, there was an incremental difference of 0.020 and 0.017 for each 100 mg/L COD increase at OD 585 and OD 635, respectively.

Hence, for a preliminary estimate of COD value, color of the standard reaction mixture based on a range of glucose concentrations can be used as a reference. For samples, with COD concentration of 300 to 500 mg/L, OD 585 or OD 635 can be recorded for obtaining values that is more precise.

TABLE 9

Correlation between COD concentration, color of the reaction mixture and their OD at different wave lengths.

| COD (mg/L) | Color of the reaction mixture | OD of the reaction mixture 585 nm | 635 nm |
|---|---|---|---|
| | Glucose: | | |
| 320 | C300 | 0.164 | 0.146 |
| | C300 | 0.167 | 0.152 |
| | C300 | 0.172 | 0.154 |
| 426 | C400 | 0.198 | 0.182 |
| | C400 | 0.214 | 0.194 |
| | C400 | 0.209 | 0.193 |
| 533 | C550 | 0.235 | 0.212 |
| | C550 | 0.236 | 0.217 |
| | C550 | 0.231 | 0.211 |
| | Sample: Damaged wheat grain slurry | | |
| 300.7 | C300 | 0.140 | 0.129 |
| | C300 | 0.135 | 0.121 |
| | C300 | 0.134 | 0.121 |
| 411.6 | C400 | 0.158 | 0.146 |
| | C400 | 0.156 | 0.140 |
| | C400 | 0.157 | 0.141 |
| 500.6 | C500 | 0.174 | 0.155 |
| | C500 | 0.175 | 0.160 |
| | C500 | 0.175 | 0.155 |

TABLE 10

Correlation between COD concentration, color of the reaction mixture and their OD at different wavelengths.

| COD (mg/L) | Color of the reaction mixture | OD of the reaction mixture 585 nm | 635 nm |
|---|---|---|---|
| | Glucose: | | |
| 320 | C300 | 0.160 | 0.143 |
| | C300 | 0.164 | 0.147 |
| | C300 | 0.162 | 0.145 |
| 426 | C400 | 0.190 | 0.184 |
| | C400 | 0.191 | 0.176 |
| | C400 | 0.187 | 0.168 |
| 533 | C550 | 0.207 | 0.190 |
| | C550 | 0.206 | 0.184 |
| | C550 | 0.207 | 0.185 |
| | Sample: Damaged wheat grain slurry | | |
| 337.1 | C350 | 0.128 | 0.112 |
| | C350 | 0.134 | 0.119 |
| | C350 | 0.135 | 0.117 |
| 421.3 | C400 | 0.153 | 0.135 |
| | C400 | 0.151 | 0.134 |
| | C400 | 0.155 | 0.137 |
| 504.6 | C500 | 0.168 | 0.149 |
| | C500 | 0.169 | 0.149 |
| | C500 | 0.169 | 0.154 |

EXAMPLE 10

Dissolved 0.2-g glucose in 50 mL distilled water. Aliquots from the stock solution were taken and diluted with water to achieve different COD concentrations in the range of 320 to 533 mg/L. A 25-mL sample of anaerobically digested damaged wheat grain slurry was taken. COD of the sample was estimated to be 61300 mg/L. (By Merck method and read on photometer.) Based on the estimated COD value, diluted samples were prepared in water to achieve a final COD in the range of 335 to 505 mg/L. Weighed 0.02 g $HgSO_4$ in separate 15-mL test tubes. 1.0 mL of glucose solution and sample were added to each test tube separately and mixed well. 0.5 mL of $K_2Cr_2O_7$ was added to each sample. 1.5 mL $H_2SO_4$ silver sulphate reagent was added slowly with continuous shaking. The color of the reaction mixture was noted down visually within 15 sec of incubation and recorded spectrophotometrically at 585 and 635 nm against air. The color varied with concentration. In 320 to 533 mg/L glucose solutions, the color varied from C300 to C550. At 320 to 533 mg/L glucose concentrations, average OD 585 varied from 0.162 to 0.207 and OD 635 varied from 0.145 to 0.186. In the COD range of 320.1 to 533.5 mg/L, the OD 585 and OD 635 there was an incremental difference of 0.023 and 0.025 for each 106.7 mg/L COD increase, respectively. On the other hand, color of the final sample reaction mixture varied from C350 to C500.

At 335 to 505 mg/L COD concentrations of the sample, average OD 585 varied from 0.132 to 0.169 and OD 635 varied from 0.116 to 0.151. In this COD range, there was an incremental difference of 0.019 and 0.022 for each 85 mg/L COD increase at OD 585 and OD 635, respectively.

Hence, for a preliminary estimate of COD value, color of the standard reaction mixture based on a range of glucose concentrations can be used as a reference. For samples, with COD concentration of 335 to 505 mg/L, OD 585 or OD 635 can be recorded for obtaining values that is more precise.

EXAMPLE 11

Dissolved 0.1 g glucose in 50 mL distilled water. Aliquots from the stock solution were taken and diluted with water to achieve different COD concentrations in the range of 320 to 533 mg/L. A 40-mL sample of anaerobically digested damaged wheat grain slurry initially treated with *Aspergillus niger* for 10 days and inoculated with *Bacillus subtilis* was taken. COD of the sample was estimated to be 6600 mg/L. (By Merck method and read on photometer.) Based on the estimated COD value, diluted samples were prepared in water to achieve a final COD in the range of 330 to 530 mg/L. Weighed 0.02 g $HgSO_4$ in separate 15-mL test tubes. 1.0 mL of glucose solution and sample were added to each test tube separately and mixed well. 0.5 mL of $K_2Cr_2O_7$ was added to each sample. 1.5 mL $H_2SO_4$ silver sulfate reagent was added slowly with continuous shaking. The color of the reaction mixture was noted down visually within 15 sec of incubation and recorded spectrophotometrically at 585 and 635 nm against air. The color varied with concentration. In 320 to 533 mg/L glucose solutions, the color varied from C300 to C550. At 320 to 533 mg/L glucose concentrations, average OD 585 varied from 0.155 to 0.215 and OD 635 varied from 0.144 to 0.194. In the COD range of 320.1 to 533.5 mg/L, the OD 585 and OD 635 there was an incremental difference of 0.030 and 0.025 for each 106.7-mg/L COD increase, respectively. On the other hand, color of the final sample reaction mixture varied from C350 to C550.

At 330 to 530 mg/L COD concentrations of the sample, average OD 585 varied from 0.137 to 0.174 and OD 635 varied from 0.121 to 0.153. In this COD range, there was an incremental difference of 0.019 and 0.016 for each 100-mg/L COD increase at OD 585 and OD 635, respectively.

Hence, for a preliminary estimate of COD value, color of the standard reaction mixture based on a range of glucose concentrations can be used as a reference. For samples, with COD concentration of 330 to 530 mg/L, OD 585 or OD 635 can be recorded for obtaining values that is more precise.

TABLE 11

Correlation between COD concentration, color of the reaction mixture and their OD at different wavelengths.

| COD (mg/L) | Color of the reaction mixture | OD of the reaction mixture 585 nm | 635 nm |
|---|---|---|---|
| | Glucose: | | |
| 320 | C300 | 0.154 | 0.143 |
| | C300 | 0.155 | 0.142 |
| | C300 | 0.157 | 0.146 |
| 426 | C400 | 0.182 | 0.170 |
| | C400 | 0.182 | 0.168 |
| | C400 | 0.184 | 0.170 |
| 533 | C550 | 0.206 | 0.187 |
| | C550 | 0.208 | 0.190 |
| | C550 | 0.230 | 0.205 |
| | Sample: Damaged wheat grain slurry | | |
| 331 | C350 | 0.134 | 0.118 |
| | C350 | 0.138 | 0.126 |
| | C350 | 0.138 | 0.120 |
| 429 | C400 | 0.157 | 0.139 |
| | C400 | 0.153 | 0.135 |
| | C400 | 0.154 | 0.134 |
| 529 | C500 | 0.172 | 0.152 |
| | C500 | 0.171 | 0.151 |
| | C500 | 0.178 | 0.156 |

TABLE 12

Correlation between COD concentration, color of the reaction mixture and their OD at different wave lengths.

| COD (mg/L) | Color of the reaction mixture | OD of the reaction mixture 585 nm | 635 nm |
|---|---|---|---|
| | Glucose: | | |
| 320 | C300 | 0.152 | 0.142 |
| | C300 | 0.156 | 0.145 |
| | C300 | 0.151 | 0.139 |
| 426 | C400 | 0.181 | 0.169 |
| | C400 | 0.183 | 0.170 |
| | C400 | 0.180 | 0.168 |
| 533 | C550 | 0.205 | 0.186 |
| | C550 | 0.212 | 0.194 |
| | C550 | 0.204 | 0.184 |
| | Sample: Vegetable waste slurry | | |
| 290 | C300 | 0.140 | 0.123 |
| | C300 | 0.132 | 0.120 |
| | C300 | 0.141 | 0.127 |
| 386 | C400 | 0.158 | 0.143 |
| | C400 | 0.151 | 0.140 |
| | C400 | 0.144 | 0.128 |
| 482 | C500 | 0.162 | 0.146 |
| | C500 | 0.156 | 0.141 |
| | C500 | 0.153 | 0.137 |

EXAMPLE 12

Dissolved 0.2 g glucose in 50 mL distilled water. Aliquots from the stock solution were taken and diluted with water to achieve different COD concentrations in the range of 320 to 533 mg/L. A 30 mL sample of partially digested vegetable waste slurry was taken. COD of the sample was estimated to be 9640 mg/L (By Merck method and read on photometer). Based on the estimated COD value, diluted samples were prepared in water to achieve a final COD in the range of 290 to 480 mg/L. Weighed 0.02 g $HgSO_4$ in separate 15-mL test tubes. 1.0 mL of glucose solution and sample were added to each test tube separately and mixed well. 0.5 mL of $K_2Cr_2O_7$ was added to each sample. 1.5 mL $H_2SO_4$ silver sulfate reagent was added slowly with continuous shaking. The color of the reaction mixture was noted down visually within 15 sec of incubation and also recorded spectrophotometrically at 585 and 635 nm against air. The color varied with concentration. In 320 to 533 mg/L glucose solutions, the color varied from C300 to C550. At 320 to 533 mg/L glucose concentrations, average OD 585 varied from 0.153 to 0.207 and OD 635 varied from 0.142 to 0.188. In the COD range of 320.1 to 533.5 mg/L the OD 585 and OD 635 there was an incremental difference of 0.027 and 0.023 for each 106.7 mg/L COD increase, respectively. On the other hand, color of the final sample reaction mixture varied from C300 to C500.

At 290 to 480 mg/L COD concentrations of the sample, average OD 585 varied from 0.138 to 0.157 and OD 635 varied from 0.123 to 0.141. In this COD range, there was an incremental difference of 0.009 for each 95 mg/L COD increase at OD 585 and OD 635.

Hence, for a preliminary estimate of COD value, color of the standard reaction mixture based on a range of glucose concentrations can be used as a reference. For samples, with COD concentration of 290 to 480 mg/L, OD 585 or OD 635 can be recorded for obtaining values that is more accurate.

EXAMPLE 13

Dissolved 0.25 g glucose in 50 mL distilled water. Aliquots from the stock solution were taken and diluted with water to achieve different COD concentrations in the range of 320 to 533 mg/L. A 50 mL sample of partially digested vegetable waste slurry was mixed with anaerobically digested damaged wheat grain slurry. COD of the sample was estimated to be 9400 mg/L (By Merck method and read on photometer). Based on the estimated COD value, diluted samples were prepared in water to achieve a final COD in the range of 297 to 533 mg/L. Weighed 0.02 g $HgSO_4$ in separate 15 mL test tubes. 1.0 mL of glucose solution and sample were added to each test tube separately and mixed well. 0.5 mL of $K_2Cr_2O_7$ was added to each sample. 1.5 mL $H_2SO_4$ silver sulphate reagent was added slowly with continuous shaking. The color of the reaction mixture was noted down visually within 15 sec of incubation and also recorded spectrophotometrically at 585 and 635 nm against air. The color varied with concentration. In 320 to 533 mg/L glucose solutions, the color varied from C300 to C500. At 320 to 533 mg/L glucose concentrations, average OD 585 varied from 0.158 to 0.208 and OD 635 varied from 0.138 to 0.187. In the COD range of 320.1 to 533.5 mg/L the OD 585 and OD 635 there was an incremental difference of 0.025 and 0.025 for each 106.7 mg/L COD increase, respectively. On the other hand, color of the final sample reaction mixture varied from C300 to C500.

At 297 to 533 mg/L COD concentrations of the sample, average OD 585 varied from 0.132 to 0.179 and OD 635 varied from 0.118 to 0.162. In this COD range, there was an incremental difference of 0.023 and 0.027 for each 118 mg/L COD increase at OD 585 and OD 635, respectively.

Hence, for a preliminary estimate of COD value, color of the standard reaction mixture based on a range of glucose concentrations can be used as a reference. For samples, with COD concentration of 297 to 533 mg/L, OD 585 or OD 635 can be recorded for obtaining more precise values.

TABLE 13

Correlation between COD concentration, color of the reaction mixture and their OD at different wave lengths.

| COD (mg/L) | Color of the reaction mixture | OD of the reaction mixture 585 nm | 635 nm |
|---|---|---|---|
| | Glucose: | | |
| 320 | C300 | 0.167 | 0.148 |
| | C300 | 0.154 | 0.135 |
| | C300 | 0.152 | 0.131 |
| 426 | C400 | 0.188 | 0.167 |
| | C400 | 0.185 | 0.162 |
| | C400 | 0.181 | 0.159 |
| 533 | C550 | 0.215 | 0.195 |
| | C550 | 0.206 | 0.184 |
| | C550 | 0.202 | 0.181 |
| Sample: Vegetable waste slurry + Damaged wheat grain slurry | | | |
| 297 | C300 | 0.126 | 0.111 |
| | C300 | 0.138 | 0.124 |
| | C300 | 0.133 | 0.118 |
| 445 | C450 | 0.168 | 0.152 |
| | C450 | 0.164 | 0.148 |
| | C450 | 0.168 | 0.152 |
| 533 | C550 | 0.188 | 0.169 |
| | C550 | 0.180 | 0.163 |
| | C550 | 0.169 | 0.153 |

TABLE 14

Correlation between COD concentration, color of the reaction mixture and their OD at different wave lengths.

| COD (mg/L) | Color of the reaction mixture | OD of the reaction mixture 585 nm | 635 nm |
|---|---|---|---|
| | Glucose: | | |
| 320 | C300 | 0.157 | 0.142 |
| | C300 | 0.154 | 0.139 |
| | C300 | 0.159 | 0.146 |
| 426 | C400 | 0.186 | 0.168 |
| | C400 | 0.185 | 0.162 |
| | C400 | 0.187 | 0.170 |
| 533 | C550 | 0.216 | 0.196 |
| | C550 | 0.209 | 0.188 |
| | C550 | 0.207 | 0.183 |
| Sample: Apple pomace | | | |
| 310 | C300 | 0.140 | 0.126 |
| | C300 | 0.142 | 0.126 |
| | C300 | 0.140 | 0.126 |
| 413 | C400 | 0.171 | 0.152 |
| | C400 | 0.165 | 0.148 |
| | C400 | 0.165 | 0.147 |
| 517 | C500 | 0.186 | 0.166 |
| | C500 | 0.187 | 0.168 |
| | C500 | 0.186 | 0.167 |

EXAMPLE 14

Dissolved 0.15 g glucose in 50 mL distilled water. Aliquots from the stock solution were taken and diluted with water to achieve different COD concentrations in the range of 320 to 533 mg/L. A 30 mL sample of apple pomace soaked for 1 day was taken. COD of the sample was estimated to be 51700 mg/L (By Merck method and read on photometer). Based on the estimated COD value, diluted samples were prepared in water to achieve a final COD in the range of 310 to 517 mg/L. Weighed 0.02 g $HgSO_4$ in separate 15 mL test tubes. 1.0 mL of glucose solution and sample were added to each test tube separately and mixed well. 0.5 ml of $K_2Cr_2O_7$ was added to each sample. 1.5 mL $H_2SO_4$ silver sulphate reagent was added slowly with continuous shaking. The color of the reaction mixture was noted down visually within 15 sec of incubation and also recorded spectrophotometrically at 585 and 635 nm against air. The color varied with concentration. In 320 to 533 mg/L glucose solutions, the color varied from C300 to C550. At 320 to 533 mg/L glucose concentrations, average OD 585 varied from 0.157 to 0.210 and OD 635 varied from 0.142 to 0.189. In the COD range of 320.1 to 533.5 mg/L the OD 585 and OD 635 there was an incremental difference of 0.026 and 0.024 for each 106.7 mg/L COD increase, respectively. On the other hand, color of the final sample reaction mixture varied from C300 to C500.

At 310 to 517 mg/L COD concentrations of the sample, average OD 585 varied from 0.141 to 0.186 and OD 635 varied from 0.126 to 0.167. In this COD range, there was an incremental difference of 0.022 and 0.020 for each 104 mg/L COD increase at OD 585 and OD 635, respectively.

Hence for a preliminary estimate of COD value, color of the standard reaction mixture based on a range of glucose concentrations can be used as a reference. For samples, with COD concentration of 310 to 517 mg/L, OD 585 or OD 635 can be recorded for obtaining more precise values.

EXAMPLE 15

Dissolved 0.1 g glucose in 50 mL distilled water. Aliquots from the stock solution were taken and diluted with water to achieve different concentrations in the range of 320 to 533 mg/L. A 50 mL sample was prepared by mixing apple pomace soaked for 1 day with digested damaged wheat grains and partially digested vegetable market waste. COD of the sample was estimated to be 40300 mg/L (By Merck method and read on photometer). Based on the estimated COD value, diluted samples were prepared in water to achieve a final COD in the range of 310 to 497 mg/L. Weighed 0.02 g $HgSO_4$ in separate 15 mL test tubes. 1.0 mL of glucose solution and sample were added to each test tube separately and mixed well. 0.5 ml of $K_2Cr_2O_7$ was added to each sample. 1.5 mL $H_2SO_4$ silver sulphate reagent was added slowly with continuous shaking. The color of the reaction mixture was noted down visually within 15 sec of incubation and also recorded spectrophotometrically at 585 and 635 nm against air. The color varied with concentration. In 320 to 533 mg/L glucose solutions, the color varied from C300 to C550. At 320 to 533 mg/L glucose concentrations, average OD 585 varied from 0.159 to 0.212 and OD 635 varied from 0.142 to 0.190. In the COD range of 320.1 to 533.5 mg/L the OD 585 and OD 635 there was an incremental difference of 0.026 and 0.024 for each 106.7 mg/L COD increase, respectively. On the other hand, color of the final sample reaction mixture varied from C300 to C500.

At 310 to 497 mg/L COD concentrations of the sample, average OD 585 varied from 0.125 to 0.169 and OD 635 varied from 0.112 to 0.155. In this COD range, there was an incremental difference of 0.022 and 0.021 for each 93 mg/L COD increase at OD 585 and OD 635, respectively.

Hence for a preliminary estimate of COD value, color of the standard reaction mixture based on a range of glucose concentrations can be used as a reference. For samples, with COD concentration of 310 to 497 mg/L, OD 585 or OD 635 can be recorded for obtaining more precise values.

TABLE 15

Correlation between COD concentration, color of the reaction mixture and their OD at different wave lengths.

| COD (mg/L) | Color of the reaction mixture | OD of the reaction mixture | |
|---|---|---|---|
| | | 585 nm | 635 nm |
| Glucose: | | | |
| 320 | C300 | 0.160 | 0.144 |
| | C300 | 0.157 | 0.141 |
| | C300 | 0.159 | 0.142 |
| 426 | C400 | 0.187 | 0.170 |
| | C400 | 0.185 | 0.167 |
| | C400 | 0.189 | 0.172 |
| 535 | C550 | 0.220 | 0.199 |
| | C550 | 0.209 | 0.187 |
| | C550 | 0.207 | 0.184 |
| Sample Apple pomace + Vegetable waste slurry + Damaged wheat grain slurry | | | |
| 310 | C300 | 0.126 | 0.114 |
| | C300 | 0.126 | 0.112 |
| | C300 | 0.124 | 0.111 |
| 404 | C400 | 0.148 | 0.136 |
| | C400 | 0.154 | 0.146 |
| | C400 | 0.152 | 0.141 |
| 497 | C500 | 0.171 | 0.159 |
| | C500 | 0.168 | 0.154 |
| | C500 | 0.167 | 0.152 |

EXAMPLE 16

Dissolved 0.15 g glucose in 25 mL distilled water. Aliquots from the stock solution were taken and diluted with water to achieve different COD concentrations in the range of 320 to 535 mg/L. A 30 mL sample of partially digested vegetable waste slurry mixed with potassium hydrogen phosphate salt was taken. Weighed 0.02 g $HgSO_4$ in separate 15 mL test tubes. 1.0 mL of glucose solution and sample were added to each test tube separately and mixed well. 0.5 mL of $K_2Cr_2O_7$ was added to each sample. 1.5 mL $H_2SO_4$ silver sulphate reagent was added slowly with continuous shaking. The color of the reaction mixture was noted down visually within 15 sec of incubation and also recorded spectrophotometrically at 585 and 635 nm against air. An approximate COD value of the sample was estimated from the color of standard reaction mixture prepared with glucose as reference material in the COD range of 200 to 100000 mg/L. OD 585 and OD 635 of the reaction mixture was read spectrophotometrically OD 585 and 635 nm in the range of 0.130 to 0.175 and 0.120 to 0.160 respectively were considered and calculated with reference to glucose standard. (Glucose COD in the range of 320 to 535 mg/L corresponds to OD 585 and 635 nm in the range of 0.157 to 0.207 and 0.142 to 0.189, respectively). COD of the sample was estimated to be 777 mg/L. (By Merck method and read on photometer).

Based on the color of the reaction mixture, COD of the sample was estimated to be around 750 mg/L. On the basis of the dilution method and the spectrophotometric reading at OD 585 and OD 635 of the sample, COD was estimated to be 824 and 852 mg/L, respectively. A comparison with the COD value calculated through Merck method reveals the following relation i.e. Our COD value (at OD 585)×0.94= COD value (Merck Method) or our COD value (at OD 635)×0.91=COD value (Merck Method).

Hence for a preliminary estimate of COD value, color of the standard reaction mixture based on a range of glucose concentrations can be used as a reference. For samples, with COD concentration of 300 to 500 mg/L, OD 585 or OD 635 can be recorded for obtaining more precise values.

TABLE 16

Correlation between COD concentration, color of the reaction mixture and their OD at different wave lengths.

| COD (mg/L) | Sample dilution (Times) | Color of the reaction mixture | OD | Estimated COD (mg/L) | Estimated final COD (mg/L) (Col. 2 × 5) |
|---|---|---|---|---|---|
| 1 | 2 | 3 | 4 | 5 | 6 |
| Values at OD 585 nm | | | | | |
| Glucose: | | | | | |
| 320 | NA | C300 | 0.162 | NA | NA |
| 426 | NA | C400 | 0.186 | NA | NA |
| 535 | NA | C550 | 0.206 | NA | NA |
| Sample: Vegetable waste (filtrate) + Potassium hydrogen phosphate | | | | | |
| | Nil | C1500 | 0.240 | ≅1500# | ≅1500 |
| | 5 | C150 | 0.101 | 150# | 750 |
| | 2 | C400 | 0.150 | 412 | 824 |
| Values at OD 635 nm | | | | | |
| Glucose: | | | | | |
| 320 | NA | C300 | 0.150 | NA | NA |
| 426 | NA | C400 | 0.167 | NA | NA |
| 535 | NA | C550 | 0.187 | NA | NA |
| Sample: Vegetable waste (filtrate) + Potassium hydrogen phosphate | | | | | |
| | Nil | C1500 | 0.40 | ≅1500# | ≅1500 |
| | 5 | C150 | 0.101 | 150# | 750 |
| | 2 | C400 | 0.150 | 426 | 852 |

COD as deducible from Table 2 given in Example 2.
D: Dark.
T: Turbid.
*OD out of range.
NA: Not applicable.
Samples are diluted to get an OD 585 in the range of 0.130 to 0.175 and OD 635 in the range of 0.120 to 0.160, to obtain a COD value in the range of 320 to 535 mg/L. (Based on the Tables 3 to 15 given in Examples 3 to 15).

EXAMPLE 17

Dissolved 0.15 g glucose in 25 mL distilled water. Aliquots from the stock solution were taken and diluted with water to achieve different COD concentrations in the range of 320 to 535 mg/L. A 30 mL sample of partially digested palm oil mill effluent (filtrate) was taken. Weighed 0.02 g $HgSO_4$ in separate 15 mL test tubes. 1.0 mL of glucose solution and sample were added to each test tube separately and mixed well. 0.5 mL of $K_2Cr_2O_7$ was added to each sample. 1.5 mL $H_2SO_4$ silver sulphate reagent was added slowly with continuous shaking. The color of the reaction mixture was noted down visually within 15 sec of incubation and also recorded spectrophotometrically at 585 and 635 nm against air. An approximate COD value of the sample was estimated from the color of standard reaction mixture prepared with glucose as reference material in the COD range of 200 to 100000 mg/L. OD 585 and OD 635 of the reaction mixture was read spectrophotometrically. OD 585 and 635 nm in the range of 0.130 to 0.175 and 0.120 to 0.160 respectively were considered and calculated with reference to glucose standard. (Glucose COD in the range of 320 to 535 mg/L corresponds to OD 585 and 635 nm in the range of 0.159 to 0.205 and 0.149 to 0.183, respectively).

COD of the sample was estimated to be 687 mg/L. (By Merck method and read on photometer).

Based on the color of the reaction mixture, COD of the sample was estimated to be around 500 mg/L. On the basis of the dilution method and the spectrophotometric reading at OD 585 and OD 635 of the sample, COD was estimated to be 874 and 882 mg/L, respectively. A comparison with the COD value calculated through Merck method reveals the following relation i.e. Our COD value (at OD 585)×0.79= COD value (Merck Method) or our COD value (at OD 635)×0.79=COD value (Merck Method).

Hence for a preliminary estimate of COD value, color of the standard reaction mixture based on a range of glucose concentrations can be used as a reference. For samples, with COD concentration of 300 to 500 mg/L, OD 585 or OD 635 can be recorded for obtaining more precise values.

TABLE 17

Correlation between COD concentration, color of the reaction mixture and their OD at different wave lengths.

| COD (mg/L) 1 | Sample dilution (Times) 2 | Color of the reaction mixture 3 | OD 4 | Estimated COD (mg/L) 5 | Estimated final COD (mg/L) (Col. 2 × 5) 6 |
|---|---|---|---|---|---|
| Values at OD 585 nm | | | | | |
| Glucose: | | | | | |
| 320 | NA | C300 | 0.159 | NA | NA |
| 426 | NA | C400 | 0.186 | NA | NA |
| 535 | NA | C550 | 0.205 | NA | NA |
| Sample: Palm oil mill effluent (filtrate) | | | | | |
| | Nil | C500 | 0.236 | ≅500# | ≅500 |
| | 2 | C450 | 0.159 | 437 | 874 |
| Values at OD 635 nm | | | | | |
| Glucose: | | | | | |
| 320 | NA | C300 | 0.149 | NA | NA |
| 426 | NA | C400 | 0.166 | NA | NA |
| 535 | NA | C550 | 0.183 | NA | NA |
| Sample: Palm oil mill effluent (filtrate) | | | | | |
| | Nil | C500 | 0.213 | ≅500# | ≅500 |
| | 2 | C450 | 0.143 | 441 | 882 |

COD as deducible from Table 2 given in Example 2.
D: Dark.
T: Turbid.
*OD out of range.
NA: Not applicable.
Samples are diluted to get an OD 585 in the range of 0.130 to 0.175 and OD 635 in the range of 0.120 to 0.160, to obtain a COD value in the range of 320 to 535 mg/L. (Based on the Tables 3 to 15 given in Examples 3 to 15).

EXAMPLE 18

Dissolved 0.15 g glucose in 25 mL distilled water. Aliquots from the stock solution were taken and diluted with water to achieve different COD concentrations in the range of 320 to 535 mg/L. A 30 mL sample of partially digested vegetable waste slurry mixed was taken. Weighed 0.02 g $HgSO_4$ in separate 15 mL test tubes. 1.0 mL of glucose solution and sample were added to each test tube separately and mixed well. 0.5 mL of $K_2Cr_2O_7$ was added to each sample. 1.5 mL $H_2SO_4$ silver sulphate reagent was added slowly with continuous shaking. The color of the reaction mixture was noted down visually within 15 sec of incubation and also recorded spectrophotometrically at 585 and 635 nm against air. An approximate COD value of the sample was estimated from the color of standard reaction mixture prepared with glucose as reference material in the COD range of 200 to 100000 mg/L. OD 585 and OD 635 of the reaction mixture was read spectrophotometrically. OD 585 and 635 nm in the range of 0.130 to 0.175 and 0.120 to 0.160 respectively were considered and calculated with reference to glucose standard. (Glucose COD in the range of 320 to 535 mg/L corresponds to OD 585 and 635 nm in the range of 0.157 to 0.207 and 0.142 to 0.189, respectively).

COD of the sample was estimated to be 1930 mg/L. (By Merck method and read on photometer).

Based on the color of the reaction mixture, COD of the sample was estimated to be around 1400 mg/L. On the basis of the dilution method and the spectrophotometric reading at OD 585 and OD 635 of the sample, COD was estimated to be 1280 and 1288 mg/L, respectively. A comparison with the COD value calculated through Merck method reveals the following relation i.e. Our COD value (at OD 585)×1.51= COD value (Merck Method) or our COD value (at OD 635)×1.50=COD value (Merck Method).

Hence for a preliminary estimate of COD value, color of the standard reaction mixture based on a range of glucose concentrations can be used as a reference. For samples, with COD concentration of 300 to 500 mg/L, OD 585 or OD 635 can be recorded for obtaining more precise values.

TABLE 18

Correlation between COD concentration, color of the reaction mixture and their OD at different wave lengths.

| COD (mg/L) 1 | Sample dilution (Times) 2 | Color of the reaction mixture 3 | OD 4 | Estimated COD (mg/L) 5 | Estimated final COD (mg/L) (Col. 2 × 5) 6 |
|---|---|---|---|---|---|
| Values at OD 585 nm | | | | | |
| Glucose: | | | | | |
| 320 | NA | C300 | 0.161 | NA | NA |
| 426 | NA | C400 | 0.187 | NA | NA |
| 535 | NA | C550 | 0.202 | NA | NA |
| Sample: Vegetable waste slurry | | | | | |
| | Nil | C1400 | 0.294 | ≅1400# | ≅1400 |
| | 4 | C320 | 0.134 | 320 | 1280 |
| Values at OD 635 nm | | | | | |
| Glucose: | | | | | |
| 320 | NA | C300 | 0.144 | NA | NA |
| 426 | NA | C400 | 0.167 | NA | NA |
| 535 | NA | C550 | 0.184 | NA | NA |
| Sample: Vegetable waste slurry | | | | | |
| | Nil | C1400 | 0.268 | ≅1400# | ≅1400 |
| | 4 | C320 | 0.121 | 322 | 1288 |

COD as deducible from Table 2 given in Example 2.
D: Dark.
T: Turbid.
*OD out of range.
NA: Not applicable.
Samples are diluted to get an OD 585 in the range of 0.130 to 0.175 and OD 635 in the range of 0.120 to 0.160, to obtain a COD value in the range of 320 to 535 mg/L. (Based on the Tables 4 to 15 given in Examples 4 to 15.

EXAMPLE 19

Dissolved 0.15 g glucose in 25 mL distilled water. Aliquots from the stock solution were taken and diluted with water to achieve different COD concentrations in the range of 320 to 535 mg/L. A 30 mL sample of partially digested Vegetable waste slurry (filtrate) mixed was taken. Weighed 0.02 g $HgSO_4$ in separate 15 mL test tubes. 1.0 mL of glucose solution and sample were added to each test tube separately and mixed well. 0.5 mL of $K_2Cr_2O_7$ was added to each sample. 1.5 mL $H_2SO_4$ silver sulphate reagent was added slowly with continuous shaking. The color of the reaction mixture was noted down visually within 15 sec of incubation and also recorded spectrophotometrically at 585 and 635 nm against air. An approximate COD value of the sample was estimated from the color of standard reaction mixture prepared with glucose as reference material in the COD range of 200 to 100000 mg/L. OD 585 and OD 635 of the reaction mixture was read spectrophotometrically. OD 585 and 635 nm in the range of 0.130 to 0.175 and 0.120 to 0.160 respectively were considered and calculated with reference to glucose standard. (Glucose COD in the range of 320 to 535 mg/L corresponds to OD 585 and 635 nm in the range of 0.157 to 0.207 and 0.142 to 0.189, respectively).

COD of the sample was estimated to be 1033 mg/L. (By Merck method and read on photometer).

Based on the color of the reaction mixture, COD of the sample was estimated to be around 1500 mg/L. On the basis of the dilution method and the spectrophotometric reading at OD 585 and OD 635 of the sample, COD was estimated to be 1632 and 1652 mg/L, respectively. A comparison with the COD value calculated through Merck method reveals the following relation i.e. Our COD value (at OD 585)×0.63= COD value (Merck Method) or our COD value (at OD 635)×0.62=COD value (Merck Method).

Hence for a preliminary estimate of COD value, color of the standard reaction mixture based on a range of glucose concentrations can be used as a reference. For samples, with COD concentration of 300 to 500 mg/L, OD 585 or OD 635 can be recorded for obtaining more precise values.

TABLE 19

Correlation between COD concentration, color of the reaction mixture and their OD at different wave lengths.

| COD (mg/L) 1 | Sample dilution (Times) 2 | Color of the reaction mixture 3 | OD 4 | Estimated COD (mg/L) 5 | Estimated final COD (mg/L) (Col. 2 × 5) 6 |
|---|---|---|---|---|---|
| Values at OD 585 nm | | | | | |
| Glucose: | | | | | |
| 320 | NA | C300 | 0.159 | NA | NA |
| 426 | NA | C400 | 0.186 | NA | NA |
| 535 | NA | C550 | 0.205 | NA | NA |
| Sample: Vegetable waste slurry (filtrate) | | | | | |
| | Nil | C1500 | 0.257 | ≅1500# | ≅1500 |
| | 4 | C400 | 0.148 | 408 | 1632 |
| Values at OD 635 nm | | | | | |
| Glucose: | | | | | |
| 320 | NA | C300 | 0.145 | NA | NA |
| 426 | NA | C400 | 0.166 | NA | NA |
| 535 | NA | C550 | 0.187 | NA | NA |

TABLE 19-continued

Correlation between COD concentration, color of the reaction mixture and their OD at different wave lengths.

| COD (mg/L) 1 | Sample dilution (Times) 2 | Color of the reaction mixture 3 | OD 4 | Estimated COD (mg/L) 5 | Estimated final COD (mg/L) (Col. 2 × 5) 6 |
|---|---|---|---|---|---|
| Sample: Vegetable waste slurry (filtrate) | | | | | |
| | Nil | C1500 | 0.236 | ≅1500# | ≅1500 |
| | 4 | C400 | 0.134 | 413 | 1652 |

COD as deducible from Table 2 given in Example 2.
D: Dark.
T: Turbid.
*OD out of range.
NA: Not applicable.
Samples are diluted to get an OD 585 in the range of 0.130 to 0.175 and OD 635 in the range of 0.120 to 0.160, to obtain a COD value in the range of 320 to 535 mg/L. (Based on the Tables 3 to 15 given in Examples 3 to 15).

EXAMPLE 20

Dissolved 0.15 g glucose in 25 mL distilled water. Aliquots from the stock solution were taken and diluted with water to achieve different COD concentrations in the range of 320 to 535 mg/L. A 30 mL sample of Damaged wheat grain (filtrate) mixed with vegetable waste slurry (filtrate) was taken. Weighed 0.02 g $HgSO_4$ in separate 15 mL test tubes. 1.0 mL of glucose solution and sample were added to each test tube separately and mixed well. 0.5 mL of $K_2Cr_2O_7$ was added to each sample. 1.5 mL $H_2SO_4$ silver sulphate reagent was added slowly with continuous shaking. The color of the reaction mixture was noted down visually within 15 sec of incubation and also recorded spectrophotometrically at 585 and 635 nm against air. An approximate COD value of the sample was estimated from the color of standard reaction mixture prepared with glucose as reference material in the COD range of 200 to 100000 mg/L. OD 585 and OD 635 of the reaction mixture was read spectrophotometrically. OD 585 and 635 nm in the range of 0.130 to 0.175 and 0.120 to 0.160 respectively were considered and calculated with reference to glucose standard. (Glucose COD in the range of 320 to 535 mg/L corresponds to OD 585 and 635 nm in the range of 0.157 to 0.207 and 0.142 to 0.189, respectively).

COD of the sample was estimated to be 4067 mg/L. (By Merck method and read on photometer).

Based on the color of the reaction mixture, COD of the sample was estimated to be around 3000 mg/L. On the basis of the dilution method and the spectrophotometric reading at OD 585 and OD 635 of the sample, COD was estimated to be 4170 and 4180 mg/L, respectively. A comparison with the COD value calculated through Merck method reveals the following relation i.e. Our COD value (at OD 585)×0.97= COD value (Merck Method) or our COD value (at OD 635)×0.97=COD value (Merck Method).

Hence for a preliminary estimate of COD value, color of the standard reaction mixture based on a range of glucose concentrations can be used as a reference. For samples, with COD concentration of 300 to 500 mg/L, OD 585 or OD 635 can be recorded for obtaining more precise values.

TABLE 20

Correlation between COD concentration, color of the reaction mixture and their OD at different wave lengths.

| COD (mg/L) 1 | Sample dilution (Times) 2 | Color of the reaction mixture 3 | OD 4 | Estimated COD (mg/L) 5 | Estimated final COD (mg/L) (Col. 2 × 5) 6 |
|---|---|---|---|---|---|
| \multicolumn{6}{c}{Values at OD 585 nm} | | | | | |
| Glucose: | | | | | |
| 320 | NA | C300 | 0.161 | NA | NA |
| 426 | NA | C400 | 0.186 | NA | NA |
| 535 | NA | C550 | 0.206 | NA | NA |
| Sample: Damaged wheat grain (filtrate) + Vegetable waste slurry (filtrate) | | | | | |
| Nil | C1400 | 1.031 | ≅1400# | ≅1400 | |
| 5 | C600 | 0.234 | ≅600# | ≅3000 | |
| 10 | C400 | 0.152 | 417 | 4170 | |
| Values at OD 635 nm | | | | | |
| Glucose: | | | | | |
| 320 | NA | C300 | 0.146 | NA | NA |
| 426 | NA | C400 | 0.167 | NA | NA |
| 535 | NA | C550 | 0.186 | NA | NA |
| Sample: Damaged wheat grain (filtrate) + Vegetable waste slurry (filtrate) | | | | | |
| Nil | C1400 | 0.784 | ≅1400# | ≅1400 | |
| 5 | C600 | 0.213 | ≅600# | ≅3000 | |
| 10 | C400 | 0.137 | 418 | 4180 | |

COD as deducible from Table 2 given in Example 2.
D: Dark.
T: Turbid.
*OD out of range.
NA: Not applicable.
Samples are diluted to get an OD 585 in the range of 0.130 to 0.175 and OD 635 in the range of 0.120 to 0.160, to obtain a COD value in the range of 320 to 535 mg/L. (Based on the Tables 3 to 15 given in Examples 3 to 15).

EXAMPLE 21

Dissolved 0.15 g glucose in 25 mL distilled water. Aliquots from the stock solution were taken and diluted with water to achieve different COD concentrations in the range of 320 to 535 mg/L. A 30 mL sample of Damaged wheat grain (filtrate) mixed with vegetable waste slurry was taken. Weighed 0.02 g $HgSO_4$ in separate 15 mL test tubes. 1.0 mL of glucose solution and sample were added to each test tube separately and mixed well. 0.5 ml of $K_2Cr_2O_7$ was added to each sample. 1.5 mL $H_2SO_4$ silver sulphate reagent was added slowly with continuous shaking. The color of the reaction mixture was noted down visually within 15 sec of incubation and also recorded spectrophotometrically at 585 and 635 nm against air. An approximate COD value of the sample was estimated from the color of standard reaction mixture prepared with glucose as reference material in the COD range of 200 to 100000 mg/L. OD 585 and OD 635 of the reaction mixture was read spectrophotometrically. OD 585 and 635 nm in the range of 0.130 to 0.175 and 0.120 to 0.160 respectively were considered and calculated with reference to glucose standard. (Glucose COD in the range of 320 to 535 mg/l corresponds to OD 585 and 635 nm in the range of 0.157 to 0.207 and 0.142 to 0.189, respectively).

COD of the sample was estimated to be 4059 mg/L. (By Merck method and read on photometer).

Based on the color of the reaction mixture, COD of the sample was estimated to be around 2900 mg/L. On the basis of the dilution method and the spectrophotometric reading at OD 585 and OD 635 of the sample, COD was estimated to be 4440 and 4490 mg/L, respectively. A comparison with the COD value calculated through Merck method reveals the following relation i.e. Our COD value (at OD 585)×0.91= COD value (Merck Method) or our COD value (at OD 635)×0.90=COD value (Merck Method).

Hence for a preliminary estimate of COD value, color of the standard reaction mixture based on a range of glucose concentrations can be used as a reference. For samples, with COD concentration of 300 to 500 mg/L, OD 585 or OD 635 can be recorded for obtaining more precise values.

TABLE 21

Correlation between COD concentration, color of the reaction mixture and their OD at different wave lengths.

| COD (mg/L) 1 | Sample dilution (Times) 2 | Color of the reaction mixture 3 | OD 4 | Estimated COD (mg/L) 5 | Estimated final COD (mg/L) (Col. 2 × 5) 6 |
|---|---|---|---|---|---|
| Values at OD 585 nm | | | | | |
| Glucose: | | | | | |
| 320 | NA | C300 | 0.159 | NA | NA |
| 426 | NA | C400 | 0.186 | NA | NA |
| 535 | NA | C300 | 0.205 | NA | NA |
| Sample: Damaged wheat grain (filtrate) + Vegetable waste | | | | | |
| Nil | C2000 | 0.438 | ≅2000# | ≅2000 | |
| 5 | C600 | 0.229 | ≅580# | ≅2900 | |
| 10 | C450 | 0.162 | 444 | 4440 | |
| Values at OD 635 nm | | | | | |
| Glucose: | | | | | |
| 320 | NA | C300 | 0.145 | NA | NA |
| 426 | NA | C400 | 0.166 | NA | NA |
| 535 | NA | C550 | 0.187 | NA | NA |
| Sample: Damaged wheat grain (filtrate) + Vegetable waste | | | | | |
| Nil | C2000 | 0.378 | ≅2000# | ≅2000 | |
| 5 | C600 | 0.206 | ≅580# | ≅2900 | |
| 10 | C450 | 0.146 | 449 | 4490 | |

COD as deducible from Table 2 given in Example 2.
D: Dark.
T: Turbid.
*OD out of range.
NA: Not applicable.
Samples are diluted to get an OD 585 in the range of 0.130 to 0.175 and OD 635 in the range of 0.120 to 0.160, to obtain a COD value in the range of 320 to 535 mg/L. (Based on the Tables 3 to 15 given in Examples 3 to 15).

EXAMPLE 22

Dissolved 0.15 g glucose in 25 mL distilled water. Aliquots from the stock solution were taken and diluted with water to achieve different COD concentrations in the range of 320 to 535 mg/L. A 30 mL sample of Damaged wheat grain (filtrate) mixed with palm oil mill effluent (filtrate) was taken. Weighed 0.02 g $HgSO_4$ in separate 15 mL test tubes. 1.0 mL of glucose solution and sample were added to each test tube separately and mixed well. 0.5 mL of $K_2Cr_2O_7$ was added to each sample. 1.5 mL $H_2SO_4$ silver sulphate reagent was added slowly with continuous shaking. The color of the reaction mixture was noted down visually within 15 sec of incubation and also recorded spectrophotometrically at 585 and 635 nm against air. An approximate COD value of the sample was estimated from the color of standard reaction mixture prepared with glucose as reference material in the COD range of 200 to 100000 mg/L. OD 585 and OD 635 of the reaction mixture was read spectrophotometrically. OD 585 and 635 nm in the range of 0.130 to 0.175 and 0.120 to 0.160 respectively were considered and calculated with reference to glucose standard. (Glucose COD in the range of 320 to 535 mg/L corresponds to OD 585 and 635 nm in the range of 0.157 to 0.207 and 0.142 to 0.189, respectively).

COD of the sample was estimated to be 5391 mg/L. (By Merck method and read on photometer).

Based on the color of the reaction mixture, COD of the sample was estimated to be around 3700 mg/L. On the basis of the dilution method and the spectrophotometric reading at OD 585 and OD 635 of the sample, COD was estimated to be 5344 mg/L. A comparison with the COD value calculated through Merck method reveals the following relation i.e. Our COD value (at OD 585 or OD 635)×1.01=COD value (Merck Method).

Hence for a preliminary estimate of COD value, color of the standard reaction mixture based on a range of glucose concentrations can be used as a reference. For samples, with COD concentration of 300 to 500 mg/L, OD 585 or OD 635 can be recorded for obtaining more precise values.

TABLE 22

Correlation between COD concentration, color of the reaction mixture and their OD at different wave lengths.

| COD (mg/L) 1 | Sample dilution (Times) 2 | Color of the reaction mixture 3 | OD 4 | Estimated COD (mg/L) 5 | Estimated final COD (mg/L) (Col. 2 × 5) 6 |
|---|---|---|---|---|---|
| Values at OD 585 nm | | | | | |
| Glucose: | | | | | |
| 320 | NA | C300 | 0.161 | NA | NA |
| 426 | NA | C400 | 0.186 | NA | NA |
| 535 | NA | C550 | 0.206 | NA | NA |
| Sample: Damaged wheat grain (filtrate) + Palm oil mill effluent (filtrate) | | | | | |
| | Nil | C2000 | 0.533 | ≅2000# | ≅2000 |
| | 5 | C600 | 0.258 | ≅580# | ≅2900 |
| | 10 | C400 | 0.183 | ≅373# | ≅3730 |
| | 16.7 | C300 | 0.133 | 320 | 5344 |
| Values at OD 635 nm | | | | | |
| Glucose: | | | | | |
| 320 | NA | C300 | 0.146 | NA | NA |
| 426 | NA | C400 | 0.167 | NA | NA |
| 535 | NA | C550 | 0.186 | NA | NA |
| Sample: Damaged wheat grain (filtrate) + Palm oil mill effluent (filtrate) | | | | | |
| | Nil | C2000 | 0.442 | ≅2000# | ≅2000 |
| | 5 | C600 | 0.234 | ≅580# | ≅2900 |
| | 10 | C400 | 0.165 | ≅373# | ≅3730 |
| | 16.7 | C300 | 0.120 | 320 | 5344 |

COD as deducible from Table 2 given in Example 2.
D: Dark.
T: Turbid.
*OD out of range.
NA: Not applicable.
Samples are diluted to get an OD 585 in the range of 0.130 to 0.175 and OD 635 in the range of 0.120 to 0.160, to obtain a COD value in the range of 320 to 535 mg/L. (Based on the Tables 3 to 15 given in Examples 3 to 15).

EXAMPLE 23

Dissolved 0.15 g glucose in 25 mL distilled water. Aliquots from the stock solution were taken and diluted with water to achieve different COD concentrations in the range of 320 to 535 mg/L. A 30 mL sample of Damaged wheat grain (filtrate) was taken. Weighed 0.02 g $HgSO_4$ in separate 15 mL test tubes. 1.0 mL of glucose solution and sample were added to each test tube separately and mixed well. 0.5 ml of $K_2Cr_2O_7$ was added to each sample. 1.5 mL $H_2SO_4$ silver sulphate reagent was added slowly with continuous shaking. The color of the reaction mixture was noted down visually within 15 sec of incubation and also recorded spectrophotometrically at 585 and 635 nm against air. An approximate COD value of the sample was estimated from the color of standard reaction mixture prepared with glucose as reference material in the COD range of 200 to 100000 mg/L. OD 585 and OD 635 of the reaction mixture was read spectrophotometrically. OD 585 and 635 nm in the range of 0.130 to 0.175 and 0.120 to 0.160 respectively were considered and calculated with reference to glucose standard. (Glucose COD in the range of 320 to 535 mg/L corresponds to OD 585 and 635 nm in the range of 0.157 to 0.207 and 0.142 to 0.189, respectively).

COD of the sample was estimated to be 6250 mg/L. (By Merck method and read on photometer).

Based on the color of the reaction mixture, COD of the sample was estimated to be around 5800 mg/L. On the basis of the dilution method and the spectrophotometric reading at OD 585 and OD 635 of the sample, COD was estimated to be 8020 and 6700 mg/L, respectively. A comparison with the COD value calculated through Merck method reveals the following relation i.e. Our COD value (at OD 585)×0.78= COD value (Merck Method) or our COD value (at OD 635)×0.93=COD value (Merck Method).

Hence for a preliminary estimate of COD value, color of the standard reaction mixture based on a range of glucose concentrations can be used as a reference. For samples, with COD concentration of 300 to 500 mg/L, OD 585 or OD 635 can be recorded for obtaining more precise values.

TABLE 23

Correlation between COD concentration, color of the reaction mixture and their OD at different wave lengths.

| COD (mg/L) 1 | Sample dilution (Times) 2 | Color of the reaction mixture 3 | OD 4 | Estimated COD (mg/L) 5 | Estimated final COD (mg/L) (Col. 2 × 5) 6 |
|---|---|---|---|---|---|
| Values at OD 585 nm | | | | | |
| Glucose: | | | | | |
| 320 | NA | C300 | 0.159 | NA | NA |
| 426 | NA | C400 | 0.186 | NA | NA |
| 535 | NA | C550 | 0.205 | NA | NA |
| Sample: Damaged wheat grain (filtrate) | | | | | |
| | Nil | C1900 | 1.325 | ≅1900# | ≅1900 |
| | 10 | C600 | 0.204 | ≅580# | ≅5800 |
| | 20 | C400 | 0.146 | 401 | 8020 |
| Values at OD 635 nm | | | | | |
| Glucose: | | | | | |
| 320 | NA | C300 | 0.149 | NA | NA |
| 426 | NA | C400 | 0.166 | NA | NA |
| 535 | NA | C550 | 0.183 | NA | NA |

TABLE 23-continued

Correlation between COD concentration, color of the reaction mixture and their OD at different wave lengths.

| COD (mg/L) 1 | Sample dilution (Times) 2 | Color of the reaction mixture 3 | OD 4 | Estimated COD (mg/L) 5 | Estimated final COD (mg/L) (Col. 2 × 5) 6 |
|---|---|---|---|---|---|
| Sample: Damaged wheat grain (filtrate) | | | | | |
| Nil | | C1900 | 1.146 | ≅1900# | ≅1900 |
| 10 | | C600 | 0.184 | ≅580# | ≅5800 |
| 20 | | C350 | 0.130 | 335 | 6700 |

COD as deducible from Table 2 given in Example 2.
D: Dark.
T: Turbid.
*OD out of range.
NA: Not applicable.
Samples are diluted to get an OD 585 in the range of 0.130 to 0.175 and OD 635 in the range of 0.120 to 0.160, to obtain a COD value in the range of 320 to 535 mg/L. (Based on the Tables 3 to 15 given in Examples 3 to 15).

EXAMPLE 24

Dissolved 0.15 g glucose in 25 mL distilled water. Aliquots from the stock solution were taken and diluted with water to achieve different COD concentrations in the range of 320 to 535 mg/L. A 30 mL sample of Damaged wheat grain (filtrate) slurry was taken. Weighed 0.02 g $HgSO_4$ in separate 15 mL test tubes. 1.0 mL of glucose solution and sample were added to each test tube separately and mixed well. 0.5 mL of $K_2Cr_2O_7$ was added to each sample. 1.5 mL $H_2SO_4$ silver sulphate reagent was added slowly with continuous shaking. The color of the reaction mixture was noted down visually within 15 sec of incubation and also recorded spectrophotometrically at 585 and 635 nm against air. An approximate COD value of the sample was estimated from the color of standard reaction mixture prepared with glucose as reference material in the COD range of 200 to 100000 mg/L. OD 585 and OD 635 of the reaction mixture was read spectrophotometrically. OD 585 and 635 nm in the range of 0.130 to 0.175 and 0.120 to 0.160 respectively were considered and calculated with reference to glucose standard. (Glucose COD in the range of 320 to 535 mg/L corresponds to OD 585 and 635 nm in the range of 0.157 to 0.207 and 0.142 to 0.189, respectively).

COD of the sample was estimated to be 9794 mg/L. (By Merck method and read on photometer).

Based on the color of the reaction mixture, COD of the sample was estimated to be around 10,000 mg/L. On the basis of the dilution method and the spectrophotometric reading at OD 585 and OD 635 of the sample, COD was estimated to be 6840 and 6700 mg/L, respectively. A comparison with the COD value calculated through Merck method reveals the following relation i.e. Our COD value (at OD 585)×1.43=COD value (Merck Method) or our COD value (at OD 635)×1.46=COD value (Merck Method).

Hence for a preliminary estimate of COD value, color of the standard reaction mixture based on a range of glucose concentrations can be used as a reference. For samples with COD concentration of 300 to 500 mg/L, OD 585 or OD 635 can be recorded for obtaining more precise values.

TABLE 24

Correlation between COD concentration, color of the reaction mixture and their OD at different wave lengths.

| COD (mg/L) 1 | Sample dilution (Times) 2 | Color of the reaction mixture 3 | OD 4 | Estimated COD (mg/L) 5 | Estimated final COD (mg/L) (Col. 2 × 5) 6 |
|---|---|---|---|---|---|
| Values at OD 585 nm | | | | | |
| Glucose: | | | | | |
| 320 | NA | C300 | 0.159 | NA | NA |
| 426 | NA | C400 | 0.186 | NA | NA |
| 535 | NA | C550 | 0.205 | NA | NA |
| Sample: Damaged wheat grain (filtrate) | | | | | |
| Nil | | C10000 | 0.834 | ≅10000# | ≅10000 |
| 20 | | C350 | 0.142 | 342 | 6840 |
| Values at OD 635 nm | | | | | |
| Glucose: | | | | | |
| 320 | NA | C300 | 0.145 | NA | NA |
| 426 | NA | C400 | 0.166 | NA | NA |
| 535 | NA | C550 | 0.187 | NA | NA |
| Sample: Damaged wheat grain (filtrate) | | | | | |
| Nil | | C10000 | 0.654 | ≅10000# | ≅10000 |
| 20 | | C350 | 0.127 | 335 | 6700 |

COD as deducible from Table 2 given in Example 2.
D: Dark.
T: Turbid.
*OD out of range.
NA: Not applicable.
Samples are diluted to get an OD 585 in the range of 0.130 to 0.175 and OD 635 in the range of 0.120 to 0.160, to obtain a COD value in the range of 320 to 535 mg/L (Based on the Tables 3 to 15 given in Examples 3 to 15).

EXAMPLE 25

Dissolved 0.15 g glucose in 25 mL distilled water. Aliquots from the stock solution were taken and diluted with water to achieve different COD concentrations in the range of 320 to 535 mg/L. A 30 mL sample of Damaged wheat grain (filtrate) slurry was taken. Weighed 0.02 g $HgSO_4$ in separate 15 mL test tubes. 1.0 mL of glucose solution and sample were added to each test tube separately and mixed well. 0.5 mL of $K_2Cr_2O_7$ was added to each sample. 1.5 mL $H_2SO_4$ silver sulphate reagent was added slowly with continuous shaking. The color of the reaction mixture was noted down visually within 15 sec of incubation and also recorded spectrophotometrically at 585 and 635 nm against air. An approximate COD value of the sample was estimated from the color of standard reaction mixture prepared with glucose as reference material in the COD range of 200 to 100000 mg/L. OD 585 and OD 635 of the reaction mixture was read spectrophotometrically. OD 585 and 635 nm in the range of 0.130 to 0.175 and 0.120 to 0.160 respectively were considered and calculated with reference to glucose standard. (Glucose COD in the range of 320 to 535 mg/L corresponds to OD 585 and 635 nm in the range of 0.157 to 0.207 and 0.142 to 0.189, respectively).

COD of the sample was estimated to be 15502 mg/L. (By Merck method and read on photometer).

Based on the color of the reaction mixture, COD of the sample was estimated to be around 10,000 mg/L. On the basis of the dilution method and the spectrophotometric reading at OD 585 and OD 635 of the sample, COD was estimated to be 8000 and 7725 mg/L, respectively. A comparison with the COD value calculated through Merck method reveals the following relation i.e. Our COD value (at OD 585)×1.94=COD value (Merck Method) or our COD value (at OD 635)×2.01=COD value (Merck Method).

Hence for a preliminary estimate of COD value, color of the standard reaction mixture based on a range of glucose concentrations can be used as a reference. For samples, with COD concentration of 300 to 500 mg/L, OD 585 or OD 635 can be recorded for obtaining more precise values.

TABLE 25

Correlation between COD concentration, color of the reaction mixture and their OD at different wave lengths.

| COD (mg/L) 1 | Sample dilution (Times) 2 | Color of the reaction mixture 3 | OD 4 | Estimated COD (mg/L) 5 | Estimated final COD (mg/L) (Col. 2 × 5) 6 |
|---|---|---|---|---|---|
| Values at OD 585 nm | | | | | |
| Glucose: | | | | | |
| 320 | NA | C300 | 0.164 | NA | NA |
| 426 | NA | C400 | 0.186 | NA | NA |
| 535 | NA | C550 | 0.205 | NA | NA |
| Sample: Damaged wheat grain (filtrate) | | | | | |
| | Nil | C10000 | 0.964 | >10000# | >10000 |
| | 10 | C600 | 0.267 | >600# | >6000 |
| | 25 | C300 | 0.137 | 320 | 8000 |
| Values at OD 635 nm | | | | | |
| Glucose: | | | | | |
| 320 | NA | C300 | 0.152 | NA | NA |
| 426 | NA | C400 | 0.166 | NA | NA |
| 535 | NA | C550 | 0.184 | NA | NA |
| Sample: Damaged wheat grain (filtrate) | | | | | |
| | Nil | C10000 | 0.714 | >10000# | >10000 |
| | 10 | C600 | 0.252 | >600# | >6000 |
| | 25 | C300 | 0.122 | 309 | 7725 |

COD as deducible from Table 2 given in Example 2.
D: Dark.
T: Turbid.
*OD out of range.
NA: Not applicable.
Samples are diluted to get an OD 585 in the range of 0.130 to 0.175 and OD 635 in the range of 0.120 to 0.160, to obtain a COD value in the range of 320 to 535 mg/L. (Based on the Tables 3 to 15 given in Examples 3 to 15).

EXAMPLE 26

Dissolved 0.15 g glucose in 25 mL distilled water. Aliquots from the stock solution were taken and diluted with water to achieve different COD concentrations in the range of 320 to 535 mg/L. A 30 mL sample of Cattle dung slurry was taken. Weighed 0.02 g $HgSO_4$ in separate 15 mL test tubes. 1.0 mL of glucose solution and sample were added to each test tube separately and mixed well. 0.5 mL of $K_2Cr_2O_7$ was added to each sample. 1.5 mL $H_2SO_4$ silver sulphate reagent was added slowly with continuous shaking. The color of the reaction mixture was noted down visually within 15 sec of incubation and also recorded spectrophotometrically at 585 and 635 nm against air. An approximate COD value of the sample was estimated from the color of standard reaction mixture prepared with glucose as reference material in the COD range of 200 to 100000 mg/l. OD 585 and OD 635 of the reaction mixture was read spectrophotometrically. OD 585 and 635 nm in the range of 0.130 to 0.175 and 0.120 to 0.160 respectively were considered and calculated with reference to glucose standard. (Glucose COD in the range of 320 to 535 mg/L corresponds to OD 585 and 635 nm in the range of 0.157 to 0.207 and 0.142 to 0.189, respectively).

COD of the sample was estimated to be 18515 mg/L. (By Merck method and read on photometer).

Based on the color of the reaction mixture, COD of the sample was estimated to be around 10,000 mg/L. On the basis of the dilution method and the spectrophotometric reading at OD 585 and OD 635 of the sample, COD was estimated to be 8660 mg/L. A comparison with the COD value calculated through Merck method reveals the following relation i.e. Our COD value (at OD 585 or OD 635)× 2.14=COD value (Merck Method).

Hence for a preliminary estimate of COD value, color of the standard reaction mixture based on a range of glucose concentrations can be used as a reference. For samples, with COD concentration of 300 to 500 mg/L, OD 585 or OD 635 can be recorded for obtaining more precise values.

TABLE 26

Correlation between COD concentration, color of the reaction mixture and their OD at different wave lengths.

| COD (mg/L) 1 | Sample dilution (Times) 2 | Color of the reaction mixture 3 | OD 4 | Estimated COD (mg/L) 5 | Estimated final COD (mg/L) (Col. 2 × 5) 6 |
|---|---|---|---|---|---|
| Values at OD 585 nm | | | | | |
| Glucose: | | | | | |
| 320 | NA | C300 | 0.162 | NA | NA |
| 426 | NA | C400 | 0.185 | NA | NA |
| 535 | NA | C550 | 0.205 | NA | NA |
| Sample: Cattle dung slurry | | | | | |
| | Nil | C10000 | 1.878 | ≅10000# | ≅10000 |
| | 20 | C450 | 0.157 | 433 | 8660 |
| Values at OD 635 nm | | | | | |
| Glucose: | | | | | |
| 320 | NA | C300 | 0.148 | NA | NA |
| 426 | NA | C400 | 0.171 | NA | NA |
| 535 | NA | C550 | 0.189 | NA | NA |
| Sample: Cattle dung slurry | | | | | |
| | Nil | C10000 | 1.637 | ≅10000# | ≅10000 |
| | 20 | C450 | 0.145 | 433 | 8660 |

COD as deducible from Table 2 given in Example 2.
D: Dark.
T: Turbid.
*OD out of range.
NA: Not applicable.
Samples are diluted to get an OD 585 in the range of 0.130 to 0.175 and OD 635 in the range of 0.120 to 0.160, to obtain a COD value in the range of 320 to 535 mg/L. (Based on the Tables 3 to 15 given in Examples 3 to 15).

EXAMPLE 27

Dissolved 0.15 g glucose in 25 mL distilled water. Aliquots from the stock solution were taken and diluted with water to achieve different COD concentrations in the range of 320 to 535 mg/L. A 30 mL sample of Palm Oil Mill Effluent (Digested) with Damaged wheat grains (filtrate) slurry was taken. Weighed 0.02 g $HgSO_4$ in separate 15 mL test tubes. 1.0 mL of glucose solution and sample were added to each test tube separately and mixed well. 0.5 mL of $K_2Cr_2O_7$ was added to each sample. 1.5 mL $H_2SO_4$ silver sulphate reagent was added slowly with continuous shaking. The color of the reaction mixture was noted down visually within 15 sec of incubation and also recorded spectrophotometrically at 585 and 635 nm against air. An approximate COD value of the sample was estimated from the color of standard reaction mixture prepared with glucose as reference material in the COD range of 200 to 100000 mg/l. OD 585 and OD 635 of the reaction mixture was read spectrophotometrically. OD 585 and 635 nm in the range of 0.130 to 0.175 and 0.120 to 0.160 respectively were considered and calculated with reference to glucose standard. (Glucose COD in the range of 320 to 535 mg/L corresponds to OD 585 and 635 nm in the range of 0.157 to 0.207 and 0.142 to 0.189, respectively).

COD of the sample was estimated to be 19941 mg/L. (By Merck method and read on photometer).

Based on the color of the reaction mixture, COD of the sample was estimated to be around 12,000 mg/L. On the basis of the dilution method and the spectrophotometric reading at OD 585 and OD 635 of the sample, COD was estimated to be 10656 and 11355 mg/L, respectively. A comparison with the COD value calculated through Merck method reveals the following relation i.e. Our COD value (at OD 585)×1.87=COD value (Merck Method) or our COD value (at OD 635)×1.76=COD value (Merck Method).

Hence for a preliminary estimate of COD value, color of the standard reaction mixture based on a range of glucose concentrations can be used as a reference. For samples, with COD concentration of 300 to 500 mg/L, OD 585 or OD 635 can be recorded for obtaining more precise values.

TABLE 27

Correlation between COD concentration, color of the reaction mixture and their OD at different wave lengths.

| COD (mg/L) 1 | Sample dilution (Times) 2 | Color of the reaction mixture 3 | OD 4 | Estimated COD (mg/L) 5 | Estimated final COD (mg/L) (Col. 2 × 5) 6 |
|---|---|---|---|---|---|
| Values at OD 585 nm | | | | | |
| Glucose: | | | | | |
| 320 | NA | C300 | 0.158 | NA | NA |
| 426 | NA | C400 | 0.185 | NA | NA |
| 535 | NA | C550 | 0.205 | NA | NA |
| Sample: Palm Oil Mill Effluent (Digested) + Damaged wheat grains (filtrate) | | | | | |
| Nil | C10000 | 6.000* | >10000# | >10000 | |
| 20 | C600 | 0.195 | ≅600# | ≅12000 | |
| 33.3 | C300 | 0.131 | 320 | 10656 | |
| Values at OD 635 nm | | | | | |
| Glucose: | | | | | |
| 320 | NA | C300 | 0.137 | NA | NA |
| 426 | NA | C400 | 0.163 | NA | NA |
| 535 | NA | C550 | 0.185 | NA | NA |
| Sample: Palm Oil Mill Effluent (Digested) + Damaged wheat grains (filtrate) | | | | | |
| Nil | C10000 | 6.000* | >10000# | >10000 | |
| 20 | C600 | 0.182 | ≅600# | ≅12000 | |
| 33.3 | C300 | 0.122 | 341 | 11355 | |

COD as deducible from Table 2 given in Example 2.
D: Dark.
T: Turbid.
*OD out of range.
NA: Not applicable.
Samples are diluted to get an OD 585 in the range of 0.130 to 0.175 and OD 635 in the range of 0.120 to 0.160, to obtain a COD value in the range of 320 to 535 mg/L (Based on the Tables 3 to 15 given in Examples 3 to 15).

EXAMPLE 28

Dissolved 0.15 g glucose in 25 mL distilled water. Aliquots from the stock solution were taken and diluted with water to achieve different COD concentrations in the range of 320 to 535 mg/L. A 30 mL sample of Palm Oil Mill Effluent (Digested) was taken. Weighed 0.02 g $HgSO_4$ in separate 15 mL test tubes. 1.0 mL of glucose solution and sample were added to each test tube separately and mixed well. 0.5 mL of $K_2Cr_2O_7$ was added to each sample. 1.5 mL $H_2SO_4$ silver sulphate reagent was added slowly with continuous shaking. The color of the reaction mixture was noted down visually within 15 sec of incubation and also recorded spectrophotometrically at 585 and 635 nm against air. An approximate COD value of the sample was estimated from the color of standard reaction mixture prepared with glucose as reference material in the COD range of 200 to 100000 mg/l. OD 585 and OD 635 of the reaction mixture was read spectrophotometrically. OD 585 and 635 nm in the range of 0.130 to 0.175 and 0.120 to 0.160 respectively were considered and calculated with reference to glucose standard. (Glucose COD in the range of 320 to 535 mg/l corresponds to OD 585 and 635 nm in the range of 0.157 to 0.207 and 0.142 to 0.189, respectively).

COD of the sample was estimated to be 22287 mg/L. (By Merck method and read on photometer).

Based on the color of the reaction mixture, COD of the sample was estimated to be around 20,000 mg/L. On the basis of the dilution method and the spectrophotometric reading at OD 585 and OD 635 of the sample, COD was estimated to be 15840 and 13560 mg/l, respectively. A comparison with the COD value calculated through Merck method reveals the following relation i.e. Our COD value (at OD 585)×1.41=COD value (Merck Method) or our COD value (at OD 635)×1.64=COD value (Merck Method).

Hence for a preliminary estimate of COD value, color of standard reaction mixture can be used as a reference. For samples, with COD concentration of 300 to 500 mg/L, OD 585 or OD 635 can be recorded for obtaining more precise values.

TABLE 28

Correlation between COD concentration, color of the reaction mixture and their OD at different wave lengths.

| COD (mg/L) 1 | Sample dilution (Times) 2 | Color of the reaction mixture 3 | OD 4 | Estimated COD (mg/L) 5 | Estimated final COD (mg/L) (Col. 2 × 5) 6 |
|---|---|---|---|---|---|
| Values at OD 585 nm | | | | | |
| Glucose: | | | | | |
| 320 | NA | C300 | 0.162 | NA | NA |
| 426 | NA | C400 | 0.185 | NA | NA |
| 535 | NA | C550 | 0.205 | NA | NA |
| Sample: Palm Oil Mill Effluent (Digested) | | | | | |
| Nil | C10000 | 6.000* | >10000# | >10000 | |
| 10 | C2000 | 0.345 | >2000# | >20000 | |
| 50 | C250 | 0.119 | ≅250 | ≅12500 | |
| 40 | C400 | 0.143 | 396 | 15840 | |
| Values at OD 635 nm | | | | | |
| Glucose: | | | | | |
| 320 | NA | C300 | 0.148 | NA | NA |
| 426 | NA | C400 | 0.171 | NA | NA |
| 535 | NA | C550 | 0.189 | NA | NA |
| Sample: Palm Oil Mill Effluent (Digested) | | | | | |
| Nil | C10000 | 6.000* | >10000# | >10000 | |
| 10 | C2000 | 0.330 | >2000# | >20000 | |

TABLE 28-continued

Correlation between COD concentration, color of the reaction mixture and their OD at different wave lengths.

| COD (mg/L) 1 | Sample dilution (Times) 2 | Color of the reaction mixture 3 | OD 4 | Estimated COD (mg/L) 5 | Estimated final COD (mg/L) (Col. 2 × 5) 6 |
|---|---|---|---|---|---|
| | 50 | C250 | 0.109 | ≅250 | ≅12500 |
| | 40 | C400 | 0.131 | 339 | 13560 |

COD as deducible from Table 2 given in Example 2.
D: Dark.
T: Turbid.
*OD out of range.
NA: Not applicable.
Samples are diluted to get an OD 585 in the range of 0.130 to 0.175 and OD 635 in the range of 0.120 to 0.160, to obtain a COD value in the range of 320 to 535 mg/L. (Based on the Tables 3 to 15 given in Examples 3 to 15).

EXAMPLE 29

Dissolved 0.15 g glucose in 25 mL distilled water. Aliquots from the stock solution were taken and diluted with water to achieve different COD concentrations in the range of 320 to 535 mg/L. A 30 mL sample of Palm Oil Mill Effluent (Digested) with Apple pomace was taken. Weighed 0.02 g $HgSO_4$ in separate 15 mL test tubes. 1.0 mL of glucose solution and sample were added to each test tube separately and mixed well. 0.5 mL of $K_2Cr_2O_7$ was added to each sample. 1.5 mL $H_2SO_4$ silver sulphate reagent was added slowly with continuous shaking. The color of the reaction mixture was noted down visually within 15 sec of incubation and also recorded spectrophotometrically at 585 and 635 nm against air. An approximate COD value of the sample was estimated from the color of standard reaction mixture prepared with glucose as reference material in the COD range of 200 to 100000 mg/L. OD 585 and OD 635 of the reaction mixture was read spectrophotometrically. OD 585 and 635 nm in the range of 0.130 to 0.175 and 0.120 to 0.160 respectively were considered and calculated with reference to glucose standard. (Glucose COD in the range of 320 to 535 mg/L corresponds to OD 585 and 635 nm in the range of 0.157 to 0.207 and 0.142 to 0.189, respectively).

COD of the sample was estimated to be 44620 mg/L. (By Merck method and read on photometer).

Based on the color of the reaction mixture, COD of the sample was estimated to be around 40,000 mg/L. On the basis of the dilution method and the spectrophotometric reading at OD 585 and OD 635 of the sample, COD was estimated to be 38640 and 40080 mg/L, respectively. A comparison with the COD value calculated through Merck method reveals the following relation i.e. Our COD value (at OD 585)×1.15=COD value (Merck Method) or our COD value (at OD 635)×1.11=COD value (Merck Method).

Hence for a preliminary estimate of COD value, color of the standard reaction mixture based on a range of glucose concentrations can be used as a reference. For samples, with COD concentration of 300 to 500 mg/L, OD 585 or OD 635 can be recorded for obtaining more precise values.

TABLE 29

Correlation between COD concentration, color of the reaction mixture and their OD at different wave lengths.

| COD (mg/L) 1 | Sample dilution (Times) 2 | Color of the reaction mixture 3 | OD 4 | Estimated COD (mg/L) 5 | Estimated final COD (mg/L) (Col. 2 × 5) 6 |
|---|---|---|---|---|---|
| Values at OD 585 nm | | | | | |
| Glucose: | | | | | |
| 320 | NA | C300 | 0.155 | NA | NA |
| 426 | NA | C400 | 0.185 | NA | NA |
| 535 | NA | C550 | 0.205 | NA | NA |
| Sample: Palm Oil Mill Effluent (Digested) + Apple pomace | | | | | |
| | Nil | C10000 | 6.000* | >10000# | >10000 |
| | 20 | C2000 | 0.352 | >2000# | >40000 |
| | 100 | C2000 | 0.220 | ≅250# | ≅25000 |
| | 120 | C300 | 0.132 | 320 | 38640 |
| Values at OD 635 nm | | | | | |
| Glucose: | | | | | |
| 320 | NA | C300 | 0.137 | NA | NA |
| 426 | NA | C400 | 0.163 | NA | NA |
| 535 | NA | C550 | 0.185 | NA | NA |
| Sample: Palm Oil Mill Effluent (Digested) + Apple pomace | | | | | |
| | Nil | C10000 | 6.000* | >10000# | >10000 |
| | 20 | C2000 | 0.322 | >2000# | >40000 |
| | 100 | C2000 | 0.190 | ≅250# | ≅25000 |
| | 120 | C300 | 0.119 | 334 | 40080 |

COD as deducible from Table 2 given in Example 2.
D: Dark.
T: Turbid.
*OD out of range.
NA: Not applicable.
Samples are diluted to get an OD 585 in the range of 0.130 to 0.175 and OD 635 in the range of 0.120 to 0.160, to obtain a COD value in the range of 320 to 535 mg/L. (Based on the Tables 3 to 15 given in Examples 3 to 15).

EXAMPLE 30

Dissolved 0.15 g glucose in 25 mL distilled water. Aliquots from the stock solution were taken and diluted with water to achieve different COD concentrations in the range of 320 to 535 mg/L. A 30 mL sample of Vegetable waste slurry with Apple pomace was taken. Weighed 0.02 g $HgSO_4$ in separate 15 mL test tubes. 1.0 mL of glucose solution and sample were added to each test tube separately and mixed well. 0.5 mL of $K_2Cr_2O_7$ was added to each sample. 1.5 mL $H_2SO_4$ silver sulphate reagent was added slowly with continuous shaking. The color of the reaction mixture was noted down visually within 15 sec of incubation and also recorded spectrophotometrically at 585 and 635 nm against air. An approximate COD value of the sample was estimated from the color of standard reaction mixture prepared with glucose as reference material in the COD range of 200 to 100000 mg/l. OD 585 and OD 635 of the reaction mixture was read spectrophotometrically. OD 585 and 635 nm in the range of 0.130 to 0.175 and 0.120 to 0.160 respectively were considered and calculated with reference to glucose standard. (Glucose COD in the range of 320 to 535 mg/L corresponds to OD 585 and 635 nm in the range of 0.157 to 0.207 and 0.142 to 0.189, respectively).

COD of the sample was estimated to be 35484 mg/L. (By Merck method and read on photometer).

Based on the color of the reaction mixture, COD of the sample was estimated to be around 40,000 mg/L. On the basis of the dilution method and the spectrophotometric reading at OD 585 and OD 635 of the sample, COD was estimated to be 40000 and 34000 mg/L, respectively. A comparison with the COD value calculated through Merck method reveals the following relation i.e. Our COD value (at OD 585)×0.89=COD value (Merck Method) or our COD value (at OD 635)×1.04=COD value (Merck Method).

Hence for a preliminary estimate of COD value, color of the standard reaction mixture based on a range of glucose concentrations can be used as a reference. For samples, with COD concentration of 300 to 500 mg/L, OD 585 or OD 635 can be recorded for obtaining more precise values.

TABLE 30

Correlation between COD concentration, color of the reaction mixture and their OD at different wave lengths.

| COD (mg/L) 1 | Sample dilution (Times) 2 | Color of the reaction mixture 3 | OD 4 | Estimated COD (mg/L) 5 | Estimated final COD (mg/L) (Col. 2 × 5) 6 |
|---|---|---|---|---|---|
| Values at OD 585 nm ||||||
| Glucose: ||||||
| 320 | NA | C300 | 0.163 | NA | NA |
| 426 | NA | C400 | 0.185 | NA | NA |
| 535 | NA | C550 | 0.202 | NA | NA |
| Sample: Vegetable waste slurry + Apple pomace ||||||
| Nil | | C10000 | 6.00* | >10000# | >10000 |
| 20 | | C2000 | 0.349 | >2000# | ≅40000 |
| 100 | | C400 | 0.145 | 400 | 40000 |
| Values at OD 635 nm ||||||
| Glucose: ||||||
| 320 | NA | C300 | 0.147 | NA | NA |
| 426 | NA | C400 | 0.170 | NA | NA |
| 535 | NA | C550 | 0.187 | NA | NA |
| Sample: Vegetable waste slurry + Apple pomace ||||||
| Nil | | C10000 | 6.00* | >10000# | >10000 |
| 20 | | C2000 | 0.318 | >2000# | ≅40000 |
| 100 | | C400 | 0.130 | 340 | 34000 |

COD as deducible from Table 2 given in Example 2.
D: Dark.
T: Turbid.
*OD out of range.
NA: Not applicable.
Samples are diluted to get an OD 585 in the range of 0.130 to 0.175 and OD 635 in the range of 0.120 to 0.160, to obtain a COD value in the range of 320 to 535 mg/L. (Based on the Tables 3 to 15 given in Examples 3 to 15).

EXAMPLE 31

Dissolved 0.15 g glucose in 25 mL distilled water. Aliquots from the stock solution were taken and diluted with water to achieve different COD concentrations in the range of 320 to 535 mg/L. A 30 mL sample of Damaged wheat grain (filtrate) with Apple pomace was taken. Weighed 0.02 g $HgSO_4$ in separate 15 mL test tubes. 1.0 mL of glucose solution and sample were added to each test tube separately and mixed well. 0.5 mL of $K_2Cr_2O_7$ was added to each sample. 1.5 mL $H_2SO_4$ silver sulphate reagent was added slowly with continuous shaking. The color of the reaction mixture was noted down visually within 15 sec of incubation and also recorded spectrophotometrically at 585 and 635 nm against air. An approximate COD value of the sample was estimated from the color of standard reaction mixture prepared with glucose as reference material in the COD range of 200 to 100000 mg/L. OD 585 and OD 635 of the reaction mixture was read spectrophotometrically. OD 585 and 635 nm in the range of 0.130 to 0.175 and 0.120 to 0.160 respectively were considered and calculated with reference to glucose standard. (Glucose COD in the range of 320 to 535 mg/L corresponds to OD 585 and 635 nm in the range of 0.157 to 0.207 and 0.142 to 0.189, respectively).

COD of the sample was estimated to be 36018 mg/L. (By Merck method and read on photometer).

Based on the color of the reaction mixture, COD of the sample was estimated to be around 30,000 mg/L. On the basis of the dilution method and the spectrophotometric reading at OD 585 and OD 635 of the sample, COD was estimated to be 42600 mg/l. A comparison with the COD value calculated through Merck method reveals the following relation i.e. Our COD value (at OD 585 or OD 635)× 0.84=COD value (Merck Method).

Hence for a preliminary estimate of COD value color of the standard reaction mixture based on a range of glucose concentrations can be used as a reference. For samples, with COD concentration of 300 to 500 mg/L, OD 585 or OD 635 can be recorded for obtaining more precise values.

TABLE 31

Correlation between COD concentration, color of the reaction mixture and their OD at different wave lengths.

| COD (mg/L) 1 | Sample dilution (Times) 2 | Color of the reaction mixture 3 | OD 4 | Estimated COD (mg/L) 5 | Estimated final COD (mg/L) (Col. 2 × 5) 6 |
|---|---|---|---|---|---|
| Values at OD 585 nm ||||||
| Glucose: ||||||
| 320 | NA | C300 | 0.164 | NA | NA |
| 426 | NA | C400 | 0.186 | NA | NA |
| 535 | NA | C550 | 0.205 | NA | NA |
| Sample: Damaged wheat grain (filtrate) + Apple pomace ||||||
| Nil | | C10000 | 6.000* | >10000# | >10000 |
| 10 | | C1500 | 0.442 | >1500# | >15000 |
| 50 | | C600 | 0.236 | >600# | >30000 |
| 100 | | C400 | 0.155 | 426 | 42600 |
| Values at OD 635 nm ||||||
| Glucose: ||||||
| 320 | NA | C300 | 0.152 | NA | NA |
| 426 | NA | C400 | 0.166 | NA | NA |
| 535 | NA | C550 | 0.184 | NA | NA |
| Sample: Damaged wheat grain (filtrate) + Apple pomace ||||||
| Nil | | C10000 | 6.000* | >10000# | >10000 |
| 10 | | C1500 | 0.377 | >1500# | >15000 |
| 50 | | C600 | 0.212 | >600# | >30000 |
| 100 | | C400 | 0.138 | 426 | 42600 |

COD as deducible from Table 2 given in Example 2.
D: Dark.
T: Turbid.
*OD out of range.
NA: Not applicable.
Samples are diluted to get an OD 585 in the range of 0.130 to 0.175 and OD 635 in the range of 0.120 to 0.160, to obtain a COD value in the range of 320 to 535 mg/L. (Based on the Tables 3 to 15 given in Examples 3 to 15).

EXAMPLE 32

Dissolved 0.15 g glucose in 25 mL distilled water. Aliquots from the stock solution were taken and diluted with water to achieve different COD concentrations in the range of 320 to 535 mg/L. A 30 mL sample of Damaged wheat grain slurry with Tea with Sodium sulphate was taken. Weighed 0.02 g $HgSO_4$ in separate 15 mL test tubes. 1.0 mL of glucose solution and sample were added to each test tube separately and mixed well. 0.5 mL of $K_2Cr_2O_7$ was added to each sample. 1.5 mL $H_2SO_4$ silver sulphate reagent was added slowly with continuous shaking. The color of the reaction mixture was noted down visually within 15 sec of incubation and also recorded spectrophotometrically at 585 and 635 nm against air. An approximate COD value of the sample was estimated from the color of standard reaction mixture prepared with glucose as reference material in the COD range of 200 to 100000 mg/L. OD 585 and OD 635 of the reaction mixture was read spectrophotometrically. OD 585 and 635 nm in the range of 0.130 to 0.175 and 0.120 to 0.160 respectively were considered and calculated with reference to glucose standard. (Glucose COD in the range of 320 to 535 mg/L corresponds to OD 585 and 635 nm in the range of 0.157 to 0.207 and 0.142 to 0.189, respectively).

COD of the sample was estimated to be 53867 mg/L. (By Merck method and read on photometer).

Based on the color of the reaction mixture, COD of the sample was estimated to be around 100,000 mg/L. On the basis of the dilution method and the spectrophotometric reading at OD 585 and OD 635 of the sample, COD was estimated to be 49896 and 51744 mg/L, respectively. A comparison with the COD value calculated through Merck method reveals the following relation i.e. Our COD value (at OD 585)×1.08=COD value (Merck Method) or our COD value (at OD 635)×1.04=COD value (Merck Method).

Hence for a preliminary estimate of COD value, color of the standard reaction mixture based on a range of glucose concentrations can be used as a reference. For samples, with COD concentration of 300 to 500 mg/L, OD 585 or OD 635 can be recorded for obtaining more precise values.

TABLE 32

Correlation between COD concentration, color of the reaction mixture and their OD at different wave lengths.

| COD (mg/L) | Sample dilution (Times) | Color of the reaction mixture | OD | Estimated COD (mg/L) | Estimated final COD (mg/L) (Col. 2 × 5) |
|---|---|---|---|---|---|
| 1 | 2 | 3 | 4 | 5 | 6 |
| Values at OD 585 nm ||||||
| Glucose: ||||||
| 320 | NA | C300 | 0.163 | NA | NA |
| 426 | NA | C400 | 0.183 | NA | NA |
| 535 | NA | C550 | 0.205 | NA | NA |
| Sample: Damaged wheat grain + Tea + Sodium sulphate ||||||
| | Nil | C10000 | 6.00* | >10000# | >10000 |
| | 10 | C10000 | 0.801* | ≅10000# | ≅100000 |
| | 154 | C300 | 0.138 | 324 | 49896 |
| Values at OD 635 nm ||||||
| Glucose: ||||||
| 320 | NA | C300 | 0.150 | NA | NA |
| 426 | NA | C400 | 0.167 | NA | NA |
| 535 | NA | C550 | 0.187 | NA | NA |
| Sample: Damaged wheat grain + Tea + Sodium sulphate ||||||
| | Nil | C10000 | 6.00* | >10000# | >10000 |
| | 10 | C10000 | 0.801* | ≅10000# | ≅100000 |
| | 154 | C300 | 0.124 | 336 | 51744 |

TABLE 32-continued

Correlation between COD concentration, color of the reaction mixture and their OD at different wave lengths.

| COD (mg/L) | Sample dilution (Times) | Color of the reaction mixture | OD | Estimated COD (mg/L) | Estimated final COD (mg/L) (Col. 2 × 5) |
|---|---|---|---|---|---|
| 1 | 2 | 3 | 4 | 5 | 6 |

COD as deducible from Table 2 given in Example 2.
D: Dark.
T: Turbid.
*OD out of range.
NA: Not applicable.
Samples are diluted to get an OD 585 in the range of 0.130 to 0.175 and OD 635 in the range of 0.120 to 0.160, to obtain a COD value in the range of 320 to 535 mg/L. (Based on the Tables 3 to 15 given in Examples 3 to 15).

EXAMPLE 33

Dissolved 0.15 g glucose in 25 mL distilled water. Aliquots from the stock solution were taken and diluted with water to achieve different COD concentrations in the range of 320 to 535 mg/L. A 30 mL sample of Apple pomace was taken. Weighed 0.02 g $HgSO_4$ in separate 15 mL test tubes. 1.0 mL of glucose solution and sample were added to each test tube separately and mixed well. 0.5 mL of $K_2Cr_2O_7$ was added to each sample. 1.5 mL $H_2SO_4$ silver sulphate reagent was added slowly with continuous shaking. The color of the reaction mixture was noted down visually within 15 sec of incubation and also recorded spectrophotometrically at 585 and 635 nm against air. An approximate COD value of the sample was estimated from the color of standard reaction mixture prepared with glucose as reference material in the COD range of 200 to 100000 mg/L. OD 585 and OD 635 of the reaction mixture was read spectrophotometrically. OD 585 and 635 nm in the range of 0.130 to 0.175 and 0.120 to 0.160 respectively were considered and calculated with reference to glucose standard. (Glucose COD in the range of 320 to 535 mg/L corresponds to OD 585 and 635 nm in the range of 0.157 to 0.207 and 0.142 to 0.189, respectively).

COD of the sample was estimated to be 55890 mg/L. (By Merck method and read on photometer).

Based on the color of the reaction mixture, COD of the sample was estimated to be around 50,000 mg/L. On the basis of the dilution method and the spectrophotometric reading at OD 585 and OD 635 of the sample, COD was estimated to be 65875 and 66500 mg/L, respectively. A comparison with the COD value calculated through Merck method reveals the following relation i.e. Our COD value (at OD 585)×0.85=COD value (Merck Method) or our COD value (at OD 635)×0.84=COD value (Merck Method).

Hence for a preliminary estimate of COD value, color of the standard reaction mixture based on a range of glucose concentrations can be used as a reference. For samples, with COD concentration of 300 to 500 mg/L, OD 585 or OD 635 can be recorded for obtaining more precise values.

TABLE 33

Correlation between COD concentration, color of the reaction mixture and their OD at different wave lengths.

| COD (mg/L) 1 | Sample dilution (Times) 2 | Color of the reaction mixture 3 | OD 4 | Estimated COD (mg/L) 5 | Estimated final COD (mg/L) (Col. 2 × 5) 6 |
|---|---|---|---|---|---|
| Values at OD 585 nm | | | | | |
| Glucose: | | | | | |
| 320 | NA | C300 | 0.161 | NA | NA |
| 426 | NA | C400 | 0.186 | NA | NA |
| 535 | NA | C550 | 0.206 | NA | NA |
| Sample: Apple pomace | | | | | |
|  | Nil | C10000 | 6.00* | >10000# | >10000 |
|  | 10 | C5000 | 0.525 | ≅5000# | ≅50000 |
|  | 125 | C500 | 0.171 | 527 | 65875 |
| Values at OD 635 nm | | | | | |
| Glucose: | | | | | |
| 320 | NA | C300 | 0.150 | NA | NA |
| 426 | NA | C400 | 0.167 | NA | NA |
| 535 | NA | C550 | 0.188 | NA | NA |
| Sample: Apple pomace | | | | | |
|  | Nil | C10000 | 6.00* | >10000# | >10000 |
|  | 10 | C5000 | 0.428 | ≅5000# | >50000 |
|  | 125 | C500 | 0.157 | 532 | 66500 |

COD as deducible from Table 2 given in Example 2.
D: Dark.
T: Turbid.
*OD out of range.
NA: Not applicable.
Samples are diluted to get an OD 585 in the range of 0.130 to 0.175 and OD 635 in the range of 0.120 to 0.160, to obtain a COD value in the range of 320 to 535 mg/L (Based on the Tables 3 to 15 given in Examples 3 to 15).

EXAMPLE 34

Dissolved 0.15 g glucose in 25 mL distilled water. Aliquots from the stock solution were taken and diluted with water to achieve different COD concentrations in the range of 320 to 535 mg/L. A 30 mL sample of Damaged wheat grain with Tea was taken. Weighed 0.02 g $HgSO_4$ in separate 15 mL test tubes. 1.0 mL of glucose solution and sample were added to each test tube separately and mixed well. 0.5 mL of $K_2Cr_2O_7$ was added to each sample. 1.5 mL $H_2SO_4$ silver sulphate reagent was added slowly with continuous shaking. The color of the reaction mixture was noted down visually within 15 sec of incubation and also recorded spectrophotometrically at 585 and 635 nm against air. An approximate COD value of the sample was estimated from the color of standard reaction mixture prepared with glucose as reference material in the COD range of 200 to 100000 mg/l. OD 585 and OD 635 of the reaction mixture was read spectrophotometrically. OD 585 and 635 nm in the range of 0.130 to 0.175 and 0.120 to 0.160 respectively were considered and calculated with reference to glucose standard. (Glucose COD in the range of 320 to 535 mg/L corresponds to OD 585 and 635 nm in the range of 0.157 to 0.207 and 0.142 to 0.189, respectively).

COD of the sample was estimated to be 58760 mg/L. (By Merck method and read on photometer).

Based on the color of the reaction mixture, COD of the sample was estimated to be around 64800 mg/L. On the basis of the dilution method and the spectrophotometric reading at OD 585 and OD 635 of the sample, COD was estimated to be 78848 and 84546 mg/L, respectively. A comparison with the COD value calculated through Merck method reveals the following relation i.e. Our COD value (at OD 585)×0.74=COD value (Merck Method) or our COD value (at OD 635)×0.70=COD value (Merck Method).

Hence for a preliminary estimate of COD value, color of the standard reaction mixture based on a range of glucose concentrations can be used as a reference. For samples, with COD concentration of 300 to 500 mg/L, OD 585 or OD 635 can be recorded for obtaining more precise values.

TABLE 34

Correlation between COD concentration, color of the reaction mixture and their OD at different wave lengths.

| COD (mg/L) 1 | Sample dilution (Times) 2 | Color of the reaction mixture 3 | OD 4 | Estimated COD (mg/L) 5 | Estimated final COD (Col. 2 × 5) 6 |
|---|---|---|---|---|---|
| Values at OD 585 nm | | | | | |
| Glucose: | | | | | |
| 320 | NA | C300 | 0.162 | NA | NA |
| 426 | NA | C400 | 0.186 | NA | NA |
| 535 | NA | C550 | 0.206 | NA | NA |
| Sample: Damaged wheat grain + Tea | | | | | |
|  | Nil | C10000 | 6.00* | >10000# | >10000 |
|  | 10 | C10000 | 6.00* | >10000# | ≅100000 |
|  | 100 | C1500 | 0.272 | ≅1500# | ≅150000 |
|  | 270 | C250 | 0.124 | ≅240# | ≅64800 |
|  | 154 | C500 | 0.164 | 512 | 78848 |
| Values at OD 635 nm | | | | | |
| Glucose: | | | | | |
| 320 | NA | C300 | 0.150 | NA | NA |
| 426 | NA | C400 | 0.167 | NA | NA |
| 535 | NA | C500 | 0.187 | NA | NA |
| Sample: Damaged wheat grain + Tea | | | | | |
|  | Nil | C10000 | 6.00* | >10000# | >10000 |
|  | 10 | C10000 | 6.00* | >10000# | ≅100000 |
|  | 100 | C1500 | 0.272 | ≅1500# | ≅150000 |
|  | 270 | C250 | 0.124 | ≅240# | ≅64800 |
|  | 154 | C500 | 0.160 | 549 | 84546 |

COD as deducible from Table 2 given in Example 2.
D: Dark.
T: Turbid.
*OD out of range.
NA: Not applicable.
Samples are diluted to get an OD 585 in the range of 0.130 to 0.175 and OD 635 in the range of 0.120 to 0.160, to obtain a COD value in the range of 320 to 535 mg/L. (Based on the Tables 3 to 15 given in Examples 3 to 15).

EXAMPLE 35

Dissolved 0.15 g glucose in 25 mL distilled water. Aliquots from the stock solution were taken and diluted with water to achieve different COD concentrations in the range of 320 to 535 mg/L. A 30 mL sample of Trizyme with Tea was taken. Weighed 0.02 g $HgSO_4$ in separate 15 mL test tubes. 1.0 mL of glucose solution and sample were added to each test tube separately and mixed well. 0.5 mL of $K_2Cr_2O_7$ was added to each sample. 1.5 mL $H_2SO_4$ silver sulphate reagent was added slowly with continuous shaking. The color of the reaction mixture was noted down visually within 15 sec of incubation and also recorded spectrophotometrically at 585 and 635 nm against air. An approximate COD value of the sample was estimated from the color of standard reaction mixture prepared with glucose as reference material in the COD range of 200 to 100000 mg/L. OD 585 and OD 635 of the reaction mixture was read spectrophotometrically. OD 585 and 635 nm in the range of 0.130 to 0.175 and 0.120 to 0.160 respectively were considered and calculated with reference to glucose standard. (Glucose COD in the range of 320 to 535 mg/L corresponds to OD 585 and 635 nm in the range of 0.157 to 0.207 and 0.142 to 0.189, respectively).

COD of the sample was estimated to be 61088 mg/L. (By Merck method and read on photometer).

Based on the color of the reaction mixture, COD of the sample was estimated to be around 100,000 mg/L. On the basis of the dilution method and the spectrophotometric reading at OD 585 and OD 635 of the sample, COD was estimated to be 79156 and 67914 mg/L, respectively. A comparison with the COD value calculated through Merck method reveals the following relation i.e. Our COD value (at OD 585)×0.77=COD value (Merck Method) or our COD value (at OD 635)×0.90=COD value (Merck Method).

Hence for a preliminary estimate of COD value color of the standard reaction mixture based on a range of glucose concentrations can be used as a reference. For samples, with COD concentration of 300 to 500 mg/L, OD 585 or OD 635 can be recorded for obtaining more precise values.

TABLE 35

Correlation between COD concentration, color of the reaction mixture and their OD at different wave lengths.

| COD (mg/L) 1 | Sample dilution (Times) 2 | Color of the reaction mixture 3 | OD 4 | Estimated COD (mg/L) 5 | Estimated final COD (mg/L) (Col. 2 × 5) 6 |
|---|---|---|---|---|---|
| Values at OD 585 nm | | | | | |
| Glucose: | | | | | |
| 320 | NA | C300 | 0.163 | NA | NA |
| 426 | NA | C400 | 0.183 | NA | NA |
| 535 | NA | C550 | 0.205 | NA | NA |
| Sample: Trizyme + Tea | | | | | |
| | Nil | C10000 | 6.00* | >10000# | >10000 |
| | 50 | C2000 | 0.338 | ≅2000# | ≅100000 |
| | 154 | C500 | 0.164 | 514 | 79156 |
| Values at OD 635 nm | | | | | |
| Glucose: | | | | | |
| 320 | NA | C300 | 0.152 | NA | NA |
| 426 | NA | C400 | 0.170 | NA | NA |
| 535 | NA | C550 | 0.184 | NA | NA |
| Sample: Trizyme + Tea | | | | | |
| | Nil | C10000 | 6.00* | >10000# | >10000 |
| | 50 | C2000 | 0.305 | ≅2000# | ≅100000 |
| | 154 | C500 | 0.147 | 441 | 67914 |

COD as deducible from Table 2 given in Example 2.
D: Dark.
T: Turbid.
*OD out of range.
NA: Not applicable.
Samples are diluted to get an OD 585 in the range of 0.130 to 0.175 and OD 635 in the range of 0.120 to 0.160, to obtain a COD value in the range of 320 to 535 mg/L. (Based on the Tables 3 to 15 given in Examples 3 to 15).

EXAMPLE 36

Dissolved 0.15 g glucose in 25 mL distilled water. Aliquots from the stock solution were taken and diluted with water to achieve different COD concentrations in the range of 320 to 535 mg/L. A 30 mL sample of Tea was taken. Weighed 0.02 g $HgSO_4$ in separate 15 mL test tubes. 1.0 mL of glucose solution and sample were added to each test tube separately and mixed well. 0.5 mL of $K_2Cr_2O_7$ was added to each sample. 1.5 mL $H_2SO_4$ silver sulphate reagent was added slowly with continuous shaking. The color of the reaction mixture was noted down visually within 15 sec of incubation and also recorded spectrophotometrically at 585 and 635 nm against air. An approximate COD value of the sample was estimated from the color of standard reaction mixture prepared with glucose as reference material in the COD range of 200 to 100000 mg/L. OD 585 and OD 635 of the reaction mixture was read spectrophotometrically. OD 585 and 635 nm in the range of 0.130 to 0.175 and 0.120 to 0.160 respectively were considered and calculated with reference to glucose standard. (Glucose COD in the range of 320 to 535 mg/L corresponds to OD 585 and 635 nm in the range of 0.157 to 0.207 and 0.142 to 0.189, respectively).

COD of the sample was estimated to be 1,36,608 mg/L. (By Merck method and read on photometer).

Based on the color of the reaction mixture, COD of the sample was estimated to be around 200,000 to 220,000 mg/L. On the basis of the dilution method and the spectrophotometric reading at OD 585 and OD 635 of the sample, COD was estimated to be 173983 and 172649 mg/L, respectively. A comparison with the COD value calculated through Merck method reveals the following relation i.e. Our COD value (at OD 585)×0.78=COD value (Merck Method) or our COD value (at OD 635)×0.79=COD value (Merck Method).

Hence for a preliminary estimate of COD value, color of the standard reaction mixture based on a range of glucose concentrations can be used as a reference. For samples, with COD concentration of 300 to 500 mg/L, OD 585 or OD 635 can be recorded for obtaining more precise values.

TABLE 36

Correlation between COD concentration, color of the reaction mixture and their OD at different wave lengths.

| COD (mg/L) 1 | Sample dilution (Times) 2 | Color of the reaction mixture 3 | OD 4 | Estimated COD (mg/L) 5 | Estimated final COD (mg/L) (Col. 2 × 5) 6 |
|---|---|---|---|---|---|
| Values at OD 585 nm | | | | | |
| Glucose: | | | | | |
| 320 | NA | C300 | 0.161 | NA | NA |
| 426 | NA | C400 | 0.187 | NA | NA |
| 535 | NA | C550 | 0.202 | NA | NA |
| Sample: Tea | | | | | |
| | Nil | C10000 | 6.00* | >10000# | >10000 |
| | 20 | C10000 | 1.648 | >10000# | ≅200000 |
| | 200 | C1100 | 0.216 | ≅1100# | ≅220000 |
| | 333.3 | C500 | 0.164 | 522 | 173983 |
| Values at OD 635 nm | | | | | |
| Glucose: | | | | | |
| 320 | NA | C300 | 0.144 | NA | NA |
| 426 | NA | C400 | 0.167 | NA | NA |
| 535 | NA | C550 | 0.184 | NA | NA |
| Sample: Tea | | | | | |
| | Nil | C10000 | 6.00* | >10000# | >10000 |
| | 20 | C10000 | 1.531 | >10000# | ≅200000 |

TABLE 36-continued

Correlation between COD concentration, color of the reaction mixture and their OD at different wave lengths.

| COD (mg/L) 1 | Sample dilution (Times) 2 | Color of the reaction mixture 3 | OD 4 | Estimated COD (mg/L) 5 | Estimated final COD (mg/L) (Col. 2 × 5) 6 |
|---|---|---|---|---|---|
| | 200 | C1100 | 0.196 | ≅1100# | ≅220000 |
| | 333.3 | C500 | 0.148 | 518 | 172649 |

COD as deducible from Table 2 given in Example 2.
D: Dark.
T: Turbid.
*OD out of range.
NA: Not applicable.
Samples are diluted to get an OD 585 in the range of 0.130 to 0.175 and OD 635 in the range of 0.120 to 0.160, to obtain a COD value in the range of 320 to 535 mg/L. (Based on the Tables 3 to 15 given in Examples 3 to 15).

EXAMPLE 37

Dissolved 0.15 g glucose in 25 mL distilled water. Aliquots from the stock solution were taken and diluted with water to achieve different COD concentrations in the range of 320 to 535 mg/L. A 30 mL sample of Damaged wheat grain (as such) was taken. Weighed 0.02 g $HgSO_4$ in separate 15 mL test tubes. 1.0 mL of glucose solution and sample were added to each test tube separately and mixed well. 0.5 mL of $K_2Cr_2O_7$ was added to each sample. 1.5 mL $H_2SO_4$ silver sulphate reagent was added slowly with continuous shaking. The color of the reaction mixture was noted down visually within 15 sec of incubation and also recorded spectrophotometrically at 585 and 635 nm against air. An approximate COD value of the sample was estimated from the color of standard reaction mixture prepared with glucose as reference material in the COD range of 200 to 100000 mg/L. OD 585 and OD 635 of the reaction mixture was read spectrophotometrically. OD 585 and 635 nm in the range of 0.130 to 0.175 and 0.120 to 0.160 respectively were considered and calculated with reference to glucose standard. (Glucose COD in the range of 320 to 535 mg/L corresponds to OD 585 and 635 nm in the range of 0.157 to 0.207 and 0.142 to 0.189, respectively).

COD of the sample was estimated to be 6210 mg/L. (By Merck method and read on photometer).

Based on the color of the reaction mixture, COD of the sample was estimated to be around 4000 mg/L. On the basis of the dilution method and the spectrophotometric reading at OD 585 and OD 635 of the sample, COD was estimated to be 4270 mg/l and 3370 mg/l. A comparison with the COD value calculated through Merck method reveals the following relation i.e. Our COD value (at OD 585)×1.45=COD value (Merck Method). or our COD value (at OD 635)×1.84=COD (Merck Method).

Hence for a preliminary estimate of COD value color of the standard reaction mixture based on a range of glucose concentrations can be used as a reference. For samples, with COD concentration of 300 to 500 mg/L, OD 585 or OD 635 can be recorded for obtaining more precise values.

TABLE 37

Correlation between COD concentration, color of the reaction mixture and their OD at different wave lengths.

| COD (mg/L) 1 | Sample dilution (Times) 2 | Color of the reaction mixture 3 | OD 4 | Estimated COD (mg/L) 5 | Estimated final COD (mg/L) (Col. 2 × 5) 6 |
|---|---|---|---|---|---|
| Values at OD 585 nm | | | | | |
| Glucose: | | | | | |
| 320 | NA | C300 | 0.165 | NA | NA |
| 426 | NA | C400 | 0.193 | NA | NA |
| 535 | NA | C550 | 0.213 | NA | NA |
| Sample: Damaged wheat grain (as such) | | | | | |
| | Nil | C1100 | 0.491 | ≅1100 | ≅1100# |
| | 10 | C400 | 0.154 | 427 | 4270 |
| Values at OD 635 nm | | | | | |
| Glucose: | | | | | |
| 320 | NA | C300 | 0.148 | NA | NA |
| 426 | NA | C400 | 0.172 | NA | NA |
| 535 | NA | C550 | 0.191 | NA | NA |
| Sample: Damaged wheat grain (as such) | | | | | |
| | Nil | C1100 | 0.401 | ≅1100 | ≅1100# |
| | 10 | C400 | 0.130 | 337 | 3370 |

COD as deducible from Table 2 given in Example 2.
D: Dark.
T: Turbid.
*OD out of range.
NA: Not applicable.
Samples are diluted to get an OD 585 in the range of 0.130 to 0.175 and OD 635 in the range of 0.120 to 0.160, to obtain a COD value in the range of 320 to 535 mg/L. (Based on the Tables 3 to 15 given in Examples 3 to 15).

EXAMPLE 38

Dissolved 0.3 g glucose in 50 mL distilled water. Aliquots from the stock solution were taken and diluted with water to achieve different COD concentrations in the range of 320 to 535 mg/L. A 30 mL sample of Damaged wheat grain (ssp) was taken. Weighed 0.02 g $HgSO_4$ in separate 15 mL test tubes. 1.0 mL of glucose solution and sample were added to each test tube separately and mixed well. 0.5 mL of $K_2Cr_2O_7$ was added to each sample. 1.5 mL $H_2SO_4$ silver sulphate reagent was added slowly with continuous shaking. The color of the reaction mixture was noted down visually within 15 sec of incubation and also recorded spectrophotometrically at 585 and 635 nm against air. An approximate COD value of the sample was estimated from the color of standard reaction mixture prepared with glucose as reference material in the COD range of 200 to 100000 mg/L. OD 585 and OD 635 of the reaction mixture was read spectrophotometrically. OD 585 and 635 nm in the range of 0.130 to 0.175 and 0.120 to 0.160 respectively were considered and calculated with reference to glucose standard. (Glucose COD in the range of 320 to 535 mg/L corresponds to OD 585 and 635 nm in the range of 0.157 to 0.207 and 0.142 to 0.189, respectively).

COD of the sample was estimated to be 4710.4 mg/L. (By Merck method and read on photometer).

Based on the color of the reaction mixture, COD of the sample was estimated to be around 4800 mg/L. On the basis of the dilution method and the spectrophotometric reading at OD 585 and OD 635 of the sample, COD was estimated to be 5220 and 4998 mg/l respectively. A comparison with the COD value calculated through Merck method reveals the following relation i.e. Our COD value (at OD 585)×0.90= COD value (Merck Method) or our COD value (at OD 635)×0.94=COD (Merck Method).

Hence for a preliminary estimate of COD value color of the standard reaction mixture based on a range of glucose concentrations can be used as a reference. For samples, with COD concentration of 300 to 500 mg/L, OD 585 or OD 635 can be recorded for obtaining more precise values.

TABLE 38

Correlation between COD concentration, color of the reaction mixture and their OD at different wave lengths.

| COD (mg/L) 1 | Sample dilution (Times) 2 | Color of the reaction mixture 3 | OD 4 | Estimated COD (mg/L) 5 | Estimated final COD (mg/L) (Col. 2 × 5) 6 |
|---|---|---|---|---|---|
| Values at OD 585 nm | | | | | |
| Glucose: | | | | | |
| 320 | NA | C300 | 0.163 | NA | NA |
| 426 | NA | C400 | 0.176 | NA | NA |
| 535 | NA | C550 | 0.226 | NA | NA |
| Sample: Damaged wheat grain (ssp) | | | | | |
| Nil | C1500 | 0.652 | 1500 | ≅1500 | |
| 10 | C200 | 0.187 | 224 | ≅2240# | |
| 12 | C400 | 0.147 | 435 | 5220 | |
| Values at OD 635 nm | | | | | |
| Glucose: | | | | | |
| 320 | NA | C300 | 0.146 | NA | NA |
| 426 | NA | C400 | 0.159 | NA | NA |
| 535 | NA | C550 | 0.205 | NA | NA |
| Sample: Damaged wheat grain (ssp) | | | | | |
| Nil | C1500 | 0.551 | 1500 | ≅1500 | |
| 10 | C200 | 0.168 | 224 | ≅2240# | |
| 12 | C400 | 0.127 | 416 | 4998 | |

COD as deducible from Table 2 given in Example 2.
D: Dark.
T: Turbid.
*OD out of range.
NA: Not applicable.
Samples are diluted to get an OD 585 in the range of 0.130 to 0.175 and OD 635 in the range of 0.120 to 0.160, to obtain a COD value in the range of 320 to 535 mg/L. (Based on the Tables 3 to 15 given in Examples 3 to 15).

EXAMPLE 39

Dissolved 0.15 g glucose in 25 mL distilled water. Aliquots from the stock solution were taken and diluted with water to achieve different COD concentrations in the range of 320 to 535 mg/L. A 30 mL sample of Palm oil mill effluent (as such) was taken. Weighed 0.02 g $HgSO_4$ in separate 15 mL test tubes. 1.0 mL of glucose solution and sample were added to each test tube separately and mixed well. 0.5 mL of $K_2Cr_2O_7$ was added to each sample. 1.5 mL $H_2SO_4$ silver sulphate reagent was added slowly with continuous shaking. The color of the reaction mixture was noted down visually within 15 sec of incubation and also recorded spectrophotometrically at 585 and 635 nm against air. An approximate COD value of the sample was estimated from the color of standard reaction mixture prepared with glucose as reference material in the COD range of 200 to 100000 mg/L. OD 585 and OD 635 of the reaction mixture was read spectrophotometrically. OD 585 and 635 nm in the range of 0.130 to 0.175 and 0.120 to 0.160 respectively were considered and calculated with reference to glucose standard. (Glucose COD in the range of 320 to 535 mg/L corresponds to OD 585 and 635 nm in the range of 0.157 to 0.207 and 0.142 to 0.189, respectively).

COD of the sample was estimated to be 15,801 mg/L. (By Merck method and read on photometer).

Based on the color of the reaction mixture, COD of the sample was estimated to be around 12000 mg/L. On the basis of the dilution method and the spectrophotometric reading at OD 585 and OD 635 of the sample, COD was estimated to be 13389 and 13506 mg/l respectively. A comparison with the COD value calculated through Merck method reveals the following relation i.e. Our COD value at (OD 585)×1.18=COD value (Merck Method) or our COD value (at OD 635)×1.17=COD value (Merck Method).

Hence for a preliminary estimate of COD value color of the standard reaction mixture based on a range of glucose concentrations can be used as a reference. For samples, with COD concentration of 300 to 500 mg/L, OD 585 or OD 635 can be recorded for obtaining more precise values.

TABLE 39

Correlation between COD concentration, color of the reaction mixture and their OD at different wave lengths.

| COD (mg/L) 1 | Sample dilution (Times) 2 | Color of the reaction mixture 3 | OD 4 | Estimated COD (mg/L) 5 | Estimated final COD (mg/L) (Col. 2 × 5) 6 |
|---|---|---|---|---|---|
| Values at OD 585 nm | | | | | |
| Glucose: | | | | | |
| 320 | NA | C300 | 0.165 | NA | NA |
| 426 | NA | C400 | 0.193 | NA | NA |
| 535 | NA | C550 | 0.213 | NA | NA |
| Sample: Palm oil Mill effluent (as such) | | | | | |
| Nil | C10000 | — | >10,000 | >10,000 | |
| 10 | C1900 | 0.394 | ≅1900 | ≅19,000# | |
| 30 | C400 | 0.165 | 446.3 | 13389 | |
| Values at OD 635 nm | | | | | |
| Glucose: | | | | | |
| 320 | NA | C300 | 0.148 | NA | NA |
| 426 | NA | C400 | 0.172 | NA | NA |
| 535 | NA | C550 | 0.191 | NA | NA |
| Sample: Palm oil Mill effluent (as such) | | | | | |
| Nil | C10000 | — | >10000 | >10000 | |
| 10 | C1900 | 0.360 | ≅1900 | ≅19000# | |
| 30 | C400 | 0.148 | 450.2 | 13506 | |

COD as deducible from Table 2 given in Example 2.
D: Dark.
T: Turbid.
*OD out of range.
NA: Not applicable.
Samples are diluted to get an OD 585 in the range of 0.130 to 0.175 and OD 635 in the range of 0.120 to 0.160, to obtain a COD value in the range of 320 to 535 mg/L. (Based on the Tables 3 to 15 given in Examples 3 to 15).

EXAMPLE 40

Dissolved 0.15 g glucose in 25 mL distilled water. Aliquots from the stock solution were taken and diluted with water to achieve different COD concentrations in the range of 320 to 535 mg/L. A 30 mL sample of Palm oil mill effluent (ssp) was taken. Weighed 0.02 g $HgSO_4$ in separate 15 mL test tubes. 1.0 mL of glucose solution and sample were added to each test tube separately and mixed well. 0.5 mL of $K_2Cr_2O_7$ was added to each sample. 1.5 mL $H_2SO_4$ silver sulphate reagent was added slowly with continuous shaking. The color of the reaction mixture was noted down visually within 15 sec of incubation and also recorded spectrophotometrically at 585 and 635 nm against air. An approximate COD value of the sample was estimated from the color of standard reaction mixture prepared with glucose as reference material in the COD range of 200 to 100000 mg/L. OD 585 and OD 635 of the reaction mixture was read spectrophotometrically. OD 585 and 635 nm in the range of 0.130 to 0.175 and 0.120 to 0.160 respectively were considered and calculated with reference to glucose standard. (Glucose COD in the range of 320 to 535 mg/L corresponds to OD 585 and 635 nm in the range of 0.157 to 0.207 and 0.142 to 0.189, respectively).

COD of the sample was estimated to be 1129.6 mg/L. (By Merck method and read on photometer).

Based on the color of the reaction mixture, COD of the sample was estimated to be around 800 mg/L. On the basis of the dilution method and the spectrophotometric reading at OD 585 and OD 635 of the sample, COD was estimated to be 970 and 950 mg/l respectively. A comparison with the COD value calculated through Merck method reveals the following relation i.e. Our COD value (at OD 585)×1.16= COD value (Merck Method) or our COD value (at OD 635)×1.19=COD value (Merck Method).

Hence for a preliminary estimate of COD value color of the standard reaction mixture based on a range of glucose concentrations can be used as a reference. For samples, with COD concentration of 300 to 500 mg/L, OD 585 or OD 635 can be recorded for obtaining more precise values.

TABLE 40

Correlation between COD concentration, color of the reaction mixture and their OD at different wave lengths.

| COD (mg/L) 1 | Sample dilution (Times) 2 | Color of the reaction mixture 3 | OD 4 | Estimated COD (mg/L) 5 | Estimated final COD (mg/L) (Col. 2 × 5) 6 |
|---|---|---|---|---|---|
| Values at OD 585 nm | | | | | |
| Glucose: | | | | | |
| 320 | NA | C300 | 0.163 | NA | NA |
| 426 | NA | C400 | 0.176 | NA | NA |
| 535 | NA | C550 | 0.226 | NA | NA |
| Sample: Palm oil Mill effluent (ssp) | | | | | |
| | Nil | C1500 | 0.263 | ≅1500 | ≅1500# |
| | 2 | C400 | 0.171 | 485 | 970 |
| Values at OD 635 nm | | | | | |
| Glucose: | | | | | |
| 320 | NA | C300 | 0.146 | NA | NA |
| 426 | NA | C400 | 0.159 | NA | NA |
| 535 | NA | C550 | 0.205 | NA | NA |

TABLE 40-continued

Correlation between COD concentration, color of the reaction mixture and their OD at different wave lengths.

| COD (mg/L) 1 | Sample dilution (Times) 2 | Color of the reaction mixture 3 | OD 4 | Estimated COD (mg/L) 5 | Estimated final COD (mg/L) (Col. 2 × 5) 6 |
|---|---|---|---|---|---|
| Sample: Palm oil Mill effluent (ssp) | | | | | |
| | Nil | C1500 | 0.242 | ≅1500 | ≅1500# |
| | 2 | C400 | 0.152 | 475 | 950 |

COD as deducible from Table 2 given in Example 2.
D: Dark.
T: Turbid.
*OD out of range.
NA: Not applicable.
Samples are diluted to get an OD 585 in the range of 0.130 to 0.175 and OD 635 in the range of 0.120 to 0.160, to obtain a COD value in the range of 320 to 535 mg/L. (Based on the Tables 3 to 15 given in Examples 3 to 15).

EXAMPLE 41

Dissolved 0.15 g glucose in 25 mL distilled water. Aliquots from the stock solution were taken and diluted with water to achieve different COD concentrations in the range of 320 to 535 mg/L. A 30 mL sample of Damaged wheat grain and POME (as such) was taken. Weighed 0.02 g $HgSO_4$ in separate 15 mL test tubes. 1.0 mL of glucose solution and sample were added to each test tube separately and mixed well. 0.5 mL of $K_2Cr_2O_7$ was added to each sample. 1.5 mL $H_2SO_4$ silver sulphate reagent was added slowly with continuous shaking. The color of the reaction mixture was noted down visually within 15 sec of incubation and also recorded spectrophotometrically at 585 and 635 nm against air. An approximate COD value of the sample was estimated from the color of standard reaction mixture prepared with glucose as reference material in the COD range of 200 to 100000 mg/L. OD 585 and OD 635 of the reaction mixture was read spectrophotometrically. OD 585 and 635 nm in the range of 0.130 to 0.175 and 0.120 to 0.160 respectively were considered and calculated with reference to glucose standard. (Glucose COD in the range of 320 to 535 mg/L corresponds to OD 585 and 635 nm in the range of 0.157 to 0.207 and 0.142 to 0.189, respectively).

COD of the sample was estimated to be 9706 mg/L. (By Merck method and read on photometer).

Based on the color of the reaction mixture, COD of the sample was estimated to be around 9000 mg/L. On the basis of the dilution method and the spectrophotometric reading at OD 585 and OD 635 of the sample, COD was estimated to be 7660 and 7567 mg/l respectively. A comparison with the COD value calculated through Merck method reveals the following relation i.e. Our COD value (at OD 585)×1.27= COD value (Merck Method) or our COD value (at OD 635)×1.12.

Hence for a preliminary estimate of COD value color of the standard reaction mixture based on a range of glucose concentrations can be used as a reference. For samples, with COD concentration of 300 to 500 mg/L, OD 585 or OD 635 can be recorded for obtaining more precise values.

TABLE 41

Correlation between COD concentration, color of the reaction mixture and their OD at different wave lengths.

| COD (mg/L) 1 | Sample dilution (Times) 2 | Color of the reaction mixture 3 | OD 4 | Estimated COD (mg/L) 5 | Estimated final COD (mg/L) (Col. 2 × 5) 6 |
|---|---|---|---|---|---|
| Values at OD 585 nm ||||||
| Glucose: ||||||
| 320 | NA | C300 | 0.165 | NA | NA |
| 426 | NA | C400 | 0.193 | NA | NA |
| 535 | NA | C550 | 0.213 | NA | NA |
| Sample: DWS (S3) + POME (as such) ||||||
| Nil | | C10000 | 1.231 | >10,000 | >10,000 |
| 10 | | C1500 | 0.256 | ≅1500 | ≅15,000 |
| 20 | | C450 | 0.186 | ≅450 | ≅9000# |
| 25 | | C300 | 0.132 | 306.4 | 7660 |
| Values at OD 635 nm ||||||
| Glucose: ||||||
| 320 | NA | C300 | 0.148 | NA | NA |
| 426 | NA | C400 | 0.172 | NA | NA |
| 535 | NA | C550 | 0.191 | NA | NA |
| Sample: DWS (S3) + POME (as such) ||||||
| Nil | | C10000 | 0.994 | 10,000 | >10,000 |
| 10 | | C1500 | 0.221 | ≅1500 | ≅15,000 |
| 20 | | C450 | 0.165 | ≅450 | ≅9000# |
| 25 | | C300 | 0.117 | 302.6 | 7567 |

COD as deducible from Table 2 given in Example 2.
D: Dark.
T: Turbid.
*OD out of range.
NA: Not applicable.
Samples are diluted to get an OD 585 in the range of 0.130 to 0.175 and OD 635 in the range of 0.120 to 0.160, to obtain a COD value in the range of 320 to 535 mg/L. (Based on the Tables 3 to 15 given in Examples 3 to 15).

EXAMPLE 42

Dissolved 0.15 g glucose in 25 mL distilled water. Aliquots from the stock solution were taken and diluted with water to achieve different COD concentrations in the range of 320 to 535 mg/L. A 30 mL sample of Damaged wheat grain and POME (ssp) was taken. Weighed 0.02 g $HgSO_4$ in separate 15 mL test tubes. 1.0 mL of glucose solution and sample were added to each test tube separately and mixed well. 0.5 mL of $K_2Cr_2O_7$ was added to each sample. 1.5 mL $H_2SO_4$ silver sulphate reagent was added slowly with continuous shaking. The color of the reaction mixture was noted down visually within 15 sec of incubation and also recorded spectrophotometrically at 585 and 635 nm against air. An approximate COD value of the sample was estimated from the color of standard reaction mixture prepared with glucose as reference material in the COD range of 200 to 100000 mg/L. OD 585 and OD 635 of the reaction mixture was read spectrophotometrically. OD 585 and 635 nm in the range of 0.130 to 0.175 and 0.120 to 0.160 respectively were considered and calculated with reference to glucose standard. (Glucose COD in the range of 320 to 535 mg/L corresponds to OD 585 and 635 nm in the range of 0.157 to 0.207 and 0.142 to 0.189, respectively).

COD of the sample was estimated to be 4427.5 mg/L. (By Merck method and read on photometer).

Based on the color of the reaction mixture, COD of the sample was estimated to be around 4000 mg/L. On the basis of the dilution method and the spectrophotometric reading at OD 585 and OD 635 of the sample, COD was estimated to be 4068 and 3936 mg/l respectively. A comparison with the COD value calculated through Merck method reveals the following relation i.e. Our COD value (at OD 585)×1.09= COD value (Merck Method) or our COD value (at OD 635)×1.12.

Hence for a preliminary estimate of COD value color of the standard reaction mixture based on a range of glucose concentrations can be used as a reference. For samples, with COD concentration of 300 to 500 mg/L, OD 585 or OD 635 can be recorded for obtaining more precise values.

TABLE 42

Correlation between COD concentration, color of the reaction mixture and their OD at different wave lengths.

| COD (mg/L) 1 | Sample dilution (Times) 2 | Color of the reaction mixture 3 | OD 4 | Estimated COD (mg/L) 5 | Estimated final COD (mg/L) (Col. 2 × 5) 6 |
|---|---|---|---|---|---|
| Values at OD 585 nm ||||||
| Glucose: ||||||
| 320 | NA | C300 | 0.165 | NA | NA |
| 426 | NA | C400 | 0.193 | NA | NA |
| 535 | NA | C550 | 0.213 | NA | NA |
| Sample: DWS (S3) + POME (ssp) ||||||
| Nil | | C1500 | 0.520 | >1500 | >1500 |
| 10 | | C400 | 0.185 | ≅400 | ≅4000# |
| 12 | | C300 | 0.146 | 339 | 4068 |
| Values at OD 635 nm ||||||
| Glucose: ||||||
| 320 | NA | C300 | 0.148 | NA | NA |
| 426 | NA | C400 | 0.172 | NA | NA |
| 535 | NA | C550 | 0.191 | NA | NA |
| Sample: DWS (S3) + POME (ssp) ||||||
| Nil | | C1500 | 0.427 | >1500 | >1500 |
| 10 | | C400 | 0.165 | ≅400 | >4000# |
| 12 | | C300 | 0.127 | 328 | 3936 |

COD as deducible from Table 2 given in Example 2.
D: Dark.
T: Turbid.
*OD out of range.
NA: Not applicable.
Samples are diluted to get an OD 585 in the range of 0.130 to 0.175 and OD 635 in the range of 0.120 to 0.160, to obtain a COD value in the range of 320 to 535 mg/L. (Based on the Tables 3 to 15 given in Examples 3 to 15).

EXAMPLE 43

Dissolved 0.15 g glucose in 25 mL distilled water. Aliquots from the stock solution were taken and diluted with water to achieve different COD concentrations in the range of 320 to 535 mg/L. A 30 mL sample of Tea (as such) was taken. Weighed 0.02 g $HgSO_4$ in separate 15 mL test tubes. 1.0 mL of glucose solution and sample were added to each test tube separately and mixed well. 0.5 mL of $K_2Cr_2O_7$ was added to each sample. 1.5 mL $H_2SO_4$ silver sulphate reagent was added slowly with continuous shaking. The color of the reaction mixture was noted down visually within 15 sec of incubation and also recorded spectrophotometrically at 585 and 635 nm against air. An approximate COD value of the sample was estimated from the color of standard reaction mixture prepared with glucose as reference material in the COD range of 200 to 100000 mg/L. OD 585 and 635 of the reaction mixture was read spectrophotometrically. OD 585 and 635 nm in the range of 0.130 to 0.175 and 0.120 to 0.160 respectively were considered and calculated with reference to glucose standard. (Glucose COD in the range of 320 to 535 mg/L corresponds to OD 585 and 635 nm in the range of 0.157 to 0.207 and 0.142 to 0.189, respectively).

COD of the sample was estimated to be 74,589 mg/L. (By Merck method and read on photometer).

Based on the color of the reaction mixture, COD of the sample was estimated to be around 90000 mg/L. On the basis of the dilution method and the spectrophotometric reading at OD 585 and OD 635 of the sample, COD was estimated to be 101750 and 102000 mg/l respectively. A comparison with the COD value calculated through Merck method reveals the following relation i.e. Our COD value at (OD 585 or OD 635)×0.73=COD value (Merck Method).

Hence, for a preliminary estimate of COD value color of the standard reaction mixture based on a range of glucose concentrations can be used as a reference. For samples, with COD concentration of 300 to 500 mg/L, OD 585 or OD 635 can be recorded for obtaining more precise values.

Tea (as such)

TABLE 43

Correlation between COD concentration, color of the reaction mixture and their OD at different wave lengths.

| COD (mg/L) 1 | Sample dilution (Times) 2 | Color of the reaction mixture 3 | OD 4 | Estimated COD (mg/L) 5 | Estimated final COD (mg/L) (Col. 2 × 5) 6 |
|---|---|---|---|---|---|
| Values at OD 585 nm ||||||
| Glucose: ||||||
| 320 | NA | C300 | 0.159 | NA | NA |
| 426 | NA | C400 | 0.186 | NA | NA |
| 535 | NA | C550 | 0.223 | NA | NA |
| Sample: TEA (as such) ||||||
| | Nil | C10000 | — | >10,000 | >10,000 |
| | 10 | C10000 | — | >10,000 | >1,00,000 |
| | 100 | C1900 | 0.267 | ≅1900 | ≅1,90,000 |
| | 111.1 | C1300 | 0.245 | ≅1300 | ≅1,44,430 |
| | 166.7 | C500 | 0.206 | ≅550 | ≅91,685 |
| | 200 | C400 | 0.175 | ≅450 | ≅90,000# |
| | 250 | C300 | 0.145 | 407 | 101750 |
| Values at OD 635 nm ||||||
| Glucose: ||||||
| 320 | NA | C300 | 0.141 | NA | NA |
| 426 | NA | C400 | 0.164 | NA | NA |
| 535 | NA | C550 | 0.198 | NA | NA |
| Sample: TEA (as such) ||||||
| | Nil | C10000 | — | >10,000 | >10,000 |
| | 10 | C10000 | — | >10,000 | >1,00,000 |
| | 100 | C1900 | 0.237 | ≅1900 | ≅1,90,000 |
| | 111.1 | C1300 | 0.214 | ≅1300 | ≅1,44,430 |

TABLE 43-continued

Correlation between COD concentration, color of the reaction mixture and their OD at different wave lengths.

| COD (mg/L) 1 | Sample dilution (Times) 2 | Color of the reaction mixture 3 | OD 4 | Estimated COD (mg/L) 5 | Estimated final COD (mg/L) (Col. 2 × 5) 6 |
|---|---|---|---|---|---|
| | 166.7 | C500 | 0.182 | ≅550 | ≅91,685 |
| | 200 | C400 | 0.155 | ≅450 | ≅90,000# |
| | 250 | C300 | 0.128 | 408 | 102000 |

COD as deducible from Table 2 given in Example 2.
D: Dark.
T: Turbid.
*OD out of range.
NA: Not applicable.
Samples are diluted to get an OD 585 in the range of 0.130 to 0.175 and OD 635 in the range of 0.120 to 0.160, to obtain a COD value in the range of 320 to 535 mg/L. (Based on the Tables 3 to 15 given in Examples 3 to 15).

EXAMPLE 44

Dissolved 0.15 g glucose in 25 mL distilled water. Aliquots from the stock solution were taken and diluted with water to achieve different COD concentrations in the range of 320 to 535 mg/L. A 30 mL sample of Tea (ssp) was taken. Weighed 0.02 g $HgSO_4$ in separate 15 mL test tubes. 1.0 mL of glucose solution and sample were added to each test tube separately and mixed well. 0.5 mL of $K_2Cr_2O_7$ was added to each sample. 1.5 mL $H_2SO_4$ silver sulphate reagent was added slowly with continuous shaking. The color of the reaction mixture was noted down visually within 15 sec of incubation and also recorded spectrophotometrically at 585 and 635 nm against air. An approximate COD value of the sample was estimated from the color of standard reaction mixture prepared with glucose as reference material in the COD range of 200 to 100000 mg/L. OD 585 and OD 635 of the reaction mixture was read spectrophotometrically. OD 585 and 635 nm in the range of 0.130 to 0.175 and 0.120 to 0.160 respectively were considered and calculated with reference to glucose standard. (Glucose COD in the range of 320 to 535 mg/L corresponds to OD 585 and 635 nm in the range of 0.157 to 0.207 and 0.142 to 0.189, respectively).

COD of the sample was estimated to be 67,528 mg/L. (By Merck method and read on photometer).

Based on the color of the reaction mixture, COD of the sample was estimated to be around 75015 mg/L. On the basis of the dilution method and the spectrophotometric reading at OD 585 and OD 635 of the sample, COD was estimated to be 81380 and 18380 mg/l respectively. A comparison with the COD value calculated through Merck method reveals the following relation i.e. Our COD value (at OD 585 or OD 635)×0.83=COD value (Merck Method).

Hence for a preliminary estimate of COD value color of the standard reaction mixture based on a range of glucose concentrations can be used as a reference. For samples, with COD concentration of 300 to 500 mg/L, OD 585 or OD 635 can be recorded for obtaining more precise values.

Tea (ssp)

TABLE 44

Correlation between COD concentration, color of the reaction mixture and their OD at different wave lengths.

| COD (mg/L) 1 | Sample dilution (Times) 2 | Color of the reaction mixture 3 | OD 4 | Estimated COD (mg/L) 5 | Estimated final COD (mg/L) (Col. 2 × 5) 6 |
|---|---|---|---|---|---|
| Values at OD 585 nm | | | | | |
| Glucose: | | | | | |
| 320 | NA | C300 | 0.159 | NA | NA |
| 426 | NA | C400 | 0.186 | NA | NA |
| 535 | NA | C550 | 0.223 | NA | NA |
| Sample: TEA (ssp) | | | | | |
| | Nil | C10000 | — | >10,000 | ≅>10,000 |
| | 10 | C10000 | — | >10,000 | >1,00,000 |
| | 100 | C1800 | 0.244 | ≅1800 | ≅1,80,000 |
| | 125 | C550 | 0.222 | ≅550 | ≅68,750 |
| | 166.7 | C450 | 0.173 | ≅450 | ≅75,015# |
| | 200 | C300 | 0.145 | 407 | 81380 |
| Values at OD 635 nm | | | | | |
| Glucose: | | | | | |
| 320 | NA | C300 | 0.141 | NA | NA |
| 426 | NA | C400 | 0.164 | NA | NA |
| 535 | NA | C550 | 0.198 | NA | NA |
| Sample: TEA (ssp) | | | | | |
| | Nil | C10000 | — | >10,000 | ≅>10,000 |
| | 10 | C10000 | — | >10,000 | >1,00,000 |
| | 100 | C1800 | 0.216 | ≅1800 | ≅1,80,000 |
| | 125 | C550 | 0.190 | ≅550 | ≅68,750 |
| | 166.7 | C450 | 0.152 | ≅450 | ≅75,015# |
| | 200 | C300 | 0.128 | 408 | 81700 |

COD as deducible from Table 2 given in Example 2.
D: Dark.
T: Turbid.
*OD out of range.
NA: Not applicable.
Samples are diluted to get an OD 585 in the range of 0.130 to 0.175 and OD 635 in the range of 0.120 to 0.160, to obtain a COD value in the range of 320 to 535 mg/L. (Based on the Tables 3 to 15 given in Examples 3 to 15).

EXAMPLE 45

Dissolved 0.15 g glucose in 25 mL distilled water. Aliquots from the stock solution were taken and diluted with water to achieve different COD concentrations in the range of 320 to 535 mg/L. A 30 mL sample of Apple pomace (ssp) was taken. Weighed 0.02 g $HgSO_4$ in separate 15 mL test tubes. 1.0 mL of glucose solution and sample were added to each test tube separately and mixed well. 0.5 mL of $K_2Cr_2O_7$ was added to each sample. 1.5 mL $H_2SO_4$ silver sulphate reagent was added slowly with continuous shaking. The color of the reaction mixture was noted down visually within 15 sec of incubation and also recorded spectrophotometrically at 585 and 635 nm against air. An approximate COD value of the sample was estimated from the color of standard reaction mixture prepared with glucose as reference material in the COD range of 200 to 100000 mg/L. OD 585 and OD 635 of the reaction mixture was read spectrophotometrically. OD 585 and 635 nm in the range of 0.130 to 0.175 and 0.120 to 0.160 respectively were considered and calculated with reference to glucose standard. (Glucose COD in the range of 320 to 535 mg/L corresponds to OD 585 and 635 nm in the range of 0.157 to 0.207 and 0.142 to 0.189, respectively).

COD of the sample was estimated to be 39,284 mg/L. (By Merck method and read on photometer).

Based on the color of the reaction mixture, COD of the sample was estimated to be around 30760 mg/L. On the basis of the dilution method and the spectrophotometric reading at OD 585 and OD 635 of the sample, COD was estimated to be 43000 and 43500 mg/l respectively. A comparison with the COD value calculated through Merck method reveals the following relation i.e. Our COD value (at OD 585)×0.91=COD value (Merck Method) or our COD value (at OD 635)×435=COD value (Merck Method).

Hence for a preliminary estimate of COD value color of the standard reaction mixture based on a range of glucose concentrations can be used as a reference. For samples, with COD concentration of 300 to 500 mg/L, OD 585 or OD 635 can be recorded for obtaining more precise values.

Apple Pomace (ssp)

TABLE 45

Correlation between COD concentration, color of the reaction mixture and their OD at different wave lengths.

| COD (mg/L) 1 | Sample dilution (Times) 2 | Color of the reaction mixture 3 | OD 4 | Estimated COD (mg/L) 5 | Estimated final COD (mg/L) (Col. 2 × 5) 6 |
|---|---|---|---|---|---|
| Values at OD 585 nm | | | | | |
| Glucose: | | | | | |
| 320 | NA | C300 | 0.159 | NA | NA |
| 426 | NA | C400 | 0.187 | NA | NA |
| 535 | NA | C550 | 0.210 | NA | NA |
| Sample: APPLE POMACE (ssp) | | | | | |
| | Nil | C10000 | — | >10,000 | >10,000 |
| | 10 | C1600 | 0.392 | ≅1600 | ≅16,000 |
| | 16.7 | C800 | 0.354 | ≅800 | ≅13,360 |
| | 50 | C550 | 0.244 | ≅550 | ≅27,500 |
| | 76.9 | C400 | 0.178 | ≅400 | ≅30,760# |
| | 100 | C300 | 0.154 | 430 | 43000 |
| Values at OD 635 nm | | | | | |
| Glucose: | | | | | |
| 320 | NA | C300 | 0.141 | NA | NA |
| 426 | NA | C400 | 0.167 | NA | NA |
| 535 | NA | C550 | 0.191 | NA | NA |
| Sample: APPLE POMACE (ssp) | | | | | |
| | Nil | C10000 | — | >10,000 | >10,000 |
| | 10 | C1600 | 0.336 | ≅1600 | ≅16,000 |
| | 16.7 | C800 | 0.317 | ≅800 | ≅13,360 |
| | 50 | C550 | 0.217 | ≅550 | ≅27,500 |
| | 76.9 | C400 | 0.159 | ≅400 | ≅30,760# |
| | 100 | C300 | 0.139 | 435 | 45000 |

COD as deducible from Table 2 given in Example 2.
D: Dark.
T: Turbid.
*OD out of range.
NA: Not applicable.
Samples are diluted to get an OD 585 in the range of 0.130 to 0.175 and OD 635 in the range of 0.120 to 0.160, to obtain a COD value in the range of 320 to 535 mg/L. (Based on the Tables 3 to 15 given in Examples 3 to 15).

EXAMPLE 46

Dissolved 0.15 g glucose in 25 mL distilled water. Aliquots from the stock solution were taken and diluted with water to achieve different COD concentrations in the range of 320 to 535 mg/L. A 30 mL sample of Tea and Apple pomace (as such) was taken. Weighed 0.02 g $HgSO_4$ in separate 15 mL test tubes. 1.0 mL of glucose solution and sample were added to each test tube separately and mixed well. 0.5 mL of $K_2Cr_2O_7$ was added to each sample. 1.5 mL $H_2SO_4$ silver sulphate reagent was added slowly with continuous shaking. The color of the reaction mixture was noted down visually within 15 sec of incubation and also recorded spectrophotometrically at 585 and 635 nm against air. An approximate COD value of the sample was estimated from the color of standard reaction mixture prepared with glucose as reference material in the COD range of 200 to 100000 mg/L. OD 585 and OD 635 of the reaction mixture was read spectrophotometrically. OD 585 and 635 nm in the range of 0.130 to 0.175 and 0.120 to 0.160 respectively were considered and calculated with reference to glucose standard. (Glucose COD in the range of 320 to 535 mg/L corresponds to OD 585 and 635 nm in the range of 0.157 to 0.207 and 0.142 to 0.189, respectively).

COD of the sample was estimated to be 56,948 mg/L. (By Merck method and read on photometer).

Based on the color of the reaction mixture, COD of the sample was estimated to be around 40000 mg/L. On the basis of the dilution method and the spectrophotometric reading at OD 585 and OD 635 of the sample, COD was estimated to be 68441 and 681334 mg/l respectively. A comparison with the COD value calculated through Merck method reveals the following relation i.e. Our COD value (at OD 585)×0.83=COD value (Merck Method) or our COD value (at OD 635)×0.84=COD value (Merck Method).)

Hence for a preliminary estimate of COD value color of the standard reaction mixture based on a range of glucose concentrations can be used as a reference. For samples, with COD concentration of 300 to 500 mg/L, OD 585 or OD 635 can be recorded for obtaining more precise values.

Tea+Apple Pomace (as such)

TABLE 46

Correlation between COD concentration, color of the reaction mixture and their OD at different wave lengths.

| COD (mg/L) 1 | Sample dilution (Times) 2 | Color of the reaction mixture 3 | OD 4 | Estimated COD (mg/L) 5 | Estimated final COD (mg/L) (Col. 2 × 5) 6 |
|---|---|---|---|---|---|
| Values at OD 585 nm | | | | | |
| Glucose: | | | | | |
| 320 | NA | C300 | 0.157 | NA | NA |
| 426 | NA | C400 | 0.176 | NA | NA |
| 535 | NA | C550 | 0.202 | NA | NA |
| Sample: TEA + APPLE POMACE (as such) | | | | | |
| | Nil | C10000 | — | >10,000 | >10,000 |
| | 10 | C1500 | 0.603 | ≅1500 | ≅15,000 |
| | 50 | C700 | 0.295 | ≅700 | ≅35,000 |
| | 100 | C400 | 0.187 | ≅400 | ≅40,000# |
| | 153.8 | C450 | 0.150 | 445 | 68441 |
| Values at OD 635 nm | | | | | |
| Glucose: | | | | | |
| 320 | NA | C300 | 0.142 | NA | NA |
| 426 | NA | C400 | 0.155 | NA | NA |
| 535 | NA | C550 | 0.182 | NA | NA |
| Sample: TEA + APPLE POMACE (as such) | | | | | |
| | Nil | C10000 | — | >10,000 | >10,000 |
| | 10 | C1500 | 0.465 | ≅1500 | ≅15,000 |
| | 50 | C700 | 0.262 | ≅700 | ≅35,000 |

TABLE 46-continued

Correlation between COD concentration, color of the reaction mixture and their OD at different wave lengths.

| COD (mg/L) 1 | Sample dilution (Times) 2 | Color of the reaction mixture 3 | OD 4 | Estimated COD (mg/L) 5 | Estimated final COD (mg/L) (Col. 2 × 5) 6 |
|---|---|---|---|---|---|
| | 100 | C400 | 0.168 | ≅400 | ≅40,000# |
| | 153.8 | C400 | 0.122 | 443 | 68134 |

COD as deducible from Table 2 given in Example 2.
D: Dark.
T: Turbid.
*OD out of range.
NA: Not applicable.
Samples are diluted to get an OD 585 in the range of 0.130 to 0.175 and OD 635 in the range of 0.120 to 0.160, to obtain a COD value in the range of 320 to 535 mg/L. (Based on the Tables 3 to 15 given in Examples 3 to 15).

EXAMPLE 47

Dissolved 0.15 g glucose in 25 mL distilled water. Aliquots from the stock solution were taken and diluted with water to achieve different COD concentrations in the range of 320 to 535 mg/L. A 30 mL sample of Tea+Apple pomace (ssp) and POME was taken. Weighed 0.02 g $HgSO_4$ in separate 15 mL test tubes. 1.0 mL of glucose solution and sample were added to each test tube separately and mixed well. 0.5 mL of $K_2Cr_2O_7$ was added to each sample. 1.5 mL $H_2SO_4$ silver sulphate reagent was added slowly with continuous shaking. The color of the reaction mixture was noted down visually within 15 sec of incubation and also recorded spectrophotometrically at 585 and 635 nm against air. An approximate COD value of the sample was estimated from the color of standard reaction mixture prepared with glucose as reference material in the COD range of 200 to 100000 mg/L. OD 585 and OD 635 of the reaction mixture was read spectrophotometrically. OD 585 and 635 nm in the range of 0.130 to 0.175 and 0.120 to 0.160 respectively were considered and calculated with reference to glucose standard. (Glucose COD in the range of 320 to 535 mg/L corresponds to OD 585 and 635 nm in the range of 0.157 to 0.207 and 0.142 to 0.189, respectively).

COD of the sample was estimated to be 60,398 mg/L. (By Merck method and read on photometer).

Based on the color of the reaction mixture, COD of the sample was estimated to be around 45000 mg/L. On the basis of the dilution method and the spectrophotometric reading at OD 585 and OD 635 of the sample, COD was estimated to be 66,134 and 67,364 mg/l respectively. A comparison with the COD value calculated through Merck method reveals the following relation i.e. Our COD value (at OD 585)×0.91=COD value (Merck Method) or our COD value (at OD 635)×0.90=COD value (Merck Method).)

Hence for a preliminary estimate of COD value color of the standard reaction mixture based on a range of glucose concentrations can be used as a reference. For samples, with COD concentration of 300 to 500 mg/L, OD 585 or OD 635 can be recorded for obtaining more precise values.

Tea+Apple Pomace (ssp)

TABLE 47

Correlation between COD concentration, color of the reaction mixture and their OD at different wave lengths.

| COD (mg/L) 1 | Sample dilution (Times) 2 | Color of the reaction mixture 3 | OD 4 | Estimated COD (mg/L) 5 | Estimated final COD (mg/L) (Col. 2 × 5) 6 |
|---|---|---|---|---|---|
| \multicolumn{6}{c}{Values at OD 585 nm} | | | | | |
| Glucose: | | | | | |
| 320 | NA | C300 | 0.157 | NA | NA |
| 426 | NA | C400 | 0.176 | NA | NA |
| 535 | NA | C550 | 0.202 | NA | NA |
| Sample: TEA + APPLE POMACE (ssp) | | | | | |
|  | Nil | C10000 | — | >10,000 | >10,000 |
|  | 10 | C1400 | 0.621 | ≅1400 | ≅14,000 |
|  | 50 | C800 | 0.284 | ≅800 | ≅40,000 |
|  | 100 | C450 | 0.181 | ≅450 | ≅45,000 |
|  | 153.8 | C400 | 0.145 | 430 | 66,134 |
| Values at OD 635 nm | | | | | |
| Glucose: | | | | | |
| 320 | NA | C300 | 0.142 | NA | NA |
| 426 | NA | C400 | 0.155 | NA | NA |
| 535 | NA | C550 | 0.182 | NA | NA |
| Sample: TEA + APPLE POMACE (ssp) | | | | | |
|  | Nil | C10000 | — | >10,000 | >10,000 |
|  | 10 | C1400 | 0.473 | ≅1400 | ≅14,000 |
|  | 50 | C800 | 0.284 | ≅800 | ≅40,000 |
|  | 100 | C450 | 0.159 | ≅450 | ≅45,000 |
|  | 153.8 | C400 | 0.130 | 438 | 67,364 |

COD as deducible from Table 2 given in Example 2.
D: Dark.
T: Turbid.
*OD out of range.
NA: Not applicable.
Samples are diluted to get an OD 585 in the range of 0.130 to 0.175 and OD 635 in the range of 0.120 to 0.160, to obtain a COD value in the range of 320 to 535 mg/L. (Based on the Tables 3 to 15 given in Examples 3 to 15).

EXAMPLE 48

Dissolved 0.15 g glucose in 25 mL distilled water. Aliquots from the stock solution were taken and diluted with water to achieve different COD concentrations in the range of 320 to 535 mg/L. A 30 mL sample of Digested POME (as such) was taken. Weighed 0.02 g $HgSO_4$ in separate 15 mL test tubes. 1.0 mL of glucose solution and sample were added to each test tube separately and mixed well. 0.5 mL of $K_2Cr_2O_7$ was added to each sample. 1.5 mL $H_2SO_4$ silver sulphate reagent was added slowly with continuous shaking. The color of the reaction mixture was noted down visually within 15 sec of incubation and also recorded spectrophotometrically at 585 and 635 nm against air. An approximate COD value of the sample was estimated from the color of standard reaction mixture prepared with glucose as reference material in the COD range of 200 to 100000 mg/L. OD 585 and OD 635 of the reaction mixture was read spectrophotometrically. OD 585 and 635 nm in the range of 0.130 to 0.175 and 0.120 to 0.160 respectively were considered and calculated with reference to glucose standard. (Glucose COD in the range of 320 to 535 mg/L corresponds to OD 585 and 635 nm in the range of 0.157 to 0.207 and 0.142 to 0.189, respectively).

COD of the sample was estimated to be 5993.8 mg/L. (By Merck method and read on photometer).

Based on the color of the reaction mixture, COD of the sample was estimated to be around 1700 mg/L. On the basis of the dilution method and the spectrophotometric reading at OD 585 and OD 635 of the sample, COD was estimated to be 3120 and 3160 mg/l respectively. A comparison with the COD value calculated through Merck method reveals the following relation i.e. Our COD value (at OD 585)×1.92= COD value (Merck Method) or our COD value (at OD 635)×1.90=COD value (Merck Method).)

Hence for a preliminary estimate of COD value color of the standard reaction mixture based on a range of glucose concentrations can be used as a reference. For samples, with COD concentration of 300 to 500 mg/L, OD 585 or OD 635 can be recorded for obtaining more precise values.

Digested POME (as such)

TABLE 48

Correlation between COD concentration, color of the reaction mixture and their OD at different wave lengths.

| COD (mg/L) 1 | Sample dilution (Times) 2 | Color of the reaction mixture 3 | OD 4 | Estimated COD (mg/L) 5 | Estimated final COD (mg/L) (Col. 2 × 5) 6 |
|---|---|---|---|---|---|
| Values at OD 585 nm | | | | | |
| Glucose: | | | | | |
| 320 | NA | C300 | 0.162 | NA | NA |
| 426 | NA | C400 | 0.189 | NA | NA |
| 535 | NA | C550 | 0.207 | NA | NA |
| Sample: Digested POME (as such) | | | | | |
|  | Nil | C1700 | 1.021 | ≅1700 | ≅1700# |
|  | 10 | C250 | 0.132 | 312 | 3120 |
| Values at OD 635 nm | | | | | |
| Glucose: | | | | | |
| 320 | NA | C300 | 0.146 | NA | NA |
| 426 | NA | C400 | 0.171 | NA | NA |
| 535 | NA | C300 | 0.187 | NA | NA |
| Sample: Digested POME (as such) | | | | | |
|  | Nil | C1700 | 0.889 | ≅1700 | ≅1700# |
|  | 10 | C250 | 0.120 | 316 | 3160 |

COD as deducible from Table 2 given in Example 2.
D: Dark.
T: Turbid.
*OD out of range.
NA: Not applicable.
Samples are diluted to get an OD 585 in the range of 0.130 to 0.175 and OD 635 in the range of 0.120 to 0.160, to obtain a COD value in the range of 320 to 535 mg/L. (Based on the Tables 3 to 15 given in Examples 3 to 15).

EXAMPLE 49

Dissolved 0.15 g glucose in 25 mL distilled water. Aliquots from the stock solution were taken and diluted with water to achieve different COD concentrations in the range of 320 to 535 mg/L. A 30 mL sample of Digested POME (ssp) was taken. Weighed 0.02 g $HgSO_4$ in separate 15 mL test tubes. 1.0 mL of glucose solution and sample were added to each test tube separately and mixed well. 0.5 mL of $K_2Cr_2O_7$ was added to each sample. 1.5 mL $H_2SO_4$ silver sulphate reagent was added slowly with continuous shaking. The color of the reaction mixture was noted down visually within 15 sec of incubation and also recorded spectrophotometrically at 585 and 635 nm against air. An approximate COD value of the sample was estimated from the color of standard reaction mixture prepared with glucose as reference material in the COD range of 200 to 100000 mg/L. OD 585 and OD 635 of the reaction mixture was read spectrophotometrically. OD 585 and 635 nm in the range of 0.130 to 0.175 and 0.120 to 0.160 respectively were considered and calculated with reference to glucose standard. (Glucose COD in the range of 320 to 535 mg/L corresponds to OD 585 and 635 nm in the range of 0.157 to 0.207 and 0.142 to 0.189, respectively).

COD of the sample was estimated to be 588.4 mg/L. (By Merck method and read on photometer).

Based on the color of the reaction mixture, COD of the sample was estimated to be around 400 mg/L. On the basis of the dilution method and the spectrophotometric reading at OD 585 and OD 635 of the sample, COD was estimated to be 535 and 458 mg/l respectively. A comparison with the COD value calculated through Merck method reveals the following relation i.e. Our COD value (at OD 585)×1.10 COD value (Merck Method) or our COD value (at OD 635)×1.30=COD value (Merck Method).

Hence for a preliminary estimate of COD value color of the standard reaction mixture based on a range of glucose concentrations can be used as a reference. For samples, with COD concentration of 300 to 500 mg/L, OD 585 or OD 635 can be recorded for obtaining more precise values.

Digested POME (ssp)

TABLE 49

Correlation between COD concentration, color of the reaction mixture and their OD at different wave lengths.

| COD (mg/L) 1 | Sample dilution (Times) 2 | Color of the reaction mixture 3 | OD 4 | Estimated COD (mg/L) 5 | Estimated final COD (mg/L) (Col. 2 × 5) 6 |
|---|---|---|---|---|---|
| Values at OD 585 nm | | | | | |
| Glucose: | | | | | |
| 320 | NA | C300 | 0.162 | NA | NA |
| 426 | NA | C400 | 0.189 | NA | NA |
| 535 | NA | C550 | 0.207 | NA | NA |
| Sample: Digested POME (ssp) | | | | | |
| | Nil | C400 | 0.168 | 535 | 535 |
| Values at OD 635 nm | | | | | |
| Glucose: | | | | | |
| 320 | NA | C300 | 0.146 | NA | NA |
| 426 | NA | C400 | 0.171 | NA | NA |
| 535 | NA | C550 | 0.187 | NA | NA |
| Sample: Digested POME (ssp) | | | | | |
| | Nil | C400 | 0.148 | 458 | 458 |

COD as deducible from Table 2 given in Example 2.
D: Dark.
T: Turbid.
*OD out of range.
NA: Not applicable.
Samples are diluted to get an OD 585 in the range of 0.130 to 0.175 and OD 635 in the range of 0.120 to 0.160, to obtain a COD value in the range of 320 to 535 mg/L. (Based on the Tables 3 to 15 given in Examples 3 to 15).

EXAMPLE 50

Dissolved 0.15 g glucose in 25 mL distilled water. Aliquots from the stock solution were taken and diluted with water to achieve different COD concentrations in the range of 320 to 535 mg/L. A 30 mL sample of Digested POME and Tea (as such) was taken. Weighed 0.02 g HgSO$_4$ in separate 15 mL test tubes. 1.0 mL of glucose solution and sample were added to each test tube separately and mixed well. 0.5 mL of K$_2$Cr$_2$O$_7$ was added to each sample. 1.5 mL H$_2$SO$_4$ silver sulphate reagent was added slowly with continuous shaking. The color of the reaction mixture was noted down visually within 15 sec of incubation and also recorded spectrophotometrically at 585 and 635 nm against air. An approximate COD value of the sample was estimated from the color of standard reaction mixture prepared with glucose as reference material in the COD range of 200 to 100000 mg/L. OD 585 and OD 635 of the reaction mixture was read spectrophotometrically. OD 585 and 635 nm in the range of 0.130 to 0.175 and 0.120 to 0.160 respectively were considered and calculated with reference to glucose standard. (Glucose COD in the range of 320 to 535 mg/L corresponds to OD 585 and 635 nm in the range of 0.157 to 0.207 and 0.142 to 0.189, respectively).

COD of the sample was estimated to be 59,593 mg/L. (By Merck method and read on photometer).

Based on the color of the reaction mixture, COD of the sample was estimated to be around 50000 mg/L. On the basis of the dilution method and the spectrophotometric reading at OD 585 and OD 635 of the sample, COD was estimated to be 41600 and 41900 mg/l respectively. A comparison with the COD value calculated through Merck method reveals the following relation i.e. Our COD value (at OD 585)×1.43=COD value (Merck Method) or our COD value (at OD 635)×1.42=COD value (Merck Method).

Hence for a preliminary estimate of COD value color of the standard reaction mixture based on a range of glucose concentrations can be used as a reference. For samples, with COD concentration of 300 to 500 mg/L, OD 585 or OD 635 can be recorded for obtaining more precise values.

Digested Pome+Tea (as such)

TABLE 50

Correlation between COD concentration, color of the reaction mixture and their OD at different wave lengths.

| COD (mg/L) 1 | Sample dilution (Times) 2 | Color of the reaction mixture 3 | OD 4 | Estimated COD (mg/L) 5 | Estimated final COD (mg/L) (Col. 2 × 5) 6 |
|---|---|---|---|---|---|
| Values at OD 585 nm | | | | | |
| Glucose: | | | | | |
| 320 | NA | C300 | 0.162 | NA | NA |
| 426 | NA | C400 | 0.187 | NA | NA |
| 535 | NA | C550 | 0.208 | NA | NA |
| Sample: Digested Pome + Tea (as such) | | | | | |
| | Nil | C10000 | — | >10,000 | >10,000 |
| | 10 | C5000 | 0.416 | ≅5000 | ≅50,000# |
| | 100 | C400 | 0.149 | 416 | 41600 |
| Values at OD 635 nm | | | | | |
| Glucose: | | | | | |
| 320 | NA | C300 | 0.141 | NA | NA |
| 426 | NA | C400 | 0.162 | NA | NA |
| 535 | NA | C500 | 0.192 | NA | NA |

TABLE 50-continued

Correlation between COD concentration, color of the reaction mixture and their OD at different wave lengths.

| COD (mg/L) 1 | Sample dilution (Times) 2 | Color of the reaction mixture 3 | OD 4 | Estimated COD (mg/L) 5 | Estimated final COD (mg/L) (Col. 2 × 5) 6 |
|---|---|---|---|---|---|
| Sample: Digested Pome + Tea (as such) | | | | | |
| Nil | | C10000 | — | >10,000 | >10,000 |
| | 10 | C5000 | 0.353 | ≈5000 | ≈50,000# |
| | 100 | C400 | 0.130 | 419 | 41900 |

COD as deducible from Table 2 given in Example 2.
D: Dark.
T: Turbid.
*OD out of range.
NA: Not applicable.
Samples are diluted to get an OD 585 in the range of 0.130 to 0.175 and OD 635 in the range of 0.120 to 0.160, to obtain a COD value in the range of 320 to 535 mg/L. (Based on the Tables 3 to 15 given in Examples 3 to 15).

EXAMPLE 51

Dissolved 0.15 g glucose in 25 mL distilled water. Aliquots from the stock solution were taken and diluted with water to achieve different COD concentrations in the range of 320 to 535 mg/L. A 30 mL sample of Digested POME and Tea (ssp) was taken. Weighed 0.02 g $HgSO_4$ in separate 15 mL test tubes. 1.0 mL of glucose solution and sample were added to each test tube separately and mixed well. 0.5 mL of $K_2Cr_2O_7$ was added to each sample. 1.5 mL $H_2SO_4$ silver sulphate reagent was added slowly with continuous shaking. The color of the reaction mixture was noted down visually within 15 sec of incubation and also recorded spectrophotometrically at 585 and 635 nm against air. An approximate COD value of the sample was estimated from the color of standard reaction mixture prepared with glucose as reference material in the COD range of 200 to 100000 mg/L. OD 585 and OD 635 of the reaction mixture was read spectrophotometrically. OD 585 and 635 nm in the range of 0.130 to 0.175 and 0.120 to 0.160 respectively were considered and calculated with reference to glucose standard. (Glucose COD in the range of 320 to 535 mg/L corresponds to OD 585 and 635 nm in the range of 0.157 to 0.207 and 0.142 to 0.189, respectively).

COD of the sample was estimated to be 39,928 mg/L. (By Merck method and read on photometer).

Based on the color of the reaction mixture, COD of the sample was estimated to be around 20000 mg/L. On the basis of the dilution method and the spectrophotometric reading at OD 585 and OD 635 of the sample, COD was estimated to be 38556 and 36985 mg/l respectively. A comparison with the COD value calculated through Merck method reveals the following relation i.e. Our COD value (at OD 585)×1.43=COD value (Merck Method) or our COD value (at OD 635)×1.42=COD value (Merck Method).

Hence for a preliminary estimate of COD value color of the standard reaction mixture based on a range of glucose concentrations can be used as a reference. For samples, with COD concentration of 300 to 500 mg/L, OD 585 or OD 635 can be recorded for obtaining more precise values.

Digested Pome+Tea (ssp)

TABLE 51

Correlation between COD concentration, color of the reaction mixture and their OD at different wave lengths.

| COD (mg/L) 1 | Sample dilution (Times) 2 | Color of the reaction mixture 3 | OD 4 | Estimated COD (mg/L) 5 | Estimated final COD (mg/L) (Col. 2 × 5) 6 |
|---|---|---|---|---|---|
| Values at OD 585 nm | | | | | |
| Glucose: | | | | | |
| 320 | NA | C300 | 0.162 | NA | NA |
| 426 | NA | C400 | 0.187 | NA | NA |
| 535 | NA | C550 | 0.208 | NA | NA |
| Sample: Digested Pome + Tea (ssp) | | | | | |
| Nil | | C10000 | — | >10,000 | ≈10,000 |
| | 10 | C2000 | 0.386 | ≈2000 | ≈20,000# |
| | 100 | C200 | 0.107 | 200 | 20,000 |
| | 71.4 | C500 | 0.175 | 540 | 38556 |
| Values at OD 635 nm | | | | | |
| Glucose: | | | | | |
| 320 | NA | C300 | 0.141 | NA | NA |
| 426 | NA | C400 | 0.162 | NA | NA |
| 535 | NA | C550 | 0.192 | NA | NA |
| Sample: Digested Pome + Tea (ssp) | | | | | |
| Nil | | C10000 | — | >10,000 | ≈10,000 |
| | 10 | C2000 | 0.336 | ≈2000 | ≈20,000# |
| | 100 | C200 | 0.092 | 200 | 20,000 |
| | 71.4 | C500 | 0.155 | 518 | 36985 |

COD as deducible from Table 2 given in Example 2.
D: Dark.
T: Turbid.
*OD out of range.
NA: Not applicable.
Samples are diluted to get an OD 585 in the range of 0.130 to 0.175 and OD 635 in the range of 0.120 to 0.160, to obtain a COD value in the range of 320 to 535 mg/L. (Based on the Tables 3 to 15 given in Examples 3 to 15).

EXAMPLE 52

Dissolved 0.15 g glucose in 25 mL distilled water. Aliquots from the stock solution were taken and diluted with water to achieve different COD concentrations in the range of 320 to 535 mg/L. A 30 mL sample of Digested POME and Apple pomace (as such) was taken. Weighed 0.02 g $HgSO_4$ in separate 15 mL test tubes. 1.0 mL of glucose solution and sample were added to each test tube separately and mixed well. 0.5 mL of $K_2Cr_2O_7$ was added to each sample. 1.5 mL $H_2SO_4$ silver sulphate reagent was added slowly with continuous shaking. The color of the reaction mixture was noted down visually within 15 sec of incubation and also recorded spectrophotometrically at 585 and 635 nm against air. An approximate COD value of the sample was estimated from the color of standard reaction mixture prepared with glucose as reference material in the COD range of 200 to 100000 mg/L. OD 585 and OD 635 of the reaction mixture was read spectrophotometrically. OD 585 and 635 nm in the range of 0.130 to 0.175 and 0.120 to 0.160 respectively were considered and calculated with reference to glucose standard. (Glucose COD in the range of 320 to 535 mg/L corresponds to OD 585 and 635 nm in the range of 0.157 to 0.207 and 0.142 to 0.189, respectively).

COD of the sample was estimated to be 24,932 mg/L. (By Merck method and read on photometer).

Based on the color of the reaction mixture, COD of the sample was estimated to be around 15000 mg/L. On the basis of the dilution method and the spectrophotometric reading at OD 585 and OD 635 of the sample, COD was estimated to be 15800 and 6955 mg/l respectively. A comparison with the COD value calculated through Merck method reveals the following relation i.e. Our COD value (at OD 585)×1.58=COD value (Merck Method) or our COD value (at OD 635)×1.47=COD value (Merck Method).

Hence for a preliminary estimate of COD value color of the standard reaction mixture based on a range of glucose concentrations can be used as a reference. For samples, with COD concentration of 300 to 500 mg/L, OD 585 or OD 635 can be recorded for obtaining more precise values.

Digested Pome+Apple Pomace (as such)

TABLE 52

Correlation between COD concentration, color of the reaction mixture and their OD at different wave lengths.

| COD (mg/L) 1 | Sample dilution (Times) 2 | Color of the reaction mixture 3 | OD 4 | Estimated COD (mg/L) 5 | Estimated final COD (mg/L) (Col. 2 × 5) 6 |
|---|---|---|---|---|---|
| Values at OD 585 nm | | | | | |
| Glucose: | | | | | |
| 320 | NA | C300 | 0.158 | NA | NA |
| 426 | NA | C400 | 0.186 | NA | NA |
| 535 | NA | C550 | 0.205 | NA | NA |
| Sample: Digested Pome + Apple Pomace (as such) | | | | | |
| | Nil | C10000 | — | >10,000 | >10,000 |
| | 10 | C1500 | 0.336 | ≈1500 | ≈15,000# |
| | 50 | C400 | 0.130 | 316 | 15800 |
| Values at OD 635 nm | | | | | |
| Glucose: | | | | | |
| 320 | NA | C300 | 0.137 | NA | NA |
| 426 | NA | C400 | 0.159 | NA | NA |
| 535 | NA | C550 | 0.191 | NA | NA |
| Sample: Digested Pome + Apple Pomace (as such) | | | | | |
| | Nil | C10000 | — | >10,000 | >10,000 |
| | 10 | C1500 | 0.305 | ≈1500 | ≈15,000# |
| | 50 | C400 | 0.121 | 339 | 16955 |

COD as deducible from Table 2 given in Example 2.
D: Dark.
T: Turbid.
*OD out of range.
NA: Not applicable.
Samples are diluted to get an OD 585 in the range of 0.130 to 0.175 and OD 635 in the range of 0.120 to 0.160, to obtain a COD value in the range of 320 to 535 mg/L. (Based on the Tables 3 to 15 given in Examples 3 to 15).

EXAMPLE 53

Dissolved 0.15 g glucose in 25 mL distilled water. Aliquots from the stock solution were taken and diluted with water to achieve different COD concentrations in the range of 320 to 535 mg/L. A 30 mL sample of Digested Palm oil mill effluent (POME) and Apple pomace (ssp) was taken. Weighed 0.02 g $HgSO_4$ in separate 15 mL test tubes. 1.0 mL of glucose solution and sample were added to each test tube separately and mixed well. 0.5 mL of $K_2Cr_2O_7$ was added to each sample. 1.5 mL $H_2SO_4$ silver sulphate reagent was added slowly with continuous shaking. The color of the reaction mixture was noted down visually within 15 sec of incubation and also recorded spectrophotometrically at 585 and 635 nm against air. An approximate COD value of the sample was estimated from the color of standard reaction mixture prepared with glucose as reference material in the COD range of 200 to 100000 mg/L. OD 585 and OD 635 of the reaction mixture was read spectrophotometrically. OD 585 and 635 nm in the range of 0.130 to 0.175 and 0.120 to 0.160 respectively were considered and calculated with reference to glucose standard. (Glucose COD in the range of 320 to 535 mg/L corresponds to OD 585 and 635 nm in the range of 0.157 to 0.207 and 0.142 to 0.189, respectively).

COD of the sample was estimated to be 21,666 mg/L. (By Merck method and read on photometer).

Based on the color of the reaction mixture, COD of the sample was estimated to be around 16000 mg/L. On the basis of the dilution method and the spectrophotometric reading at OD 585 and OD 635 of the sample, COD was estimated to be 32600 and 41310 mg/l respectively. A comparison with the COD value calculated through Merck method reveals the following relation i.e. Our COD value (at OD 585)×0.66=COD value (Merck Method) or our COD value (at OD 635)×0.52=COD value (Merck Method).

Hence for a preliminary estimate of COD value color of the standard reaction mixture based on a range of glucose concentrations can be used as a reference. For samples, with COD concentration of 300 to 500 mg/L, OD 585 or OD 635 can be recorded for obtaining more precise values.

Digested Pome+Apple Pomace (ssp)

TABLE 53

Correlation between COD concentration, color of the reaction mixture and their OD at different wave lengths.

| COD (mg/L) 1 | Sample dilution (Times) 2 | Color of the reaction mixture 3 | OD 4 | Estimated COD (mg/L) 5 | Estimated final COD (mg/L) (Col. 2 × 5) 6 |
|---|---|---|---|---|---|
| Values at OD 585 nm | | | | | |
| Glucose: | | | | | |
| 320 | NA | C300 | 0.158 | NA | NA |
| 426 | NA | C400 | 0.186 | NA | NA |
| 535 | NA | C550 | 0.205 | NA | NA |
| Sample: Digested Pome + Apple Pomace (ssp) | | | | | |
| | Nil | C10000 | — | >10,000 | >10,000 |
| | 10 | C1600 | 0.357 | ≈1600 | ≈16,000# |
| | 100 | C300 | 0.134 | 326 | 32600 |
| Values at OD 635 nm | | | | | |
| Glucose: | | | | | |
| 320 | NA | C300 | 0.137 | NA | NA |
| 426 | NA | C400 | 0.159 | NA | NA |
| 535 | NA | C550 | 0.191 | NA | NA |
| Sample: Digested Pome + Apple Pomace (ssp) | | | | | |
| | Nil | C10000 | — | >10,000 | >10,000 |
| | 10 | C1600 | 0.357 | ≈1600 | ≈16,000# |
| | 100 | C300 | 0.134 | 413 | 41300 |

COD as deducible from Table 2 given in Example 2.
D: Dark.
T: Turbid.
*OD out of range.
NA: Not applicable.
Samples are diluted to get an OD 585 in the range of 0.130 to 0.175 and OD 635 in the range of 0.120 to 0.160, to obtain a COD value in the range of 320 to 535 mg/L. (Based on the Tables 3 to 15 given in Examples 3 to 15).

EXAMPLE 54

Dissolved 0.15 g glucose in 25 mL distilled water. Aliquots from the stock solution were taken and diluted with water to achieve different COD concentrations in the range of 320 to 535 mg/L. A 30 mL sample of Digested POME, Apple pomace and Tea (as such) was taken. Weighed 0.02 g $HgSO_4$ in separate 15 mL test tubes. 1.0 mL of glucose solution and sample were added to each test tube separately and mixed well. 0.5 mL of $K_2Cr_2O_7$ was added to each sample. 1.5 mL $H_2SO_4$ silver sulphate reagent was added slowly with continuous shaking. The color of the reaction mixture was noted down visually within 15 sec of incubation and also recorded spectrophotometrically at 585 and 635 nm against air. An approximate COD value of the sample was estimated from the color of standard reaction mixture prepared with glucose as reference material in the COD range of 200 to 100000 mg/L. OD 585 and OD 635 of the reaction mixture was read spectrophotometrically. OD 585 and 635 nm in the range of 0.130 to 0.175 and 0.120 to 0.160 respectively were considered and calculated with reference to glucose standard. (Glucose COD in the range of 320 to 535 mg/L corresponds to OD 585 and 635 nm in the range of 0.157 to 0.207 and 0.142 to 0.189, respectively).

COD of the sample was estimated to be 34,569 mg/L. (By Merck method and read on photometer).

Based on the color of the reaction mixture, COD of the sample was estimated to be around 45000 mg/L. On the basis of the dilution method and the spectrophotometric reading at OD 585 and OD 635 of the sample, COD was estimated to be 35774 and 36552 mg/l respectively. A comparison with the COD value calculated through Merck method reveals the following relation i.e. Our COD value (at OD 585)×0.97=COD value (Merck Method) or our COD value (at OD 635)×0.94=COD value (Merck Method).

Hence for a preliminary estimate of COD value color of the standard reaction mixture based on a range of glucose concentrations can be used as a reference. For samples, with COD concentration of 300 to 500 mg/L, OD 585 or OD 635 can be recorded for obtaining more precise values.

Digested Pome+Apple Pomace+Tea (as such)

TABLE 54

Correlation between COD concentration, color of the reaction mixture and their OD at different wave lengths.

| COD (mg/L) | Sample dilution (Times) | Color of the reaction mixture | OD | Estimated COD (mg/L) | Estimated final COD (mg/L) (Col. 2 × 5) |
|---|---|---|---|---|---|
| 1 | 2 | 3 | 4 | 5 | 6 |
| Values at OD 585 nm | | | | | |
| Glucose: | | | | | |
| 320 | NA | C300 | 0.160 | NA | NA |
| 426 | NA | C400 | 0.185 | NA | NA |
| 535 | NA | C550 | 0.211 | NA | NA |
| Sample: Digested Pome + Apple Pomace + Tea (as such) | | | | | |
| | Nil | C10000 | — | >10,000 | >10,000 |
| | 10 | C4500 | 0.428 | ≅4500 | ≅45,000# |
| | 100 | C450 | 0.189 | ≅450 | ≅45,000# |
| | 111.1 | C300 | 0.134 | 322 | 35774 |

TABLE 54-continued

Correlation between COD concentration, color of the reaction mixture and their OD at different wave lengths.

| COD (mg/L) | Sample dilution (Times) | Color of the reaction mixture | OD | Estimated COD (mg/L) | Estimated final COD (mg/L) (Col. 2 × 5) |
|---|---|---|---|---|---|
| 1 | 2 | 3 | 4 | 5 | 6 |
| Values at OD 635 nm | | | | | |
| Glucose: | | | | | |
| 320 | NA | C300 | 0.141 | NA | NA |
| 426 | NA | C400 | 0.162 | NA | NA |
| 535 | NA | C550 | 0.197 | NA | NA |
| Sample: Digested Pome + Apple Pomace + Tea (as such) | | | | | |
| | Nil | C10000 | — | >10,000 | >10,000 |
| | 10 | C4500 | 0.375 | ≅4500 | ≅45,000# |
| | 100 | C450 | 0.173 | ≅450 | ≅45,000# |
| | 111.1 | C300 | 0.121 | 329 | 36552 |

COD as deducible from Table 2 given in Example 2.
D: Dark.
T: Turbid.
*OD out of range.
NA: Not applicable.
Samples are diluted to get an OD 585 in the range of 0.130 to 0.175 and OD 635 in the range of 0.120 to 0.160, to obtain a COD value in the range of 320 to 535 mg/L. (Based on the Tables 3 to 15 given in Examples 3 to 15).

EXAMPLE 55

Dissolved 0.15 g glucose in 25 mL distilled water. Aliquots from the stock solution were taken and diluted with water to achieve different COD concentrations in the range of 320 to 535 mg/L. A 30 mL sample of Digested POME, Apple pomace and Tea (ssp) was taken. Weighed 0.02 g $HgSO_4$ in separate 15 mL test tubes. 1.0 mL of glucose solution and sample were added to each test tube separately and mixed well. 0.5 mL of $K_2Cr_2O_7$ was added to each sample. 1.5 mL $H_2SO_4$ silver sulphate reagent was added slowly with continuous shaking. The color of the reaction mixture was noted down visually within 15 sec of incubation and also recorded spectrophotometrically at 585 and 635 nm against air. An approximate COD value of the sample was estimated from the color of standard reaction mixture prepared with glucose as reference material in the COD range of 200 to 100000 mg/L. OD 585 and OD 635 of the reaction mixture was read spectrophotometrically. OD 585 and 635 nm in the range of 0.130 to 0.175 and 0.120 to 0.160 respectively were considered and calculated with reference to glucose standard. (Glucose COD in the range of 320 to 535 mg/L corresponds to OD 585 and 635 nm in the range of 0.157 to 0.207 and 0.142 to 0.189, respectively).

COD of the sample was estimated to be 34,040 mg/L. (By Merck method and read on photometer).

Based on the color of the reaction mixture, COD of the sample was estimated to be around 40000 mg/L. On the basis of the dilution method and the spectrophotometric reading at OD 585 and OD 635 of the sample, COD was estimated to be 46800 and 48100 mg/l. A comparison with the COD value calculated through Merck method reveals the following relation i.e. Our COD value (at OD 585)×0.73= COD value (Merck Method) or our COD value (at OD 635)×0.71=COD value (Merck Method).

Hence for a preliminary estimate of COD value color of the standard reaction mixture based on a range of glucose concentrations can be used as a reference. For samples, with COD concentration of 300 to 500 mg/L, OD 585 or OD 635 can be recorded for obtaining more precise values.

Digested Pome+Apple Pomace+Tea (ssp)

TABLE 55

Correlation between COD concentration, color of the reaction mixture and their OD at different wave lengths.

| COD (mg/L) 1 | Sample dilution (Times) 2 | Color of the reaction mixture 3 | OD 4 | Estimated COD (mg/L) 5 | Estimated final COD (mg/L) (Col. 2 × 5) 6 |
|---|---|---|---|---|---|
| Values at OD 585 nm | | | | | |
| Glucose: | | | | | |
| 320 | NA | C300 | 0.160 | NA | NA |
| 426 | NA | C400 | 0.185 | NA | NA |
| 535 | NA | C550 | 0.211 | NA | NA |
| Sample: Digested Pome + Apple Pomace + Tea (ssp) | | | | | |
| | Nil | C10000 | — | >10,000 | >10,000 |
| | 10 | C4000 | 0.373 | ≅4000 | ≅40,000# |
| | 100 | C400 | 0.166 | 468 | 46800 |
| Values at OD 635 nm | | | | | |
| Glucose: | | | | | |
| 320 | NA | C300 | 0.141 | NA | NA |
| 426 | NA | C400 | 0.162 | NA | NA |
| 535 | NA | C550 | 0.197 | NA | NA |
| Sample: Digested Pome + Apple Pomace + Tea (ssp) | | | | | |
| | Nil | C10000 | — | >10,000 | >10,000 |
| | 10 | C4000 | 0.322 | ≅4000 | ≅40,000# |
| | 100 | C400 | 0.149 | 481 | 48100 |

COD as deducible from Table 2 given in Example 2.
D: Dark.
T: Turbid.
*OD out of range.
NA: Not applicable.
Samples are diluted to get an OD 585 in the range of 0.130 to 0.175 and OD 635 in the range of 0.120 to 0.160, to obtain a COD value in the range of 320 to 535 mg/L. (Based on the Tables 3 to 15 given in Examples 3 to 15).

EXAMPLE 56

Dissolved 0.15 g glucose in 25 mL distilled water. Aliquots from the stock solution were taken and diluted with water to achieve different COD concentrations in the range of 320 to 535 mg/L. A 30 mL sample of Tea and Apple pomace (ssp) was taken. Weighed 0.02 g $HgSO_4$ in separate 15 mL test tubes. 1.0 mL of glucose solution and sample were added to each test tube separately and mixed well. 0.5 mL of $K_2Cr_2O_7$ was added to each sample. 1.5 mL $H_2SO_4$ silver sulphate reagent was added slowly with continuous shaking. The color of the reaction mixture was noted down visually within 15 sec of incubation and also recorded spectrophotometrically at 585 and 635 nm against air. An approximate COD value of the sample was estimated from the color of standard reaction mixture prepared with glucose as reference material in the COD range of 200 to 100000 mg/L. OD 585 and OD 635 of the reaction mixture was read spectrophotometrically. OD 585 and 635 nm in the range of 0.130 to 0.175 and 0.120 to 0.160 respectively were considered and calculated with reference to glucose standard. (Glucose COD in the range of 320 to 535 mg/L corresponds to OD 585 and 635 nm in the range of 0.157 to 0.207 and 0.142 to 0.189, respectively).

COD of the sample was estimated to be 75,716 mg/L. (By Merck method and read on photometer).

Based on the color of the reaction mixture, COD of the sample was estimated to be around 78540 mg/L. On the basis of the dilution method and the spectrophotometric reading at OD 585 and OD 635 of the sample, COD was estimated to be 86400 and 83600 mg/l respectively. A comparison with the COD value calculated through Merck method reveals the following relation i.e. Our COD value (at OD 585)×0.88=COD value (Merck Method) or our COD value (at OD 635)×0.91=COD value (Merck Method).

Hence for a preliminary estimate of COD value color of the standard reaction mixture based on a range of glucose concentrations can be used as a reference. For samples, with COD concentration of 300 to 500 mg/L, OD 585 or OD 635 can be recorded for obtaining more precise values.

Tea+Apple Pomace (ssp)

TABLE 56

Correlation between COD concentration, color of the reaction mixture and their OD at different wave lengths.

| COD (mg/L) 1 | Sample dilution (Times) 2 | Color of the reaction mixture 3 | OD 4 | Estimated COD (mg/L) 5 | Estimated final COD (mg/L) (Col. 2 × 5) 6 |
|---|---|---|---|---|---|
| Values at OD 585 nm | | | | | |
| Glucose: | | | | | |
| 320 | NA | C300 | 0.159 | NA | NA |
| 426 | NA | C400 | 0.186 | NA | NA |
| 535 | NA | C550 | 0.205 | NA | NA |
| Sample: Tea + Apple Pomace (ssp) | | | | | |
| | Nil | C10000 | — | >10,000 | ≅>10,000 |
| | 10 | C5500 | 0.372 | ≅5500 | ≅55,000 |
| | 100 | C1600 | 0.225 | ≅1600 | ≅1,60,000 |
| | 142.8 | C550 | 0.175 | ≅550 | ≅78,540# |
| | 200 | C400 | 0.157 | 432 | 86400 |
| Values at OD 635 nm | | | | | |
| Glucose: | | | | | |
| 320 | NA | C300 | 0.143 | NA | NA |
| 426 | NA | C400 | 0.168 | NA | NA |
| 535 | NA | C550 | 0.186 | NA | NA |
| Sample: Tea + Apple Pomace (ssp) | | | | | |
| | Nil | C10000 | — | >10,000 | ≅>10,000 |
| | 10 | C5500 | 0.295 | ≅5500 | ≅55,000 |
| | 100 | C1600 | 0.201 | ≅1600 | ≅1,60,000 |
| | 142.8 | C550 | 0.155 | ≅550 | ≅78,540# |
| | 200 | C400 | 0.136 | 418 | 83600 |

COD as deducible from Table 2 given in Example 2.
D: Dark.
T: Turbid.
*OD out of range.
NA: Not applicable.
Samples are diluted to get an OD 585 in the range of 0.130 to 0.175 and OD 635 in the range of 0.120 to 0.160, to obtain a COD value in the range of 320 to 535 mg/L. (Based on the Tables 3 to 15 given in Examples 3 to 15).

EXAMPLE 57

Dissolved 0.15 g glucose in 25 mL distilled water. Aliquots from the stock solution were taken and diluted with water to achieve different COD concentrations in the range of 320 to 535 mg/L. A 30 mL sample of Damaged wheat grain (ssp) was taken. Weighed 0.02 g $HgSO_4$ in separate 15 mL test tubes. 1.0 mL of glucose solution and sample were added to each test tube separately and mixed well. 0.5 mL of $K_2Cr_2O_7$ was added to each sample. 1.5 mL $H_2SO_4$ silver sulphate reagent was added slowly with continuous shaking. The color of the reaction mixture was noted down visually within 15 sec of incubation and also recorded spectrophotometrically at 585 and 635 nm against air. An approximate COD value of the sample was estimated from the color of standard reaction mixture prepared with glucose as reference material in the COD range of 200 to 100000 mg/L. OD 585 and OD 635 of the reaction mixture was read spectrophotometrically. OD 585 and 635 nm in the range of 0.130 to 0.175 and 0.120 to 0.160 respectively were considered and calculated with reference to glucose standard. (Glucose COD in the range of 320 to 535 mg/L corresponds to OD 585 and 635 nm in the range of 0.157 to 0.207 and 0.142 to 0.189, respectively).

COD of the sample was estimated to be 11,707 mg/L. (By Merck method and read on photometer).

Based on the color of the reaction mixture, COD of the sample was estimated to be around 1400 mg/L. On the basis of the dilution method and the spectrophotometric reading at OD 585 and OD 635 of the sample, COD was estimated to be 5160 and 5040 mg/l respectively. A comparison with the COD value calculated through Merck method reveals the following relation i.e. Our COD value (at OD 585)×2.26= COD value (Merck Method) or our COD value (at OD 635)×2.31=COD value (Merck Method).

Hence for a preliminary estimate of COD value color of the standard reaction mixture based on a range of glucose concentrations can be used as a reference. For samples, with COD concentration of 300 to 500 mg/L, OD 585 or OD 635 can be recorded for obtaining more precise values.

DWS (S3) (ssp)

TABLE 57

Correlation between COD concentration, color of the reaction mixture and their OD at different wave lengths.

| COD (mg/L) 1 | Sample dilution (Times) 2 | Color of the reaction mixture 3 | OD 4 | Estimated COD (mg/L) 5 | Estimated final COD (mg/L) (Col. 2 × 5) 6 |
|---|---|---|---|---|---|
| Values at OD 585 nm | | | | | |
| Glucose: | | | | | |
| 320 | NA | C300 | 0.159 | NA | NA |
| 426 | NA | C400 | 0.186 | NA | NA |
| 535 | NA | C550 | 0.205 | NA | NA |
| Sample: DWS (S3) (ssp) | | | | | |
|  | Nil | C1400 | 0.636 | ≅1400 | ≅1400# |
|  | 10 | C400 | 0.165 | 516 | 5160 |
| Values at OD 635 nm | | | | | |
| Glucose: | | | | | |
| 320 | NA | C300 | 0.143 | NA | NA |
| 426 | NA | C400 | 0.168 | NA | NA |
| 535 | NA | C550 | 0.186 | NA | NA |

TABLE 57-continued

Correlation between COD concentration, color of the reaction mixture and their OD at different wave lengths.

| COD (mg/L) 1 | Sample dilution (Times) 2 | Color of the reaction mixture 3 | OD 4 | Estimated COD (mg/L) 5 | Estimated final COD (mg/L) (Col. 2 × 5) 6 |
|---|---|---|---|---|---|
| Sample: DWS (S3) (ssp) | | | | | |
|  | Nil | C1400 | 0.494 | ≅1400 | ≅1400# |
|  | 10 | C400 | 0.147 | 504 | 5040 |

COD as deducible from Table 2 given in Example 2.
D: Dark.
T: Turbid.
*OD out of range.
NA: Not applicable.
Samples are diluted to get an OD 585 in the range of 0.130 to 0.175 and OD 635 in the range of 0.120 to 0.160, to obtain a COD value in the range of 320 to 535 mg/L. (Based on the Tables 3 to 15 given in Examples 3 to 15).

EXAMPLE 58

Dissolved 0.15 g glucose in 25 mL distilled water. Aliquots from the stock solution were taken and diluted with water to achieve different COD concentrations in the range of 320 to 535 mg/L. A 30 mL sample of Tea, Apple pomace and Damaged wheat grain (ssp) was taken. Weighed 0.02 g $HgSO_4$ in separate 15 mL test tubes. 1.0 mL of glucose solution and sample were added to each test tube separately and mixed well. 0.5 mL of $K_2Cr_2O_7$ was added to each sample. 1.5 mL $H_2SO_4$ silver sulphate reagent was added slowly with continuous shaking. The color of the reaction mixture was noted down visually within 15 sec of incubation and also recorded spectrophotometrically at 585 and 635 nm against air. An approximate COD value of the sample was estimated from the color of standard reaction mixture prepared with glucose as reference material in the COD range of 200 to 100000 mg/L. OD 585 and OD 635 of the reaction mixture was read spectrophotometrically. OD 585 and 635 nm in the range of 0.130 to 0.175 and 0.120 to 0.160 respectively were considered and calculated with reference to glucose standard. (Glucose COD in the range of 320 to 535 mg/L corresponds to OD 585 and 635 nm in the range of 0.157 to 0.207 and 0.142 to 0.189, respectively).

COD of the sample was estimated to be 22,689.5 mg/L. (By Merck method and read on photometer).

Based on the color of the reaction mixture, COD of the sample was estimated to be around 20000 mg/L. On the basis of the dilution method and the spectrophotometric reading at OD 585 and OD 635 of the sample, COD was estimated to be 22450 and 16950 mg/l respectively. A comparison with the COD value calculated through Merck method reveals the following relation i.e. Our COD value (at OD 585)×2.26=COD value (Merck Method) or our COD value (at OD 635)×2.31=COD value (Merck Method).

Hence for a preliminary estimate of COD value color of the standard reaction mixture based on a range of glucose concentrations can be used as a reference. For samples, with COD concentration of 300 to 500 mg/L, OD 585 or OD 635 can be recorded for obtaining more precise values.

Tea+Apple Pomace+DWS (S3) (ssp)

TABLE 58

Correlation between COD concentration, color of the reaction mixture and their OD at different wave lengths.

| COD (mg/L) 1 | Sample dilution (Times) 2 | Color of the reaction mixture 3 | OD 4 | Estimated COD (mg/L) 5 | Estimated final COD (mg/L) (Col. 2 × 5) 6 |
|---|---|---|---|---|---|
| Values at OD 585 nm | | | | | |
| Glucose: | | | | | |
| 320 | NA | C300 | 0.161 | NA | NA |
| 426 | NA | C400 | 0.185 | NA | NA |
| 535 | NA | C550 | 0.209 | NA | NA |
| Sample: Tea + Apple Pomace + DWS (S3) (ssp) | | | | | |
| | Nil | C10000 | — | >10,000 | >10,000 |
| | 10 | C4000 | 0.356 | ≈4000 | ≈40,000 |
| | 66.7 | C300 | 0.127 | ≈300 | ≈20,000# |
| | 50 | C400 | 0.162 | 449 | 22450 |
| Values at OD 635 nm | | | | | |
| Glucose: | | | | | |
| 320 | NA | C300 | 0.142 | NA | NA |
| 426 | NA | C400 | 0.163 | NA | NA |
| 535 | NA | C550 | 0.198 | NA | NA |
| Sample: Tea + Apple Pomace + DWS (S3) (ssp) | | | | | |
| | Nil | C10000 | — | >10,000 | >10,000 |
| | 10 | C4000 | 0.319 | ≈4000 | ≈40,000 |
| | 66.7 | C300 | 0.113 | ≈300 | ≈20,000# |
| | 50 | C400 | 0.142 | 339 | 16950 |

COD as deducible from Table 2 given in Example 2.
D: Dark.
T: Turbid.
*OD out of range.
NA: Not applicable.
Samples are diluted to get an OD 585 in the range of 0.130 to 0.175 and OD 635 in the range of 0.120 to 0.160, to obtain a COD value in the range of 320 to 535 mg/L. (Based on the Tables 3 to 15 given in Examples 3 to 15).

EXAMPLE 59

Dissolved 0.15 g glucose in 25 mL distilled water. Aliquots from the stock solution were taken and diluted with water to achieve different COD concentrations in the range of 320 to 535 mg/L. A 30 mL sample of Tea, Apple pomace, Damaged wheat grain and Peptone (ssp) was taken. Weighed 0.02 g $HgSO_4$ in separate 15 mL test tubes. 1.0 mL of glucose solution and sample were added to each test tube separately and mixed well. 0.5 mL of $K_2Cr_2O_7$ was added to each sample. 1.5 mL $H_2SO_4$ silver sulphate reagent was added slowly with continuous shaking. The color of the reaction mixture was noted down visually within 15 sec of incubation and also recorded spectrophotometrically at 585 and 635 nm against air. An approximate COD value of the sample was estimated from the color of standard reaction mixture prepared with glucose as reference material in the COD range of 200 to 100000 mg/L. OD 585 and OD 635 of the reaction mixture was read spectrophotometrically. OD 585 and 635 nm in the range of 0.130 to 0.175 and 0.120 to 0.160 respectively were considered and calculated with reference to glucose standard. (Glucose COD in the range of 320 to 535 mg/L corresponds to OD 585 and 635 nm in the range of 0.157 to 0.207 and 0.142 to 0.189, respectively).

COD of the sample was estimated to be 36,176 mg/L. (By Merck method and read on photometer).

Based on the color of the reaction mixture, COD of the sample was estimated to be around 20000 mg/L. On the basis of the dilution method and the spectrophotometric reading at OD 585 and OD 635 of the sample, COD was estimated to be 20900 and 21050 mg/l respectively. A comparison with the COD value calculated through Merck method reveals the following relation i.e. Our COD value (at OD 585)×1.73=COD value (Merck Method) or our COD value (at OD 635)×1.72=COD value (Merck Method).

Hence for a preliminary estimate of COD value color of the standard reaction mixture based on a range of glucose concentrations can be used as a reference. For samples, with COD concentration of 300 to 500 mg/L, OD 585 or OD 635 can be recorded for obtaining more precise values.

Tea+Apple Pomace+DWS (S3)+Peptone (ssp)

TABLE 59

Correlation between COD concentration, color of the reaction mixture and their OD at different wave lengths.

| COD (mg/L) 1 | Sample dilution (Times) 2 | Color of the reaction mixture 3 | OD 4 | Estimated COD (mg/L) 5 | Estimated final COD (mg/L) (Col. 2 × 5) 6 |
|---|---|---|---|---|---|
| Values at OD 585 nm | | | | | |
| Glucose: | | | | | |
| 320 | NA | C300 | 0.161 | NA | NA |
| 426 | NA | C400 | 0.185 | NA | NA |
| 535 | NA | C550 | 0.209 | NA | NA |
| Sample: Tea + Apple Pomace + DWS (S3) + Peptone (ssp) | | | | | |
| | Nil | C10000 | — | >10,000 | >10,000 |
| | 10 | C2000 | 0.348 | ≈2000 | ≈20,000# |
| | 50 | C300 | 0.151 | 418 | 20900 |
| Values at OD 635 nm | | | | | |
| Glucose: | | | | | |
| 320 | NA | C300 | 0.142 | NA | NA |
| 426 | NA | C400 | 0.163 | NA | NA |
| 535 | NA | C550 | 0.198 | NA | NA |
| Sample: Tea + Apple Pomace + DWS (S3) + Peptone (ssp) | | | | | |
| | Nil | C10000 | — | >10,000 | >10,000 |
| | 10 | C20000 | 0.315 | ≈2000 | ≈20,000# |
| | 50 | C300 | 0.134 | 421 | 21050 |

COD as deducible from Table 2 given in Example 2.
D: Dark.
T: Turbid.
*OD out of range.
NA: Not applicable.
Samples are diluted to get an OD 585 in the range of 0.130 to 0.175 and OD 635 in the range of 0.120 to 0.160, to obtain a COD value in the range of 320 to 535 mg/L. (Based on the Tables 3 to 15 given in Examples 3 to 15).

EXAMPLE 60

Dissolved 0.15 g glucose in 25 mL distilled water. Aliquots from the stock solution were taken and diluted with water to achieve different COD concentrations in the range of 320 to 535 mg/L. A 30 mL sample of Tea, Apple Pomace and Dabu (ssp) was taken. Weighed 0.02 g $HgSO_4$ in separate 15 mL test tubes. 1.0 mL of glucose solution and sample were added to each test tube separately and mixed well. 0.5 mL of $K_2Cr_2O_7$ was added to each sample. 1.5 mL $H_2SO_4$ silver sulphate reagent was added slowly with continuous shaking. The color of the reaction mixture was noted down visually within 15 sec of incubation and also recorded spectrophotometrically at 585 and 635 nm against air. An approximate COD value of the sample was estimated from the color of standard reaction mixture prepared with glucose as reference material in the COD range of 200 to 100000 mg/L. OD 585 and OD 635 of the reaction mixture was read spectrophotometrically. OD 585 and 635 nm in the range of 0.130 to 0.175 and 0.120 to 0.160 respectively were considered and calculated with reference to glucose standard. (Glucose COD in the range of 320 to 535 mg/L corresponds to OD 585 and 635 nm in the range of 0.157 to 0.207 and 0.142 to 0.189, respectively).

COD of the sample was estimated to be 77,786 mg/L. (By Merck method and read on photometer).

Based on the color of the reaction mixture, COD of the sample was estimated to be around 55000 mg/L. On the basis of the dilution method and the spectrophotometric reading at OD 585 and OD 635 of the sample, COD was estimated to be 71714 and 74348 mg/l respectively. A comparison with the COD value calculated through Merck method reveals the following relation i.e. Our COD value (at OD 585)×1.08=COD value (Merck Method) or our COD value (at OD 635)×1.05=COD value (Merck Method).

Hence for a preliminary estimate of COD value color of the standard reaction mixture based on a range of glucose concentrations can be used as a reference. For samples, with COD concentration of 300 to 500 mg/L, OD 585 or OD 635 can be recorded for obtaining more precise values.

Tea+Apple Pomace+Dabu (ssp)

TABLE 60

Correlation between COD concentration, color of the reaction mixture and their OD at different wave lengths.

| COD (mg/L) 1 | Sample dilution (Times) 2 | Color of the reaction mixture 3 | OD 4 | Estimated COD (mg/L) 5 | Estimated final COD (mg/L) (Col. 2 × 5) 6 |
|---|---|---|---|---|---|
| Values at OD 585 nm | | | | | |
| Glucose: | | | | | |
| 320 | NA | C300 | 0.159 | NA | NA |
| 426 | NA | C400 | 0.187 | NA | NA |
| 535 | NA | C550 | 0.206 | NA | NA |
| Sample: Tea + Apple Pomace + Dabu (ssp) | | | | | |
| | Nil | C10000 | — | >10,000 | >10,000 |
| | 10 | C5000 | — | ≅5000 | ≅50,000 |
| | 100 | C550 | 0.216 | ≅550 | ≅55,000# |
| | 166.7 | C400 | 0.157 | 430 | 71681 |
| Values at OD 635 nm | | | | | |
| Glucose: | | | | | |
| 320 | NA | C300 | 0.141 | NA | NA |
| 426 | NA | C400 | 0.162 | NA | NA |
| 535 | NA | C550 | 0.195 | NA | NA |

TABLE 60-continued

Correlation between COD concentration, color of the reaction mixture and their OD at different wave lengths.

| COD (mg/L) 1 | Sample dilution (Times) 2 | Color of the reaction mixture 3 | OD 4 | Estimated COD (mg/L) 5 | Estimated final COD (mg/L) (Col. 2 × 5) 6 |
|---|---|---|---|---|---|
| Sample: Tea + Apple Pomace + Dabu (ssp) | | | | | |
| | Nil | C10000 | — | >10,000 | >10,000 |
| | 10 | C5000 | — | ≅5000 | ≅50,000 |
| | 100 | C550 | 0.195 | ≅550 | ≅55,000# |
| | 166.7 | C400 | 0.141 | 446 | 74348 |

COD as deducible from Table 2 given in Example 2.
D: Dark.
T: Turbid.
*OD out of range.
NA: Not applicable.
Samples are diluted to get an OD 585 in the range of 0.130 to 0.175 and OD 635 in the range of 0.120 to 0.160, to obtain a COD value in the range of 320 to 535 mg/L. (Based on the Tables 3 to 15 given in Examples 3 to 15).

EXAMPLE 61

Dissolved 0.15 g glucose in 25 mL distilled water. Aliquots from the stock solution were taken and diluted with water to achieve different COD concentrations in the range of 320 to 535 mg/L. A 30 mL sample of Damaged wheat grain and Dabu (ssp) was taken. Weighed 0.02 g $HgSO_4$ in separate 15 mL test tubes. 1.0 mL of glucose solution and sample were added to each test tube separately and mixed well. 0.5 mL of $K_2Cr_2O_7$ was added to each sample. 1.5 mL $H_2SO_4$ silver sulphate reagent was added slowly with continuous shaking. The color of the reaction mixture was noted down visually within 15 sec of incubation and also recorded spectrophotometrically at 585 and 635 nm against air. An approximate COD value of the sample was estimated from the color of standard reaction mixture prepared with glucose as reference material in the COD range of 200 to 100000 mg/L. OD 585 and OD 635 of the reaction mixture was read spectrophotometrically. OD 585 and 635 nm in the range of 0.130 to 0.175 and 0.120 to 0.160 respectively were considered and calculated with reference to glucose standard. (Glucose COD in the range of 320 to 535 mg/L corresponds to OD 585 and 635 nm in the range of 0.157 to 0.207 and 0.142 to 0.189, respectively).

COD of the sample was estimated to be 65,251 mg/L. (By Merck method and read on photometer).

Based on the color of the reaction mixture, COD of the sample was estimated to be around 45000 mg/L. On the basis of the dilution method and the spectrophotometric reading at OD 585 and OD 635 of the sample, COD was estimated to be 63625 and 58000 mg/l respectively. A comparison with the COD value calculated through Merck method reveals the following relation i.e. Our COD value (at OD 585)×1.02=COD value (Merck Method) or our COD value (at OD 635)×1.12=COD value (Merck Method).

Hence for a preliminary estimate of COD value color of the standard reaction mixture based on a range of glucose concentrations can be used as a reference. For samples, with COD concentration of 300 to 500 mg/L, OD 585 or OD 635 can be recorded for obtaining more precise values.

DWS(S3)+Dabu (ssp)

TABLE 61

Correlation between COD concentration, color of the reaction mixture and their OD at different wave lengths.

| COD (mg/L) 1 | Sample dilution (Times) 2 | Color of the reaction mixture 3 | OD 4 | Estimated COD (mg/L) 5 | Estimated final COD (mg/L) (Col. 2 × 5) 6 |
|---|---|---|---|---|---|
| Values at OD 585 nm | | | | | |
| Glucose: | | | | | |
| 320 | NA | C300 | 0.159 | NA | NA |
| 426 | NA | C400 | 0.187 | NA | NA |
| 535 | NA | C550 | 0.206 | NA | NA |
| Sample: DWS (S3) + Dabu (ssp) | | | | | |
| | Nil | C5500 | — | 5500 | ≅5500 |
| | 10 | C4000 | — | 4000 | ≅40,000 |
| | 100 | C450 | 0.168 | 450 | ≅45,000# |
| | 125 | C300 | 0.163 | 509 | 63625 |
| Values at OD 635 nm | | | | | |
| Glucose: | | | | | |
| 320 | NA | C300 | 0.141 | NA | NA |
| 426 | NA | C400 | 0.162 | NA | NA |
| 535 | NA | C550 | 0.195 | NA | NA |
| Sample: DWS (S3) + Dabu (ssp) | | | | | |
| | Nil | C5500 | — | 5500 | ≅5500 |
| | 10 | C4000 | — | 4000 | ≅40,000 |
| | 100 | C450 | 0.150 | 450 | ≅45,000# |
| | 125 | C300 | 0.145 | 464 | 58000 |

COD as deducible from Table 2 given in Example 2.
D: Dark.
T: Turbid.
*OD out of range.
NA: Not applicable.
Samples are diluted to get an OD 585 in the range of 0.130 to 0.175 and OD 635 in the range of 0.120 to 0.160, to obtain a COD value in the range of 320 to 535 mg/L. (Based on the Tables 3 to 15 given in Examples 3 to 15).

EXAMPLE 62

Dissolved 0.15 g glucose in 25 mL distilled water. Aliquots from the stock solution were taken and diluted with water to achieve different COD concentrations in the range of 320 to 535 mg/L. A 30 mL sample of Tea, Apple Pomace, Damaged wheat grain and NaCl (ssp) was taken. Weighed 0.02 g $HgSO_4$ in separate 15 mL test tubes. 1.0 mL of glucose solution and sample were added to each test tube separately and mixed well. 0.5 mL of $K_2Cr_2O_7$ was added to each sample. 1.5 mL $H_2SO_4$ silver sulphate reagent was added slowly with continuous shaking. The color of the reaction mixture was noted down visually within 15 sec of incubation and also recorded spectrophotometrically at 585 and 635 nm against air. An approximate COD value of the sample was estimated from the color of standard reaction mixture prepared with glucose as reference material in the COD range of 200 to 100000 mg/L. OD 585 and OD 635 of the reaction mixture was read spectrophotometrically. OD 585 and 635 nm in the range of 0.130 to 0.175 and 0.120 to 0.160 respectively were considered and calculated with reference to glucose standard. (Glucose COD in the range of 320 to 535 mg/L corresponds to OD 585 and 635 nm in the range of 0.157 to 0.207 and 0.142 to 0.189, respectively).

COD of the sample was estimated to be 27,163 mg/L. (By Merck method and read on photometer).

Based on the color of the reaction mixture, COD of the sample was estimated to be around 10000 mg/L. On the basis of the dilution method and the spectrophotometric reading at OD 585 and OD 635 of the sample, COD was estimated to be 16300 and 17450 mg/l respectively. A comparison with the COD value calculated through Merck method reveals the following relation i.e. Our COD value (at OD 585)×1.67=COD value (Merck Method) or our COD value (at OD 635)×1.56=COD value (Merck Method).

Hence for a preliminary estimate of COD value color of the standard reaction mixture based on a range of glucose concentrations can be used as a reference. For samples, with COD concentration of 300 to 500 mg/L, OD 585 or OD 635 can be recorded for obtaining more precise values.

TABLE 62

Correlation between COD concentration, color of the reaction mixture and their OD at different wave lengths.

| COD (mg/L) 1 | Sample dilution (Times) 2 | Color of the reaction mixture 3 | OD 4 | Estimated COD (mg/L) 5 | Estimated final COD (mg/L) (Col. 2 × 5) 6 |
|---|---|---|---|---|---|
| Values at OD 585 nm | | | | | |
| Glucose: | | | | | |
| 320 | NA | C300 | 0.158 | NA | NA |
| 426 | NA | C400 | 0.185 | NA | NA |
| 535 | NA | C550 | 0.207 | NA | NA |
| Sample: Tea + Apple Pomace + DWS (S3) + NaCl (ssp) | | | | | |
| | Nil | C10000 | — | ≅10,000 | ≅10,000# |
| | 50 | C300 | 0.134 | 326 | 16300 |
| | 66.7 | C300 | 0.112 | 300 | 20,010 |
| Values at OD 635 nm | | | | | |
| Glucose: | | | | | |
| 320 | NA | C300 | 0.132 | NA | NA |
| 426 | NA | C400 | 0.160 | NA | NA |
| 535 | NA | C550 | 0.195 | NA | NA |
| Sample: Tea + Apple Pomace + DWS (S3) + NaCl (ssp) | | | | | |
| | Nil | C10000 | — | ≅10,000 | ≅10,000# |
| | 50 | C300 | 0.120 | 349 | 17450 |
| | 66.7 | C300 | 0.099 | 300 | 20,010 |

COD as deducible from Table 2 given in Example 2.
D: Dark.
T: Turbid.
*OD out of range.
NA: Not applicable.
Samples are diluted to get an OD 585 in the range of 0.130 to 0.175 and OD 635 in the range of 0.120 to 0.160, to obtain a COD value in the range of 320 to 535 mg/L. (Based on the Tables 3 to 15 given in Examples 3 to 15).

EXAMPLE 63

Dissolved 0.15 g glucose in 25 mL distilled water. Aliquots from the stock solution were taken and diluted with water to achieve different COD concentrations in the range of 320 to 535 mg/L. A 30 mL sample of Tea, Apple Pomace, Damaged wheat grain and Glucose (ssp) was taken. Weighed 0.02 g $HgSO_4$ in separate 15 mL test tubes. 1.0 mL of glucose solution and sample were added to each test tube separately and mixed well. 0.5 mL of $K_2Cr_2O_7$ was added to each sample. 1.5 mL $H_2SO_4$ silver sulphate reagent was added slowly with continuous shaking. The color of the reaction mixture was noted down visually within 15 sec of incubation and also recorded spectrophotometrically at 585 and 635 nm against air. An approximate COD value of the sample was estimated from the color of standard reaction mixture prepared with glucose as reference material in the COD range of 200 to 100000 mg/L. OD 585 and OD 635 of the reaction mixture was read spectrophotometrically. OD 585 and 635 nm in the range of 0.130 to 0.175 and 0.120 to 0.160 respectively were considered and calculated with reference to glucose standard. (Glucose COD in the range of 320 to 535 mg/L corresponds to OD 585 and 635 nm in the range of 0.157 to 0.207 and 0.142 to 0.189, respectively).

COD of the sample was estimated to be 53,866 mg/L. (By Merck method and read on photometer).

Based on the color of the reaction mixture, COD of the sample was estimated to be around 50000 mg/L. On the basis of the dilution method and the spectrophotometric reading at OD 585 and OD 635 of the sample, COD was estimated to be 517000 and 41600 mg/l respectively. A comparison with the COD value calculated through Merck method reveals the following relation i.e. Our COD value (at OD 585)×1.04=COD value (Merck Method) or our COD value (at OD 635)×1.30=COD value (Merck Method).

Hence for a preliminary estimate of COD value color of the standard reaction mixture based on a range of glucose concentrations can be used as a reference. For samples, with COD concentration of 300 to 500 mg/L, OD 585 or OD 635 can be recorded for obtaining more precise values.

Tea+Apple Pomace+DWS (S3)+Glucose (ssp)

TABLE 63

Correlation between COD concentration, color of the reaction mixture and their OD at different wave lengths.

| COD (mg/L) | Sample dilution (Times) | Color of the reaction mixture | OD | Estimated COD (mg/L) | Estimated final COD (mg/L) (Col. 2 × 5) |
|---|---|---|---|---|---|
| 1 | 2 | 3 | 4 | 5 | 6 |
| Values at OD 585 nm | | | | | |
| Glucose: | | | | | |
| 320 | NA | C300 | 0.158 | NA | NA |
| 426 | NA | C400 | 0.185 | NA | NA |
| 535 | NA | C550 | 0.207 | NA | NA |
| Sample: Tea + Apple Pomace + DWS (S3) + Glucose (ssp) | | | | | |
| | Nil | C10000 | — | >10,000 | >10000 |
| | 10 | C5000 | — | 5000 | 50,000# |
| | 100 | C500 | 0.167 | 517 | 51700 |
| Values at OD 635 nm | | | | | |
| Glucose: | | | | | |
| 320 | NA | C300 | 0.132 | NA | NA |
| 426 | NA | C400 | 0.160 | NA | NA |
| 535 | NA | C550 | 0.195 | NA | NA |
| Sample: Tea + Apple Pomace + DWS (S3) + Glucose (ssp) | | | | | |
| | Nil | C10000 | — | >10,000 | >10000 |
| | 10 | C5000 | — | 5000 | 50,000# |
| | 100 | C400 | 0.150 | 416 | 41600 |

COD as deducible from Table 2 given in Example 2.
D: Dark.
T: Turbid.
*OD out of range.
NA: Not applicable.
Samples are diluted to get an OD 585 in the range of 0.130 to 0.175 and OD 635 in the range of 0.120 to 0.160, to obtain a COD value in the range of 320 to 535 mg/L. (Based on the Tables 3 to 15 given in Examples 3 to 15).

EXAMPLE 64

Dissolved 0.15 g glucose in 25 mL distilled water. Aliquots from the stock solution were taken and diluted with water to achieve different COD concentrations in the range of 320 to 535 mg/L. A 30 mL sample of Damaged wheat grain (ssp) was taken. Weighed 0.02 g $HgSO_4$ in separate 15 mL test tubes. 1.0 mL of glucose solution and sample were added to each test tube separately and mixed well. 0.5 mL of $K_2Cr_2O_7$ was added to each sample. 1.5 mL $H_2SO_4$ silver sulphate reagent was added slowly with continuous shaking. The color of the reaction mixture was noted down visually within 15 sec of incubation and also recorded spectrophotometrically at 585 and 635 nm against air. An approximate COD value of the sample was estimated from the color of standard reaction mixture prepared with glucose as reference material in the COD range of 200 to 100000 mg/L. OD 585 and OD 635 of the reaction mixture was read spectrophotometrically. OD 585 and 635 nm in the range of 0.130 to 0.175 and 0.120 to 0.160 respectively were considered and calculated with reference to glucose standard. (Glucose COD in the range of 320 to 535 mg/L corresponds to OD 585 and 635 nm in the range of 0.157 to 0.207 and 0.142 to 0.189, respectively).

COD of the sample was estimated to be 6649.3 mg/L. (By Merck method and read on photometer).

Based on the color of the reaction mixture, COD of the sample was estimated to be around 500 mg/L. On the basis of the dilution method and the spectrophotometric reading at OD 585 and OD 635 of the sample, COD was estimated to be 5260 and 5190 mg/l respectively. A comparison with the COD value calculated through Merck method reveals the following relation i.e. Our COD value (at OD 585)×1.26= COD value (Merck Method) or our COD value (at OD 635)×1.30=COD value (Merck Method).

Hence for a preliminary estimate of COD value color of the standard reaction mixture based on a range of glucose concentrations can be used as a reference. For samples, with COD concentration of 300 to 500 mg/L, OD 585 or OD 635 can be recorded for obtaining more precise values.

DWS (S3) (ssp)

TABLE 64

Correlation between COD concentration, color of the reaction mixture and their OD at different wave lengths.

| COD (mg/L) | Sample dilution (Times) | Color of the reaction mixture | OD | Estimated COD (mg/L) | Estimated final COD (mg/L) (Col. 2 × 5) |
|---|---|---|---|---|---|
| 1 | 2 | 3 | 4 | 5 | 6 |
| Values at OD 585 nm | | | | | |
| Glucose: | | | | | |
| 320 | NA | C300 | 0.159 | NA | NA |
| 426 | NA | C400 | 0.187 | NA | NA |
| 535 | NA | C550 | 0.210 | NA | NA |
| Sample: DWS (S3) (ssp) | | | | | |
| | Nil | C550 | — | 550 | 550# |
| | 10 | C400 | 0.172 | 526 | 5260 |
| Values at OD 635 nm | | | | | |
| Glucose: | | | | | |
| 320 | NA | C300 | 0.142 | NA | NA |
| 426 | NA | C400 | 0.167 | NA | NA |
| 535 | NA | C550 | 0.189 | NA | NA |

TABLE 64-continued

Correlation between COD concentration, color of the reaction mixture and their OD at different wave lengths.

| COD (mg/L) 1 | Sample dilution (Times) 2 | Color of the reaction mixture 3 | OD 4 | Estimated COD (mg/L) 5 | Estimated final COD (mg/L) (Col. 2 × 5) 6 |
|---|---|---|---|---|---|
| Sample: Digested POME (ssp) | | | | | |
| Nil | C550 | — | 550 | 550# | |
| 10 | C400 | 0.151 | 531 | 5310 | |

COD as deducible from Table 2 given in Example 2.
D: Dark.
T: Turbid.
*OD out of range.
NA: Not applicable.
Samples are diluted to get an OD 585 in the range of 0.130 to 0.175 and OD 635 in the range of 0.120 to 0.160, to obtain a COD value in the range of 320 to 535 mg/L. (Based on the Tables 3 to 15 given in Examples 3 to 15).

EXAMPLE 65

Dissolved 0.15 g glucose in 25 mL distilled water. Aliquots from the stock solution were taken and diluted with water to achieve different COD concentrations in the range of 320 to 535 mg/L. A 30 mL sample of Tea, Apple Pomace, Damaged wheat grain and Glucose (ssp) was taken. Weighed 0.02 g $HgSO_4$ in separate 15 mL test tubes. 1.0 mL of glucose solution and sample were added to each test tube separately and mixed well. 0.5 mL of $K_2Cr_2O_7$ was added to each sample. 1.5 mL $H_2SO_4$ silver sulphate reagent was added slowly with continuous shaking. The color of the reaction mixture was noted down visually within 15 sec of incubation and also recorded spectrophotometrically at 585 and 635 nm against air. An approximate COD value of the sample was estimated from the color of standard reaction mixture prepared with glucose as reference material in the COD range of 200 to 100000 mg/L. OD 585 and OD 635 of the reaction mixture was read spectrophotometrically. OD 585 and 635 nm in the range of 0.130 to 0.175 and 0.120 to 0.160 respectively were considered and calculated with reference to glucose standard. (Glucose COD in the range of 320 to 535 mg/L corresponds to OD 585 and 635 nm in the range of 0.157 to 0.207 and 0.142 to 0.189, respectively).

COD of the sample was estimated to be 30,866 mg/L. (By Merck method and read on photometer).

Based on the color of the reaction mixture, COD of the sample was estimated to be around 20000 mg/L. On the basis of the dilution method and the spectrophotometric reading at OD 585 and OD 635 of the sample, COD was estimated to be 20,850 and 20,450 mg/l respectively. A comparison with the COD value calculated through Merck method reveals the following relation i.e. Our COD value (at OD 585)×1.48=COD value (Merck Method) or our COD value (at OD 635)×1.51=COD value (Merck Method).

Hence for a preliminary estimate of COD value color of the standard reaction mixture based on a range of glucose concentrations can be used as a reference. For samples, with COD concentration of 300 to 500 mg/L, OD 585 or OD 635 can be recorded for obtaining more precise values.

Tea+Apple Pomace+DWS (S3)+Glucose (ssp)

TABLE 65

Correlation between COD concentration, color of the reaction mixture and their OD at different wave lengths.

| COD (mg/L) 1 | Sample dilution (Times) 2 | Color of the reaction mixture 3 | OD 4 | Estimated COD (mg/L) 5 | Estimated final COD (mg/L) (Col. 2 × 5) 6 |
|---|---|---|---|---|---|
| Values at OD 585 nm | | | | | |
| Glucose: | | | | | |
| 320 | NA | C300 | 0.159 | NA | NA |
| 426 | NA | C400 | 0.187 | NA | NA |
| 535 | NA | C550 | 0.210 | NA | NA |
| Sample: Tea + Apple Pomace + DWS (S3) + Glucose (ssp) | | | | | |
| | Nil | C10000 | — | >10,000 | |
| | 10 | C2000 | 0.359 | 2000 | 20,000# |
| | 50 | C400 | 0.152 | 417 | 20,850 |
| Values at OD 635 nm | | | | | |
| Glucose: | | | | | |
| 320 | NA | C300 | 0.142 | NA | NA |
| 426 | NA | C400 | 0.167 | NA | NA |
| 535 | NA | C550 | 0.189 | NA | NA |
| Sample: Tea + Apple Pomace + DWS (S3) + Glucose (ssp) | | | | | |
| | Nil | C10000 | — | >10,000 | |
| | 10 | C2000 | 0.359 | 2000 | 20,000# |
| | 50 | C400 | 0.152 | 409 | 20,450 |

COD as deducible from Table 2 given in Example 2.
D: Dark.
T: Turbid.
*OD out of range.
NA: Not applicable.
Samples are diluted to get an OD 585 in the range of 0.130 to 0.175 and OD 635 in the range of 0.120 to 0.160, to obtain a COD value in the range of 320 to 535 mg/L. (Based on the Tables 3 to 15 given in Examples 3 to 15).

The main advantages of the present invention are
1. The test can be carried out rapidly.
2. The test does not require any major instrument.
3. The test is very cheap.
4. The test requires very small amount of reagents.
5. The test is easy to perform.
6. The test can be done without the need for specially trained technician.
7. The test can be performed with the help of a kit also.

What is claimed is:

1. A rapid method for the estimation of COD of an effluent from domestic, industrial, municipal and other sources, said method comprising the steps of:
   a) preparing a set of standard glucose solutions by dissolving glucose in distilled water at a concentration ranging between 300 mg/L to 500 mg/L, with a COD concentration of 320 mg/L to 535 mg/L,
   b) mixing 1 mL of standard glucose solutions from step (a), individually, with three reagents, consisting of 0.02 g mercuric sulfate, 0.5 mL of 0.25 N potassium dichromate solution and 1.5 mL of sulfuric acid—silver sulfate in a sequential manner,
   c) mixing 1 mL of a sample to be tested with 0.01 to 0.03 g mercuric sulfate per ml of standard glucose solution, 0.5 mL of 0.25 N to 0.30 N potassium dichromate and 1.5 mL of sulfuric acid silver sulfate reagents in a sequential manner and noting down the color and if the color of the reaction mixture turns (color code C10000) brown, d) diluting the sample according to table 1 (a) with distilled water till a particular color range of about C100 to C10000 is achieved as shown in FIG. 1 of the accompanying drawing, e) further diluting the sample with distilled water to obtain a COD range between about 320 to 535 mg/L wherein the dilution is determined according to Tables 1(a) & (b), TABLE 1(a)

| Color of the reaction mixture | Required dilution of sample | Color code | Expected COD of unknown sample (mg/L) |
|---|---|---|---|
| C 10000 | 10 | C1000 | 10000 |
| C 10000 | 100 | C100–C500 | 10000–50000 |
| C 10000 | 200 | C250–C500 | 50000–100000 |
| C 10000 | 500 | C200–C2000 | 100000–1000000 |

TABLE 1(b)

| Color of the reaction mixture | Expected COD (mg/L) | Dilution required to bring COD value (300–500 mg/L) |
|---|---|---|
| C9000 | 9000–9500 | 18–31 |
| C6000 | 6000–8500 | 12–28 |
| C2000 | 2000–5500 | 4–18 |
| C1500 | 1500–1900 | 3–6 |
| C1200 | 1200–1400 | 2–5 |
| C600 | 600–1100 | 2–4 |
| C500 | 500–550 | NIL |
| C400 | 400–150 | NIL |
| C300 | 300–350 | NIL |
| C200 | 200–250 | NIL |
| C150 | 100–150 | NIL |
| C100 | 00–100 | NIL | f) mixing 1 mL of diluted sample from step (e), individually, with three reagents, consisting of 0.01 to 0.03 g mercuric sulfate per ml of standard glucose solution, 0.5 ml of 0.25 N to 0.30 N potassium dichromate solution and 1.5 mL of sulfuric acid—silver sulfate in the above sequential manner, g) matching the color of the reaction mixture of the above sample (step f) with the COD color chart provided in FIG. 1 of the accompanying drawing, h) noting the optical density (OD) of the reaction mixture of standard glucose solutions (step b) and sample (step f) at 585 nm or 635 nm, against air, i) drawing a correlation between the OD values of above sample with OD values of standard glucose solutions, j) multiplying the OD value of sample (step h) with a correction factor of 1.2, comparing this value (A) with the OD value of standard glucose solution of COD value 320 to 535 mg/l, k) multiplying value (A) with the compared COD value of standard Glucose solution and divided by the respective OD value of the glucose standard (B) and I) then multiply value (B) with a dilution factor (in case of diluted sample) to obtain the COD value of the sample in terms of mg/l, all of said steps being conducted at room temperature.

2. A method as claimed in claim 1 wherein, the Dilution Factor is the total volume used divided by the volume of the sample.

3. A method as claimed in claim 1 wherein, the effluent used is selected from domestic, industrial, municipal, agricultural and other waste material sources.

4. A method as claimed in claim 1 wherein, the waste material is in the form of a solid, liquid, semi-solid or viscous forms.

5. A method as claimed in claim 1 wherein, the reagents comprise of $HgSO_4$, glucose standard solutions, $K_2Cr_2O_7$ solution and $H_2SO_4$—silver sulfate reagent.

6. A method as claimed in claim 1 wherein, the volume of the test sample or standard solution ranges is from about 20 to 100 ml.

7. A method as claimed in claim 1 wherein, the incubation is carried out for a period in the range of 15 seconds to 1 minute.

8. A method as claimed in claim 1 wherein, the COD is estimated in the range of between 80 to 106700 mg/L.

9. A method as claimed in claim 1 wherein, the glucose concentration is tested in the range between 50 to 100000 mg/L.

10. A method as claimed in claim 1 wherein, the $HgSO_4$ used in the test sample is 0.02 g.

11. A method as claimed in claim 1 wherein, the $K_2Cr_2O_7$ used in the test sample is from about 0.25 Normal to 0.30 Normal.

12. A method as claimed in claim 1 wherein, the $H_2SO_4$—silver sulfate reagent used in the test samples is 1.5 mL.

13. A method as claimed in claim 1 wherein, the COD color chart is applicable for the COD values in the range of 100 to 10,000 mg/L.

14. A method as claimed in claim 1 wherein, the test samples of having a COD more than 10000 mg/L are diluted appropriately.

15. A method as claimed in claim 1 wherein, the O.D of the sample is read at the wavelengths 585 and 635 nm.

16. A method as claimed in claim 1 wherein, the optical density readings are measured for the COD values ranging from 320 to 535 mg/L.

17. A method as claimed in claim 1 wherein, the sample is in the form of slurry.

18. A method as claimed in claim 1 wherein, the test sample comprises agricultural waste, municipal market waste, fruit and food industry waste, beverages, chemicals, microbes and animal waste.

19. A method as claimed in claim 1 wherein, in step (d) the dilution of samples, provides a dark brown reaction mixture, falling in the range of 10 to 500 for approximate COD values of 10000 mg/l and above as given in Table 1c and further dilution of 0 to 31 is done to bring the COD in the range of 300 to 500 mg/l as given in Table 1d.

TABLE 1(c)

| Color of the reaction mixture | Color code of the reaction mixture as per the provided chart | Dilution required to bring the COD values in the range of 100–1000 mg/l | Color obtained on dilution as per the provided color chart | Expected COD of the reaction mixture (mg/l) | Expected COD of unknown sample (mg/l) |
|---|---|---|---|---|---|
| Dark brown | C 10000 to C 100000 | ix) 10<br>x) 100<br>xi) 200<br>xii) 500 | C 1000<br>C 100–C500<br>C 250–C 500<br>C 200 to C 2000 | 1000<br>100 to 500<br>250 to 500<br>200 to 2000 | 10000<br>10000 to 50000<br>50000 to 100000<br>100000 to 1000000 |

TABLE 1(d)

| Color group | Color of the reaction mixture | Color code of the reaction mixture as per the chart provided | Expected COD of the reaction mixture | Dilution required to bring the COD values in the range of 300 to 500 mg/l |
|---|---|---|---|---|
| A | Yellowish | C 100 to C 250 | 1 to 250 | Nil |
| B | Yellowish | C 300 to C 550 | 300 to 550 | Nil |
| C | Greenish blue | C 600 to C 1000 | 600 to 1000 | 2 to 4 |
| D | Blue to grayish blue | C 1500 to C 2500 | 1500 to 2500 | 3 to 6 |
| E | Dirty brown | C 3000 to C 5500 | 3000 to 5500 | 6 to 18 |
| F | Cola brown | C 6000 to C 8500 | 6000 to 8500 | 12 to 28 |
| G | Blackish brown | C 9000 to 9500 | 9000 to 9500 | 18–31 |

20. A method as claimed in claim 1 wherein, in step (e), the samples provide a yellowish to blackish brown colored reaction mixture falling in the range of 100 to 9500 mg/l COD and the samples are further diluted to nil to 31 times to obtain a diluted sample in the COD range of about 300 to 500 mg/l, according to the Table 1(d).

21. A method as claimed in claim 1 wherein, in step (d) the dilution of samples and color groups range from (A) to (G) for approximate COD values lying in the range of about 100 to 9500 mg/l as given in Table 1(d).

* * * * *